(12) United States Patent
Andersen et al.

(10) Patent No.: US 8,563,038 B2
(45) Date of Patent: Oct. 22, 2013

(54) FORMULATIONS AND METHODS FOR THE CONTROLLED RELEASE OF ACTIVE DRUG SUBSTANCES

(75) Inventors: Christine Andersen, Vedbaek (DK); Karsten Lindhardt, Haslev (DK); Jan Martin Oevergaard, Frederikssund (DK); Louise Inoka Lyhne-Iversen, Gentofte (DK); Martin Rex Olsen, Holbaek (DK); Anne-Mette Haahr, Birkeroed (DK); Pernille Kristine Hoeyrup Hemmingsen, Bagsvaerd (DK)

(73) Assignee: Egalet Ltd., London (GB)

( * ) Notice: Subject to any disclaimer, the term of this patent is extended or adjusted under 35 U.S.C. 154(b) by 0 days.

(21) Appl. No.: 12/823,067

(22) Filed: Jun. 24, 2010

(65) Prior Publication Data

US 2011/0159100 A1    Jun. 30, 2011

Related U.S. Application Data

(60) Provisional application No. 61/219,817, filed on Jun. 24, 2009.

(30) Foreign Application Priority Data

Jun. 24, 2009   (DK) ................................ 2009 00782

(51) Int. Cl.
*A61K 31/485* (2006.01)
*A61K 9/10* (2006.01)
*A61P 29/00* (2006.01)

(52) U.S. Cl.
USPC ............ 424/486; 424/468; 514/282; 514/411

(58) Field of Classification Search
USPC ........................... 424/486, 468; 514/282, 411
See application file for complete search history.

(56) References Cited

U.S. PATENT DOCUMENTS

| | | | |
|---|---|---|---|
| 2,685,553 A | 8/1954 | Carroll et al. | |
| 4,034,758 A | 7/1977 | Theeuwes | |
| 4,449,983 A | 5/1984 | Cortese et al. | |
| 4,898,733 A | 2/1990 | DePrince et al. | |
| 5,019,396 A | 5/1991 | Ayer et al. | |
| 5,213,808 A | 5/1993 | Bar Shalom et al. | |
| 5,609,885 A | 3/1997 | Rivera et al. | |
| 5,869,097 A | 2/1999 | Wong et al. | |
| 6,103,261 A | 8/2000 | Chasin et al. | |
| 2003/0118641 A1 | 6/2003 | Maloney et al. | |
| 2003/0133976 A1 | 7/2003 | Pather et al. | |
| 2004/0151772 A1* | 8/2004 | Andersen et al. ............ | 424/468 |
| 2005/0053655 A1 | 3/2005 | Yang et al. | |
| 2005/0158382 A1 | 7/2005 | Cruz et al. | |
| 2006/0193912 A1 | 8/2006 | Ketsela et al. | |
| 2007/0003617 A1* | 1/2007 | Fischer et al. ................ | 424/468 |
| 2007/0004797 A1 | 1/2007 | Weyers et al. | |
| 2007/0224129 A1 | 9/2007 | Guimberteau et al. | |
| 2007/0264346 A1 | 11/2007 | Guimberteau et al. | |
| 2008/0152595 A1 | 6/2008 | Emigh et al. | |
| 2008/0166407 A1 | 7/2008 | Shalaby et al. | |
| 2008/0299199 A1 | 12/2008 | Bar Shalom et al. | |
| 2008/0311205 A1 | 12/2008 | Habib et al. | |
| 2009/0022790 A1 | 1/2009 | Flath et al. | |
| 2010/0203129 A1* | 8/2010 | Andersen et al. ............ | 424/474 |
| 2010/0203130 A1 | 8/2010 | Tygesen et al. | |
| 2010/0204259 A1 | 8/2010 | Tygesen et al. | |
| 2010/0239667 A1 | 9/2010 | Hemmingsen et al. | |
| 2010/0291205 A1 | 11/2010 | Downie et al. | |

FOREIGN PATENT DOCUMENTS

| | | | |
|---|---|---|---|
| DE | 202006014131 | 1/2007 | |
| EP | 0435726 | 8/1991 | |
| EP | 0493513 | 7/1992 | |
| EP | 0406315 | 11/1992 | |
| EP | 1213014 | 6/2002 | |
| WO | WO 89/09066 | 10/1989 | |
| WO | WO 91/04015 | 4/1991 | |
| WO | WO 95/22962 | 8/1995 | |
| WO | WO 99/51208 | 10/1999 | |
| WO | WO 00/41704 | 7/2000 | |
| WO | WO 03/024426 | 3/2003 | |
| WO | WO 03/024429 | * | 3/2003 |
| WO | WO 03/024430 | 3/2003 | |
| WO | WO 03/075897 | 9/2003 | |
| WO | WO 03/082204 | 10/2003 | |
| WO | WO 2004/041252 | 5/2004 | |
| WO | WO 2004/084868 | 10/2004 | |
| WO | WO 2004/084869 | 10/2004 | |
| WO | WO 2004/093819 | 11/2004 | |

(Continued)

OTHER PUBLICATIONS

Haahr et al. (Poster- Drug abuse resistant, controlled release using Egalet dosage units. Proceedings of the 34th annual Meeting Exposition of the Controlled Release Society Jul. 7-11 2007).*
Katikaneni et al. Ethylcellulose matrix controlled release tablets of a water-soluble drug. International Journal of Pharmaceutics 123 pp. 119-125 1995.*
Clin. Pharmacokinet. 2002; 41(10):751-90 abstract.*
Notification of Transmittal of the International Search Report and the Written Opinion of the International Searching Authority issued Jul. 8, 2008 in the International Application No. PCT/DK2008/000016.
International Type Search Report issued Jun. 17, 2009 in the International Application No. DK 2009001925.
Notification of Transmittal of the International Search Report and the Written Opinion of the International Searching Authority issued Feb. 6, 2010 in the International Application No. PCT/DK2010/050016.

(Continued)

*Primary Examiner* — Anoop Singh
*Assistant Examiner* — Anna Falkowitz
(74) *Attorney, Agent, or Firm* — Stoel Rives, LLP; Samuel E. Webb; Zhi-Xiang Alex Oh

(57) ABSTRACT

Controlled release formulations and methods for preparing controlled release formulations for delivery of active drug substances are described herein. The formulations described herein may be employed to produce pharmaceutical compositions, such as controlled release dosage forms, adjusted to a specific administration scheme.

37 Claims, 15 Drawing Sheets

(56) References Cited

FOREIGN PATENT DOCUMENTS

| WO | WO 2004/093843 | 11/2004 |
|---|---|---|
| WO | WO 2006/058249 | 1/2006 |
| WO | WO 2006/026504 | 3/2006 |
| WO | WO 2006/106344 | 10/2006 |
| WO | WO 2005/107713 | 11/2006 |
| WO | WO 2006/128471 | 12/2006 |
| WO | WO 2007/131357 | 11/2007 |
| WO | WO 2008/086804 | 7/2008 |
| WO | WO 2008/148798 | 12/2008 |
| WO | WO 2010/088911 | 8/2010 |
| WO | WO 2010/089132 | 8/2010 |

OTHER PUBLICATIONS

Notification of Transmittal of the International Search Report and the Written Opinion of the International Searching Authority issued May 28, 2010 in International Application No. PCT/DK2010/000019.
Preliminary Amendment filed Jul. 13, 2009 in corresponding U.S. Appl. No. 12/253,045.
Camu, et al., "Pharmacology of Systemic Analegesocs," Best Pract Res Clin Anaesthesiol 2002; 16(4):475-88.
Dahlstrom, et al., "Patient-Controlled Analegesic Therapy, Part IV: Pharmacokinetics and Analgesic Plasma Concentrations of Morphine," Clin Pharmacohinet 1982; 7:266-79.
Fischer, et al., "Nonmedical Use of Prescription Opioids: Furthering a Meaningful Research Agenda," J. Pain. 9:6, 2008 490-493.
Graves, et al., "Relationship Between Plasma Morphine Concentrations and Pharmacologic Effects in Postoperative Patients Using Patient-Controlled Analegesia," Clin Pharm 1985; 4:41-7.
L. Qui, et al., "Design of a Core-Shelled Polymer Cylinder for Potential Programmable Drug Delivery," Int. J. Pharm. 2001; 219:151-160.
Meyer, et al., "Awareness Topic: Mitigating the Risks of Ethanol Induced Dose Dumping from Oral Sustained/Controlled Release Dosage Forms," FDA's ACPS Meeting, Oct. 2005.
National Institute on Drug Abuse, Monitoring the Future, "National Results on Adolescent Drug Use—Overview of Key Findings 2009," http://www.monitoringthefuture.org/ (Originally Published in May 2010).
National Institute on Drug Abuse, Monitoring the Future, "National Results on Adolescent Drug Use—Overview of Key Findings 2008," http://www.samhsa.gov/ (Originally Published in May 2009).
National Institute of Drug Abuse, 2008 http://www.nida.nih.gov/dmgpages/prescription.html (Last Accessed on Jul. 15, 2008).
Rachel, et al., "Mu Opioid Receptor Regulation and Opiate Responsiveness," The AAPS Journal 2005; 7(3):Article 60.
International Preliminary Report on Patentability issued Jul. 16, 2009 in corresponding International Application No. PCT/DK2008/000016, now WO 2008/086804.
Notification of Transmittal of the International Search Report and the Written Opinion of the International Searching Authority issued Apr. 21, 2010 in International Application No. PCT/EP2010/000728.
International Preliminary Report on Patentability issued Aug. 6, 2011 in corresponding International Application No. PCT/EP2010/000728, now WO 2010/089132.
International Preliminary Report on Patentability issued Aug. 6, 2011 in corresponding International Application No. PCT/DK2010/000019, now WO 2010/088911.
Notification of Transmittal of the International Search Report and the Written opinion of the International Searching Authority issued Jan. 28, 2009 in International Application No. PCT/US2008/056910.
First Office Action issued Feb. 24, 2012 in co-pending U.S. Appl. No. 12/701,248.
Response to first Office Action filed Jun. 21, 2012 in co-pending U.S. Appl. No. 12/701,248.
Office Action issued Oct. 26, 2011 in U.S. Appl. No. 12/523,045, now US 2010/0291205.
Response to Oct. 26, 2011 Office Action filed Feb. 21, 2012 in co-pending U.S. Appl. No. 12/523,045, now US 2010/0291205.
Office Action issued May 24, 2012 in U.S. Appl. No. 12/523,045, now US 2010/0291205.
First Office Action issued Apr. 11, 2012 in U.S. Appl. No. 12/694,197, now US 2010/0203129.
Response to First Office Action filed Jul. 11, 2012 in U.S. Appl. No. 12/694,197, now US 2010/0203129.
Hemmingsen, et al., "Drug Abuse Resistant, Controlled Release, Using Egalet Dosage Units" poster. Published Jun. 28, 2007. (www.rxlist.com/miralax-drug.htm) as referenced Oct. 19, 2011.
Office Action issued Dec. 17, 2012 in co-pending U.S. Appl. No. 12/701,429, now US 2010/0203130.
Response to First Office Action filed Mar. 13, 2013 in in co-pending U.S. Appl. No. 12/701,429, now US 2010/0203130.
Second Office Action issued Jul. 20, 2012 in co-pending U.S. Appl. No. 12/701,248.
Response to Jul. 20, 2012 Office Action filed Oct. 22, 2012 in co-pending U.S. Appl. No. 12/701,248.
Interview Summary issued Dec. 12, 2012 in co-pending U.S. Appl. No. 12/701,248.
Response to May 24, 2012 Office Action filed Aug. 7, 2012 in U.S. Appl. No. 12/523,045, now US 2010/0291205.
Interview Summary issued Dec. 14, 2012 in U.S. Appl. No. 12/523,045, now US 2010/0291205.
First Office Action issued Mar. 7, 2013 in co-pending U.S. Appl. No. 12/602,953, now US 2010/0239667.
Final Office Action issued Sep. 14, 2012 in co-pending U.S. Appl. No. 12/694,197, now US 2010/0203129.
Response to Final Office Action filed Mar. 13, 2013 in co-pending U.S. Appl. No. 12/694,197, now US 2010/0203129.
Brannan, et al. (Geometry 2nd Edition. Cambridge University Press: NY; 2012 p. 78).

\* cited by examiner

III

IV

FORMULATIONS AND METHODS FOR THE CONTROLLED RELEASE OF ACTIVE DRUG SUBSTANCES

RELATED APPLICATIONS

This application claims the benefit of U.S. Provisional Application No. 61/219,817, filed on Jun. 24, 2009, the contents of which are incorporated herein by reference.

FIELD OF INVENTION

Formulations and methods for the controlled release of active drug substances are described herein. In certain embodiments, formulations and methods useful for once daily administration of active drug substances are provided.

BACKGROUND OF INVENTION

Many active drug substances must be administered relatively frequently in order to be functional over a longer time period. Therefore controlled release formulations allowing less frequent administration, but still having clinical efficacy over the entire time interval between administrations, are desirable.

This is for example the case for analgesics for treating pain. The pain relieving effect should be effective for the entire interval between individual administrations of the analgesic.

SUMMARY OF INVENTION

Controlled release formulations and methods for preparing controlled release formulations for delivery of active drug substances are described herein. The formulations described herein may be employed to produce pharmaceutical compositions, such as controlled release dosage forms, adjusted to a specific administration scheme. In specific embodiments, the formulations described herein provide controlled release of one or more active drug substances over a period of time ranging from about 20 hours to about 28 hours. In certain such embodiments, the formulations provide controlled release of clinically effective amounts of one or more active drug substances over a period of about 20 hours to 28 hours. Methods for the controlled release of active drug substances are also provided herein. And in certain embodiments, such methods include administering a controlled release formulation as described herein to an individual in need thereof.

In some embodiments the formulations described herein are provided as pharmaceutical compositions, such as, for example, controlled release dosage forms, that provide continued administration of at least one active drug substance over an interval of time of about 20 to 28 hours, and are configured such that, when such formulations are administered to a subject at intervals ranging from about 20 to 28 hours, the dosage form delivers the at least one drug substance in an amount that remains clinically effective throughout the interval between administrations.

It has been found that the geometry of certain controlled release formulations can be altered to obtain desired controlled release characteristics, and in particular embodiments, it has been found that pharmaceutical compositions as described herein of a certain length are useful for continued administration of at least one active drug substance over an interval ranging from about 20 to 28 hours between administrations. In certain such embodiments, it has been found that relatively longer dosage forms are suited to providing continued administration of at least one drug substance over a relatively longer period of time, while relatively shorter dosage forms are useful for continued administration of at least one drug substance over a shorter interval between administrations.

In particular embodiments, the formulations described herein are provided as pharmaceutical compositions comprising
a) a matrix composition comprising
  i) an active drug substance which may be any of the active drug substances described herein; and
  ii) at least one polyglycol, which may be any of the polyglycols described herein; and
b) a coating as described herein having at least one opening exposing at least one surface of said matrix, said coating being substantially impermeable to an aqueous medium;

In some such embodiments, the matrix composition included in the pharmaceutical composition has a cylindrical shape and, optionally, tapered end(s) (said cylindrical shape may be any of the shapes described herein), is formulated and configured at a length that facilitates controlled delivery of the active drug substance over a desired dosing interval, and said matrix is substantially surrounded by the coating, except at the one or more openings. Pharmaceutical compositions according to such embodiments may be formulated for continued administration of the active drug substance to an individual in need thereof over an interval of about 20 to 28 hours (e.g., a 24 hour interval). In one such embodiment, the composition delivers clinically effective amounts of the active drug substance to the individual over an interval of about 20 to 28 hours (e.g., a 24 hour interval). Such compositions facilitate methods of continued administration of the active drug substance, wherein the composition is administered to the individual in need thereof at intervals ranging from about 20 hours to 28 hours (e.g., a 24 hour interval).

In certain embodiments, the formulations described herein may be prepared as pharmaceutical compositions exhibiting particular pharmacological profiles. In certain embodiments, such pharmaceutical compositions include a matrix composition as detailed herein. In embodiments of the pharmaceutical compositions formulated and produced to provide a particular pharmacological profile, such compositions may be formulated and produced to provide, for example, a pharmacological profile described in greater detail below.

Methods of treating an individual in need are also described herein. In certain embodiments, such methods include providing a formulation according to the present description and administering a clinically effective amount of such formulation to the individual. Moreover, in specific such embodiments, the formulation may be provided as a pharmaceutical composition as detailed herein, including pharmaceutical compositions including a matrix composition. In further such embodiments, the formulation may be produced and administered in a manner that achieves a particular pharmacological profile, as described herein. In specific embodiments, methods of treating an individual suffering from pain are described.

Administration of the formulations described herein may be carried out according to any of the methods described herein. Moreover, examples of individuals in need of the formulations and methods provided herein are described in greater detail below.

DETAILED DESCRIPTION OF THE INVENTION

Definitions

Figure 1:
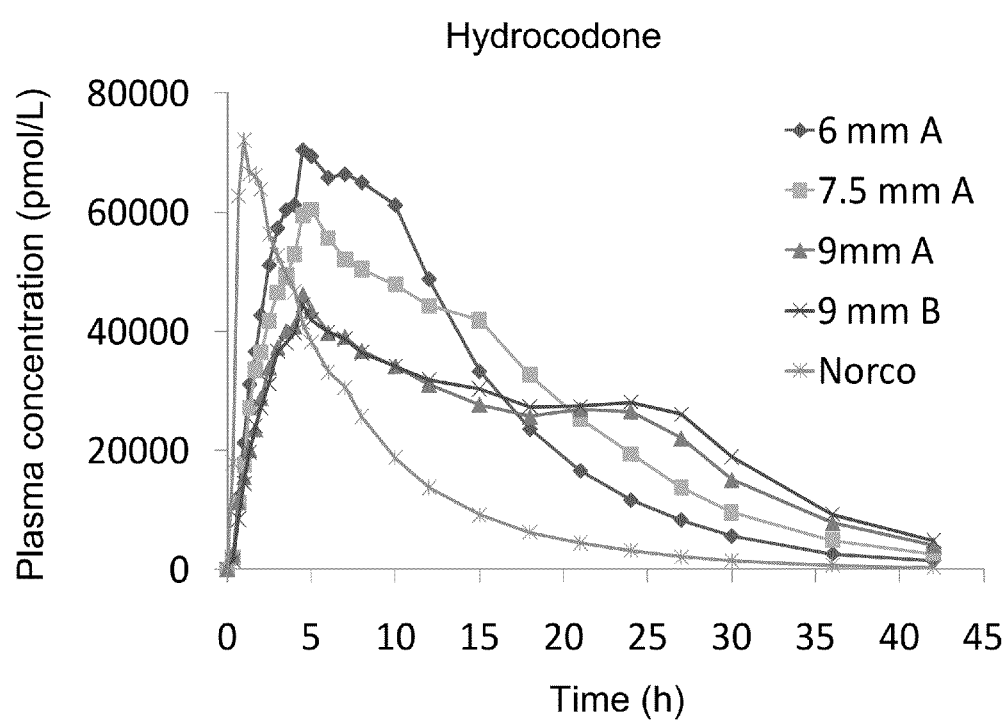
FIG. 1 shows the mean hydrocodone plasma concentration (pmol/L) versus time (h) curve after single dose administration by dose group (0-42 h). Formulation A (6 mm) is treatment A, formulation A (7.5 mm) is treatment B, formulation A (9 mm) is treatment C, formulation B (9 mm) is treatment D and Norco® is treatment E.

The term "cylindrical shape" as used herein refers to any geometrical shape having the same cross section area throughout the length of the geometrical shape. The cross section of a cylinder within the meaning of the present invention may have any two dimensional shape, for example the cross section may be circular, oval, rectangular, triangular, angular or star shaped. In specific embodiments, the pharmaceutical compositions described herein have a cylindrical shape, wherein the end(s) are optionally tapered.

The term "cross section of the matrix" is used to describe the cross section of the pharmaceutical compositions described herein, including matrix compositions, in the cylindrical part of the pharmaceutical composition. Thus, in embodiments, wherein the ends of the pharmaceutical composition are tapered, the term "cross section of the matrix" does not refer to the cross section of the tapered ends.

The terms "cross section area" or "cross sectional area" refer to the area of the cross section of the pharmaceutical compositions described herein. Depending on the position and shape of the openings of the coating, a specific area of the matrix included in the pharmaceutical composition is exposed to its surroundings. In certain embodiments, at least one opening that is essentially the same size and shape as the cross sectional area of the pharmaceutical composition is provided in the coating. In some such embodiments, the coating includes two openings that are essentially the same size and shape as the cross sectional area of the pharmaceutical composition.

The term "mean residence time" or MRT describes the average time for all the drug molecules to reside in the body. MRT may be considered also as the mean transit time or mean sojourn time.

MRT is calculated as $AUMC_{0-inf}/AUC_{0-inf}$ where $AUMC_{0-inf}$ is the area under the first moment curve from time zero to infinity. $AUMC_{0-inf}=AUMC_{0-t}+t*C_t/K_{el}+C_t/(K_{el})$.

The term "steady state" refers to the state when the plasma concentration level of an active drug substance following one dosing is the same within the standard deviation as the plasma concentration level following the next dosing. Thus, for pharmaceutical compositions for once daily administration then at steady state $AUC_{(0-24h)d}=AUC_{(0-24h)d+1}$ +/−the standard deviation, and $C_{max(0-24h)d}=C_{max(0-24h)d+1}$ +/−the standard deviation, where "h" is hours and "d" is day.

The term "substantially impermeable" as used herein refers to a material, for example, a coating, that is impermeable to aqueous medium for at least 24 hours. Therefore, in certain embodiments, a substantially impermeable coating as described herein in association with a pharmaceutical composition is impermeable to aqueous medium for at least 24 hours. In some such embodiments, the substantially impermeable coating is impermeable to aqueous medium for at least 48 hours.

The term "through" is defined as the average plasma concentration in a steady state individual just prior to the following dose. Thus, for pharmaceutical compositions prepared for continued administration of an active drug substance at intervals of about 20 to 28 hours (e.g., a 24 hour interval) between individual administrations, the trough is the average plasma concentration in a steady state individual 20 to 28 hours (e.g., a 24 hour interval) after dosing and just prior to the following dose. A steady state simulation may be calculated based on measurement of active drug substance or metabolites in serum after a single dose administration and based on such a simulation a theoretical trough may be determined. As exemplified herein, the trough may be determined as an average of the trough in at least 5 different individuals.

The term "$C_{min}$" is defined by the average lowest plasma concentration observed over a dosing interval. Thus, for pharmaceutical compositions prepared for continued administration over an interval of about 20 to 28 hours between individual administrations, the $C_{min}$ is defined by the average lowest plasma concentration observed over the dosing-interval of about 20 to 28 hours (e.g., a 24 hour interval). As exemplified herein, $C_{min}$ may be determined as an average of $C_{min}$ in at least 5 different individuals.

The term "steady state $C_{24}$" is defined as the average plasma concentration of an active drug substance in a steady state individual observed 24 hours after last administration of said active drug substance. A steady state simulation may be calculated based on measurement of active drug substance or metabolites in serum after a single dose administration and based on such a simulation a theoretical $C_{24}$ may be determined. As exemplified herein, "steady state $C_{24}$" may be determined as an average of "steady state $C_{24}$" in at least 5 different individuals.

The term "steady state $C_{max}$" is the average highest plasma concentration at steady state observed over the dosing interval. Thus, for pharmaceutical compositions for continued administration of an active drug substance over an interval of about 20 to about 28 hours (e.g., a 24 hour interval) between individual administrations, $C_{max}$ is defined by the highest plasma concentration at steady state observed over the dosing-interval. $C_{max}$ may also be referred to as "peak" plasma concentration. A steady state simulation may be calculated based on measurement of active drug substance or metabolites in serum after a single dose administration and based on such a simulation, a theoretical steady state $C_{max}$ may be determined. As exemplified herein, "steady state $C_{max}$" may be determined as an average of "steady state $C_{max}$" in at least 5 different individuals.

The term "steady state individual" refers to an individual to whom the pharmaceutical compositions described herein have been administered for a sufficient number of times in order to have arrived at steady state. Thus, for pharmaceutical compositions prepared for administration once daily, a steady state individual is an individual to whom a pharmaceutical composition according to the present description has been administered once daily for a sufficient number of days in order to have arrived at steady state. Steady state is reached when the plasma concentration level after one dosing is the same within the standard deviation as the plasma concentration level after the next dosing, meaning for once daily dosing that $AUC_{(0-24h)d} = AUC_{(0-24h)d+1}$, and $C_{max(0-24h)d} = C_{max(0-24h)d+1}$ where "h" is hours and "d" is day. In certain embodiments, as described herein, a steady state individual, is an individual to whom the pharmaceutical compositions according to the present invention has been administered once daily for a period of time selected from, for example, at least 3 days, at least 4 days, and at least 7 days.

The term "trough" is defined as the average plasma concentration in a steady state individual just prior to the following dose. Thus, for pharmaceutical compositions prepared for continued administration of an active drug substance at intervals of about 20 to 28 hours (e.g., a 24 hour interval) between individual administrations, the trough is the average plasma concentration in a steady state individual 20 to 28 hours (e.g., a 24 hour interval) after dosing and just prior to the following dose. A steady state simulation may be calculated based on measurement of active drug substance or metabolites in serum after a single dose administration and based on such a simulation a theoretical trough may be determined. As exemplified herein, the trough may be determined as an average of the trough in at least 5 different individuals.

$AUC_{0-H}$ is defined by the average area under the curve of a plasma concentration profile of an active drug substance from 0-H after administration of said active drug substance, where "h" is hours. Thus, where "x"=12, the $AUC_{0-12h}$ is the average area under the curve of a plasma concentration profile of an active drug substance from 0-12 h after administration of said active drug substance. $AUC_{0-24h}$ is the average area under the curve of a plasma concentration profile of an active drug substance from 0-24 h after administration of said active drug substance. $AUC_{0-48h}$ is the average area under the curve of a plasma concentration profile of an active drug substance from 0-48 h after administration of said active drug substance. $AUC_{0-xh}$ is obtained from sum of steady state AUCs (I.e. $\Sigma(AUC_{0-1h}, AUC_{1-2h} \ldots AUC_{t-x})$) between measurements from each sample point. The AUCs are calculated by the linear trapezoidal method. If the last blood sample is taken at less than xh, for example, less than 24 h after drug administration, the xh value, such as the 24 h value will be extrapolated using the terminal elimination rate constant as described below. Single missing values will remain missing, i.e. corresponding to interpolation between the neighbouring points when calculating AUC. Similarly $AUC_{x-y}$ indicates the area under the curve of a plasma concentration profile of an active drug substance from x to y after administration of said active drug substance calculated in a similar manner.

The term "protraction index" as used herein illustrates the flatness of the steady state plasma concentration profile and is defined as the average concentration in the 24 hour dosing interval divided by the maximum concentration, i.e. $((AUC_{0-24h}/24\ h)/C_{max})$. In the theoretical case where the profile is completely flat the average concentration will be identical to the maximum concentration and the protraction index will be equal to 1. Hence, due to the fact that the average concentration cannot take a value higher than the maximum concentration, the protraction index can never be higher than 1. In cases where the profile is substantially flat, the difference between the maximum concentration and the average concentration is small and the protraction index will take a value close to 1. In other cases where the maximum concentration for instance is 5 times higher than the average concentration the protraction index will take the value 0.2.

Polyglycol

The formulations described herein are prepared as pharmaceutical compositions and, in specific embodiments, the pharmaceutical compositions described herein include a matrix composition comprising at least one polyglycol.

A matrix composition as described herein may comprise more than one different kind of polyglycol, such as 2, for example 3, such as 4, for example 5, such as more than 5 different polyglycols. In certain such embodiments, the matrix composition comprises 1 to 4 different polyglycols. In one such embodiment, the matrix composition comprises 1 to 3 different polyglycols. In another such embodiment, the matrix composition comprises 2 different polyglycols.

The polyglycol materials included in the pharmaceutical compositions described herein may, for example, be in the form of a homopolymer and/or a copolymer. If the matrix composition comprises more than one polyglycol they may all be different homopolymer, or different copolymers or a mixture of homopolymers and copolymers. In one embodiment, the matrix composition comprises at least one polyglycol, which is a homopolymer and at least one polyglycol, which is a copolymer. In another embodiment, the matrix composition comprises at least one polyglycol, which is a homopolymer.

The polyglycols included in the matrix compositions described herein may be selected from substantially water soluble, thermoplastic, crystalline, semi-crystalline or amorphous or a mixture of substantially water soluble, crystalline, semi-crystalline or amorphous polymers. In particular, in certain embodiments, the polyglycol is at least thermoplastic. Suitable polyglycols for use in a matrix composition according to the present description include, for example, polyethylene glycols, as well as derivatives of polyethylene glycol, such as mono or dimethoxypolyethylene glycols (mPEGs), polyethylene oxides and/or block copolymers of ethylene oxide and propylene oxide.

Polyethylene glycols (PEGs) are linear polydisperse polymers composed of repeating units of ethylene glycol. Their chemical formula is $HOCH_2[CH_2OCH_2]_mCH_2OH$, where m represents the average number of repeating units. Alternatively, the general formula $H[OCH_2CH_2]_nOH$ may be used to represent polyethylene glycol, where n is as number m in the previous formula +1. See the structural presentations of polyethylene glycol below, wherein n is the average number of oxyethylene groups, n equals m+1.

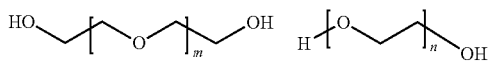

In specific embodiments, the matrix composition comprises at least one polyglycol which is a polyethylene oxide. Polyethylene oxides (PEOs) are linear polydisperse nonionic polymers composed of repeating units of ethylene oxide. Their chemical formula is $HO[CH_2CH_2O]_n$, where n represents the average number of oxyethylene groups. See the structural presentation of polyethylene oxide below, wherein n is the average number of oxyethylene groups. Depending on preparation method high molecular weight PEO may have one terminal methyl group.

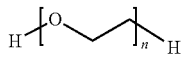

In general PEG refers to polymer chains with molecular weights below 20,000 daltons, while PEO refers to higher molecular weights polymers. However, because of the similarities between PEO and PEG, the terms are often used interchangeably for the same compound.

Polyethylene glycols and/or polyethylene oxides, which are suitable for use in the matrix composition are those having an average molecular weight of at least 20,000 daltons, such as an average molecular weight of in the range of 20,000 to 700,000 daltons, for example in the range of 20,000 to 600,000 daltons, such as in the range of 35,000 to 500,000 daltons, for example in the range of 35,000 to 400,000 daltons, such as in the range of 35,000 to 350,000 daltons, for example in the range of 50,000 to 350,000 daltons, such as in the range of 100,000 to 300,000 daltons, for example in the range of 150,000 to 350,000 daltons, such as in the range of 200,000 to 300,000 daltons. In certain embodiments, polyethylene glycols and/or polyethylene oxides suitable for use in the matrix compositions described herein are those having an average molecular weight selected from approximately 35,000 daltons, approximately 50,000 daltons, approximately 75,000 daltons, approximately 100,000 daltons, approximately 150,000 daltons, approximately 200,000 daltons, approximately 250,000 daltons, approximately 300,000 daltons, approximately 400,000 daltons, 150,000 daltons, 200,000 daltons, 250,000 daltons, 300,000 daltons, 400,000 daltons. In the present context, referring to the molecular weight of polyethylene glycols and polyethylene oxides, "approximately" means +/−30%.

In one embodiment, the matrix comprises only one polyethylene oxide, such as a PEO with an average molecular weight of in the range of approximately 50,000 to 500,000 daltons. In certain such embodiments the average molecular weight of the PEO may be selected from, for example, approximately 100,000 to 400,000 daltons, approximately 200,000 to 300,000 daltons, approximately 150,000 to 250,000 daltons, and approximately 200,000 daltons. This is in particular the case for pharmaceutical compositions, wherein the matrix has a length in a range selected from 7.5 to 15 mm, 8 to 15 mm, and 8 to 11 mm, and wherein said pharmaceutical composition is formulated for continued administration of an active drug substance for an interval of about 20 to about 28 hours between individual administrations.

In another embodiment of the invention the matrix comprises only one polyethylene oxide, preferably a PEO with an average molecular weight of in the range of 100,000 to 500,000 daltons, for example in the range of 200,000 to 400,000 daltons, such as in the range of 250,000 to 350,000 daltons, for example approximately 300,000 daltons, such as 300,000 daltons. This is in particular the case for pharmaceutical compositions according to the invention, wherein the matrix has a length of in the range of 7.5 to 15 mm, preferably a length of in the range of 7.5 to 10 mm, such as a length in the range of 7.5 to 8 mm, wherein said pharmaceutical composition is formulated for continued administration within the range of 20 to 28 hours interval between individual administrations.

In a specific embodiment, at least one polyglycol is a polyethylene oxide or a polyethylene glycol that has a molecular weight selected from approximately 20,000 daltons, approximately 35,000 daltons, approximately 50,000 daltons, approximately 100,000 daltons, approximately 200,000 daltons, approximately 300,000 daltons, and approximately 400,000 daltons. In the present context "approximately" means +/−30%. PEG is commercially available with average molecular weights up to 35,000 daltons. PEO is commercially available with average molecular weights up to 8,000,000 daltons. In specific embodiments, the polymer is a PEO having an average molecular weight of at least 100,000 daltons, such as in the range of 100,000 to 8,000,000 daltons, for example in the range of 100,000 to 7,000,000 daltons, such as in the range of 100,000 to 5,000,000 daltons, for example in the range of 100,000 to 4,000,000 daltons, such as in the range of 100,000 to 2,000,000 daltons, for example in the range of 100,000 to 1,000,000 daltons, such as in the range of 100,000 to 900,000 daltons. When PEO is employed with a molecular weight in the lower end, the PEO typically has a molecular weight as mentioned in the preceding paragraph. Commercially available PEOs with a molecular weight in the higher end typically exhibit a molecular weight selected from approximately 900,000 daltons, approximately 1,000,000 daltons, approximately 2,000,000 daltons, approximately 4,000,000 daltons, approximately 5,000,000 daltons, approximately 7,000,000 daltons, and approximately 8,000,000 daltons.

A matrix composition as described herein may also comprise at least one polyglycol which is a copolymer.

In some embodiments, the matrix composition comprises at least one polyglycol which is a poloxamer. Poloxamers are copolymers or block copolymers and are a range of non-ionic surfactants of polyethylene glycol (PEG) and polypropylene glycol (PPG).

The poloxamer may be Diol EO/PO block copolymers, which for example in chemical abstracts are described under the scientific name -hydroxy-hydroxypoly(oxyethylene)poly(oxypropylene)-poly(oxyethylene)-block copolymer in combination with the CAS register number. In specific embodiments, a suitable poloxamer for use in a composition of the invention has a HLB value of at least about 18 such as, for example, at least approximately 20, preferably at least 24. The average molecular weight of a suitable poloxamer is typically at least about 2,000 daltons.

Block copolymers of ethylene oxide and propylene oxide that may be included in the matrix compositions described herein have a molecular weight of at least 2,000 daltons, typically in the range of 3,000 to 30,000 daltons, such as in the range of 4,000 to 15,000 daltons.

Exemplary poloxamers that may be used in the matrix compositions according to the present description have the formula $HO(C_2H_4O)_a(C_3H_6O)_b(C_2H_4O)_aH$, where "a" is an integer from 10 to 150, such as from 30 to 140, for example from 50 to 100, such as from 65 to 90, for example from 70 to 90, and "b" is an integer from 10 to 80, such as from 15 to 80, for example from 20 to 60, such as from 25 to 55.

In one embodiment, the matrix comprises one or more copolymers, preferably one or more copolymers selected from the group consisting of poloxamers, such as poloxamer 188 and/or poloxamer 407. This is in particular the case for pharmaceutical compositions described herein, wherein the matrix has a length in a range selected from 7.5 to 15 mm and 8 to 10 mm, wherein said pharmaceutical composition is formulated for continued administration of an active drug substance over an interval of about 20 to about 28 hours between individual administrations.

In a specific embodiment, the matrix comprises at least two different copolymers selected from poloxamers, such as poloxamer 188 and poloxamer 407. In certain such embodiments, the pharmaceutical compositions include a matrix having a length in a range selected from a range of 8 to 15 mm and a range of 8 to 10 mm, and said pharmaceutical composition is formulated for continued administration of an active drug substance over and interval of about 20 to 28 hours between individual administrations.

In another specific embodiment, the matrix comprises a single poloxamer, such as poloxamer 188. In certain such embodiments, the pharmaceutical compositions include a matrix having a length in a range selected from a range of 7.5 to 15 mm and a range of 7.5 to 10 mm, and said pharmaceutical composition is formulated for continued administration of an active drug substance over and interval of about 20 to 28 hours between individual administrations.

The matrix compositions described herein may comprise mixtures of PEO with different average molecular weights, for example, in order to obtain a PEO with a desirable average molecular weight. The same applies to PEG.

Thus, in some embodiments, the matrix comprises two different PEO materials with different average molecular weights. In one such embodiment, a first PEO material may exhibit an average molecular weight in a range selected from approximately 150,000 to approximately 250,000 daltons, and approximately 200,000 daltons, while the second PEO material may exhibit an average molecular weight selected from approximately 250,000 to approximately 350,000 daltons, approximately 200,000 to approximately 300,000 daltons and approximately 300,000 daltons. In certain such embodiments, the pharmaceutical compositions include a matrix having a length in a range selected from a range of 7.5 to 15 mm and a range of 8 to 10 mm, and said pharmaceutical composition is formulated for continued administration of an active drug substance over an interval of about 20 to 28 hours between individual administrations.

It should be noted that, in this context, Vitamin E polyethylene glycol succinate (TPGS) is not considered a polyglycol.

The polyglycol used in the compositions described herein should have a melting point higher than the body temperature of the individual (e.g., a human) in which the composition is to be used. Thus, in particular embodiments, the polyglycol(s) employed in the matrix compositions described herein will suitably have a melting point of in the range of 38° C.-120° C., such as in the range of 38° C. to 100° C., for example in the range of 40° C. to 80° C.

In a specific embodiment, the matrix composition comprises at least one polyethylene oxide and at least one copolymer.

In addition to a polymer of a polyglycol type, the matrix composition may comprise an additional polymer, such as, for example, at least one polymer selected from: modified or unmodified water soluble natural polymers such as glucomannan, galactan, glucan, polygalacturonic acid, polyxylane, polygalactomannans, rhanogalacturonan, polyxyloglycan, arabinogalactan, and starch, cellulose, chitosan, alginate, fibrin, collagen, gelatin, hyaluronic acid, amylopectin, pectin including low methylated or methoxylated pectins, dextran and fatty acids and alcohols; synthetic polymers such as polyvinylpyrrolidone (PVP), PVA, PVB, Eudragit L methyl ester, Eudragit L, Eudragit RL, Eudragit RS, Eudragit E, Eudragit S, PHPV, PHA, PCL, PLGA and PLA; and hydrogels made from the polymers or combined polymers mentioned above and or from polymers originated from HEMA, HEEMA, MEMA, MEEMA, EDGMA, NVP, VAc, AA, acrylamide, MAA, HPMA, PEGA, PEGMA, PEGDMA, PEGDA, and PEGDMA.

One or more polymers are typically present in a matrix composition described herein in an amount of from 5 to 99.9% w/w, such as from 5 to 95% w/w, such as from 5 to 80% w/w, such as from 10 to 80% w/w, such as from 20 to 80% w/w, for example from 30 to 80% w/w, such as from 40 to 80% w/w, for example from 45 to 75% w/w.

In some embodiments, the total concentration of the polyglycols (notably the sum of homo- and copolymers of the polyglycol type) in the matrix composition may be from 5 to 99% w/w, such as from 15 to 95% w/w, for example from 30 to 90% w/w, such as from 30 to 85% w/w, for example from 30 to 80% w/w, such as from 40 to 80% w/w, for example from 45 to 75% w/w, such as from 40 to 50% w/w, for example from 45 to 50% w/w, such as from 60 to 85% w/w, for example from 60 to 80% w/w, for example from 70 to 75% w/w, such as from 71 to 75% w/w.

In some embodiments, the concentration of the polyglycol homopolymer in the matrix composition may be from 5 to 80% w/w, and in those cases where the homopolymer is the only thermoplastic polymer present in the matrix composition, then the concentration may be from 20 to 80 w/w, such as from 40 to about 80% w/w, such as for example from 70 to 80% w/w, such as from 70 to 75% w/w, for example from about 71 to about 75% w/w.

In certain embodiments, the concentration of the homopolymers in the matrix composition is in the range of 5 to 90% w/w, such as in the range of 20 to 85% w/w, for example in the range of 20 to 75% w/w, such as in the range of 20 to 70% w/w for example in the range of 20 to 40% w/w, such as in the range of 30 to 85% w/w, for example in the range of about 30 to 75% w/w, such as in the range of 30 to 60% w/w, for example in the range of 30 to 40% w/w, such as in the range of 30 to 35% w/w, such as in the range of 31 to about 33% w/w, such as in the range of 50 to 85% w/w, from 60 to 80% w/w, for example in the range of 70 to 80% w/w, for example in the range of 70 to 75% w/w, such as in the range of 71 to about 73% w/w.

The concentration of the polyglycol copolymer in the matrix composition, if present in combination with a polyglycol homopolymer, may be in the range of 0 to 60% w/w, such as for example 0 to 30% w/w. If the copolymer is the sole thermoplastic polymer in the matrix composition, the concentration may be from about 5 to about 99.5% w/w such as those ranges described above and described for the homopolymer.

In some embodiments, the concentration of polyglycols which are co-polymers in the matrix composition is in the range of 0 to 30% w/w, such as in the range of 1 to 20% w/w, for example in the range of 2 to 10% w/w, such as in the range of 2 to 5% w/w, such as in the range of 5 to 30% w/w, for example in the range of 5 to 20% w/w, for example in the range of 5 to 15% w/w, such as less than 15% w/w, for example less than 10% w/w, such as less than 5% w/w, such as less than 1% w/w, for example 0% w/w.

Active Drug Substance

An active drug substance suitable for use in the formulations and methods described herein is a therapeutically, prophylactically and/or diagnostically active drug substance (herein also abbreviated "active drug substance").

Examples of specific active drug substances suitable for use in the compositions and methods provided herein include:

Anti-inflammatory and antirheumatic active substances, such as, for example: Butylpyrazolidines, Phenylbutazone, Mofebutazone, Oxyphenbutazone, Clofezone, Kebuzone, Acetic acid derivatives and related substances, Indometacin, Sulindac, Tolmetin, Zomepirac, Diclofenac, Alclofenac, Bumadizone, Etodolac, Lonazolac, Fentiazac, Acemetacin, Difenpiramide, Oxametacin, Proglumetacin, Ketorolac, Aceclofenac, Bufexamac, Oxicams, Piroxicam, Tenoxicam, Droxicam, Lornoxicam, Meloxicam, Methotrexate, Propionic acid derivatives, Ibuprofen, Naproxen, Ketoprofen, Fenoprofen, Fenbufen, Benoxaprofen, Suprofen, Pirprofen, Flurbiprofen, Indoprofen, Tiaprofenic acid, Oxaprozin, Ibuproxam, Dexibuprofen, Flunoxaprofen, Alminoprofen, Dexketoprofen, Fenamates, Mefenamic acid, Tolfenamic acid, Flufenamic acid, Meclofenamic acid, Coxibs, Celecoxib, Rofecoxib, Valdecoxib, Parecoxib, Etoricoxib, Lumiracoxib, Nabumetone, Niflumic acid, Azapropazone, Glucosamine, Benzydamine, Glucosaminoglycan polysulfate, Proquazone, Orgotein, Nimesulide, Feprazone, Diacerein, Morniflumate, Tenidap, Oxaceprol, Chondroitin sulfate, Feprazone, Dipyrocetyl, Acetylsalicylic acid, Quinolines, Oxycinchophen, Gold preparations, Sodium aurothiomalate, Sodium aurotiosulfate, Auranofin, Aurothioglucose, Aurotioprol, Penicillamine and Bucillamine;

Analgesics, such as, for example: Opioids, Natural opium alkaloids, Morphine, Opium, Hydromorphone, Nicomorphine, Oxycodone, Dihydrocodeine, Diamorphine, Papavereturn, Codeine, Phenylpiperidine derivatives, Ketobemidone, Pethidine, Fentanyl, Diphenylpropylamine derivatives, Dextromoramide, Piritramide, Dextropropoxyphene, Bezitramide, Methadone, Benzomorphan derivatives, Pentazocine, Phenazocine, Oripavine derivatives, Buprenorphine, Morphinan derivatives, Butorphanol, Nalbuphine, Tilidine, Tramadol, Dezocine, Salicylic acid and derivatives, Acetylsalicylic acid, Aloxiprin, Choline salicylate, Sodium salicylate, Salicylamide, Salsalate, Ethenzamide, Morpholine salicylate, Dipyrocetyl, Benorilate, Diflunisal, Potassium salicylate, Guacetisal, Carbasalate calcium, Imidazole salicylate, Pyrazolones, Phenazone, Metamizole sodium, Aminophenazone, Propyphenazone, Nifenazone, Anilides, Paracetamol, Phenacetin, Bucetin, Propacetamol, Other analgesics and antipyretics, Rimazolium, Glafenine, Floctafenine, Viminol, Nefopam, Flupirtine, Ziconotide;

Anesthetics, such as, for example: Ethers, Diethyl ether, Vinyl ether, Halogenated hydrocarbons, Halothane, Chloroform, Methoxyflurane, Enflurane, Trichloroethylene, Isoflurane, Desflurane, Sevoflurane, Barbiturates, Methohexital, Hexobarbital, Thiopental, Narcobarbital, Opioid anaesthetics, Fentanyl, Alfentanil, Sufentanil, Phenoperidine, Anileridine, Remifentanil, Other general anaesthetics, Droperidol, Ketamine, Propanidid, Alfaxalone, Etomidate, Propofol, Hydroxybutyric acid, Nitrous oxide, Esketamine, Xenon, Esters of aminobenzoic acid, Metabutethamine, Procaine, Tetracaine, Chloroprocaine, Benzocaine, Amides, Bupivacaine, Lidocaine, Mepivacaine, Prilocalne, Butanilicaine, Cinchocaine, Etidocaine, Articaine, Ropivacaine, Levobupivacaine, Esters of benzoic acid, Cocaine, Other local anaesthetics, Ethyl chloride, Dyclonine, Phenol, Capsaicin;

Antimigraine active substances, such as, for example: Ergot alkaloids, Dihydroergotamine, Ergotamine, Methysergide, Lisuride, Corticosteroid derivatives, Flumedroxone, Selective serotonin (5HT1) agonists, Sumatriptan, Naratriptan, Zolmitriptan, Rizatriptan, Almotriptan, Eletriptan, Frovatriptan, Other antimigraine preparations, Pizotifen, Clonidine, Iprazochrome, Dimetotiazine, Oxetorone;

Antiepileptic active substances, such as, for example: Barbiturates and derivatives, Methylphenobarbital, Phenobarbital, Primidone, Barbexaclone, Metharbital, Hydantoin derivatives, Ethotoin, Phenyloin, Amino(diphenylhydantoin) valeric acid, Mephenyloin, Fosphenyloin, Oxazolidine derivatives, Paramethadione, Trimethadione, Ethadione, Succinimide derivatives, Ethosuximide, Phensuximide, Mesuximide, Benzodiazepine derivatives, Clonazepam, Carboxamide derivatives, Carbamazepine, Oxcarbazepine, Rufinamide, Fatty acid derivatives, Valproic acid, Valpromide, Aminobutyric acid, Vigabatrin, Progabide, Tiagabine, Other antiepileptics, Sultiame, Phenacemide, Lamotrigine, Felbamate, Topiramate, Gabapentin, Pheneturide, Levetiracetam, Zonisamide, Pregabalin, Stiripentol, Lacosamide, Beclamide;

Anticholinergic active substances, such as, for example: Tertiary amines, Trihexyphenidyl, Biperiden, Metixene, Procyclidine, Profenamine, Dexetimide, Phenglutarimide, Mazaticol, Bornaprine, Tropatepine, Ethers chemically close to antihistamines, Etanautine, Orphenadrine (chloride), Ethers of tropine or tropine derivatives, Benzatropine, Etybenzatropine;

Dopaminergic active substances, such as, for example: Dopa and dopa derivatives, Levodopa, Melevodopa, Etilevodopa, Adamantane derivatives, Amantadine, Dopamine agonists, Bromocriptine, Pergolide, Dihydroergocryptine mesylate, Ropinirole, Pramipexole, Cabergoline, Apomorphine, Piribedil, Rotigotine, Monoamine, oxidase B inhibitors, Selegiline, Rasagiline, Other dopaminergic agents, Tolcapone, Entacapone, Budipine;

Antipsychotic active substances, such as, for example: Phenothiazines with aliphatic side-chain, Chlorpromazine, Levomepromazine, Promazine, Acepromazine, Triflupromazine, Cyamemazine, Chlorproethazine, Phenothiazines with piperazine structure, Dixyrazine, Fluphenazine, Perphenazine, Prochlorperazine, Thiopropazate, Trifluoperazine, Acetophenazine, Thioproperazine, Butaperazine, Perazine, Phenothiazines with piperidine structure, Periciazine, Thioridazine, Mesoridazine, Pipotiazine, Butyrophenone derivatives, Haloperidol, Trifluperidol, Melperone, Moperone, Pipamperone, Bromperidol, Benperidol, Droperidol, Fluanisone, Indole derivatives, Oxypertine, Molindone, Sertindole, Ziprasidone, Thioxanthene derivatives, Flupentixol, Clopenthixol, Chlorprothixene, Tiotixene, Zuclopenthixol, Diphenylbutylpiperidine derivatives, Fluspirilene, Pimozide, Penfluridol, Diazepines, oxazepines and thiazepines, Loxapine, Clozapine, Olanzapine, Quetiapine, Neuroleptics, in tardive dyskinesia, Tetrabenazine, Benzamides, Sulpiride, Sultopride, Tiapride, Remoxipride, Amisulpride, Veralipride, Levosulpiride, Lithium, Other antipsychotics, Prothipendyl, Risperidone, Clotiapine, Mosapramine, Zotepine, Aripiprazole, Paliperidone;

Anxiolytic active substances, such as, for example: Benzodiazepine derivatives, Diazepam, Chlordiazepoxide, Medazepam, Oxazepam, Potassium clorazepate, Lorazepam, Adinazolam, Bromazepam, Clobazam, Ketazolam, Prazepam, Alprazolam, Halazepam, Pinazepam, Camazepam, Nordazepam, Fludiazepam, Ethyl loflazepate, Etizolam, Clotiazepam, Cloxazolam, Tofisopam, Diphenylmethane derivatives, Hydroxyzine, Captodiame, Carbamates, Meprobamate, Emylcamate, Mebutamate, Dibenzo-bicyclo-octadiene derivatives, Benzoctamine, Azaspirodecanedione derivatives, Buspirone, Other anxiolytics, Mephenoxalone, Gedocarnil, Etifoxine;

Hypnotic and sedative active substances, such as, for example: Barbiturates, Pentobarbital, Amobarbital, Butobarbital, Barbital, Aprobarbital, Secobarbital, Talbutal, Vinylbital, Vinbarbital, Cyclobarbital, Heptabarbital, Reposal, Methohexital, Hexobarbital, Thiopental, Etallobarbital, Allobarbital, Proxibarbal, Aldehydes and derivatives, Chloral hydrate, Chloralodol, Acetylglycinamide chloral hydrate, Dichloralphenazone, Paraldehyde, Benzodiazepineemepronium derivatives, Flurazepam, Nitrazepam, Flunitrazepam, Estazolam, Triazolam, Lormetazepam, Temazepam, Midazolam, Brotizolam, Quazepam, Loprazolam, Doxefazepam, Cinolazepam, Piperidinedione derivatives, Glutethimide, Methyprylon, Pyrithyldione, Benzodiazepine related drugs, Zopiclone, Zolpidem, Zaleplon, Ramelteon, Other hypnotics and sedatives, Methaqualone, Clomethiazole, Bromisoval, Carbromal, Scopolamine, Propiomazine, Triclofos, Ethchlorvynol, Valerian, Hexapropymate, Bromides, Apronal, Valnoctamide, Methylpentynol, Niaprazine, Melatonin, Dexmedetomidine, Dipiperonylaminoethanol;

Antidepressant active substances, such as, for example: Non-selective monoamine reuptake inhibitors, Desipramine, Imipramine, Imipramine oxide, Clomipramine, Opipramol, Trimipramine, Lofepramine, Dibenzepin, Amitriptyline, Nortriptyline, Protriptyline, Doxepin, Iprindole, Melitracen, Butriptyline, Dosulepin, Amoxapine, Dimetacrine, Amineptine, Maprotiline, Quinupramine, Selective serotonin reuptake inhibitors, Zimeldine, Fluoxetine, Citalopram, Paroxetine, Sertraline, Alaproclate, Fluvoxamine, Etoperidone, Escitalopram, Monoamine oxidase inhibitors, non-selective, Isocarboxazid, Nialamide, Phenelzine, Tranylcypromine, Iproniazide, Iproclozide, Monoamine oxidase A inhibitors, Moclobemide, Toloxatone, Other antidepressants, Oxitriptan, Tryptophan, Mianserin, Nomifensine, Trazodone, Nefazodone, Minaprine, Bifemelane, Viloxazine, Oxaflozane, Mirtazapine, Medifoxamine, Tianeptine, Pivagabine, Venlafaxine, Milnacipran, Reboxetine, Gepirone, Duloxetine, Agomelatine, Desvenlafaxine, Centrally acting sympathomimetics, Amfetamine, Dexamfetamine, Lisdexamfetamine, Metamfetamine, Methylphenidate, Dexmethylphenidate, Pemoline, Fencamfamin, Modafinil, Fenozolone, Atomoxetine, Fenetylline, Xanthine derivatives, Caffeine, Propentofylline, Other psychostimulants and nootropics, Meclofenoxate, Pyritinol, Piracetam, Deanol, Fipexide, Citicoline, Oxiracetam, Pirisudanol, Linopirdine, Nizofenone, Aniracetam, Acetylcarnitine, Idebenone, Prolintane, Pipradrol, Pramiracetam, Adrafinil, Vinpocetine;

Anti-dementia active substances, such as, for example: Anticholinesterases, Tacrine, Donepezil, Rivastigmine, Galantamine, Other anti-dementia drugs, Memantine, Ginkgo biloba;

Other nervous system active substances, such as, for example: Parasympathomimetics, Anticholinesterases, Neostigmine, Pyridostigmine, Distigmine, Ambenonium, Choline esters, Carbachol, Bethanechol, Other parasympathomimetics, Pilocarpine, Choline alfoscerate;

Active substances used in addictive disorders, such as, for example: Nicotine, Bupropion, Varenicline, Disulfuram, Calcium carbimide, Acamprosate, Naltrexone, Buprenorphine, Methadone, Levacetylmethadol, Lofexidine, Betahistine, Cinnarizine, Flunarizine, Acetylleucine, Gangliosides and ganglioside derivatives, Tirilazad, Riluzole, Xaliproden, Hydroxybutyric acid, Amifampridine; and Opium alkaloids and derivatives, such as, for example: Ethylmorphine, Hydrocodone, Codeine, Opium alkaloids with morphine, Normethadone, Noscapine, Pholcodine, Dextromethorphan, Thebacon, Dimemorfan, Acetyldihydrocodeine, Benzonatate, Benproperine, Clobutinol, Isoaminile, Pentoxyverine, Oxolamine, Oxeladin, Clofedanol, Pipazetate, Bibenzonium bromide, Butamirate, Fedrilate, Zipeprol, Dibunate, Droxypropine, Prenoxdiazine, Dropropizine, Cloperastine, Meprotixol, Piperidione, Tipepidine, Morclofone, Nepinalone, Levodropropizine, Dimethoxanate.

In certain embodiments, the active drug substance may, for example, be an active drug substance with abuse potential that presents a safety risk. Such active drug substance may, for example, be selected from:

1-(1-Phenylcyclohexyl)pyrrolidine, 1-(2-Phenylethyl)-4-phenyl-4-acetoxypiperidine, 1-[1-(2-Thienyl)-cyclohexyl]piperidine, 1-[1-(2-Thienyl)cyclohexyl]pyrrolidine, 1-Methyl-4-phenyl-4-propionoxy-piperidine, 1-Phenylcyclohexylamine, 1-Piperidinocyclohexanecarbonitrile, 2,5-Dimethoxy-4-ethylamphetamine, 2,5-Dimethoxyamphetamine, 2C-B-(4-bromo-2,5-dimethoxypenethylamine), 2C-D (2,5-dimethoxy-4-methylphenethylamine), 2C-I (4-iodo-2,5-dimethoxyphenethylamine), 2C-T-2 (2,5-dimethoxy-4-ethylthiophenethylamine), 2C-T-4 (2,5-dimethoxy-4-isopropyl thiophenethylamine), 2C-T-7 (2,5-dimethoxy-4-(n)-propylthiopenethylamine), 3,4-Methylenedioxymethamphetamine, 3,4,5-Trimethoxyamphetamine, 3,4-Methylenedioxyamphetamine, 3,4-Methylenedioxy-N-ethylamphetamine, 3-Methylfentanyl, 3-Methylthiofentanyl, 4-Brorno-2,5-dimethoxyamphetamine, 4-Bromo-2,5-dimethoxyphenethylamine, 4-Methoxyamphetamine, 4-Methyl-2,5-dimethoxyamphetamine, 4-Methylaminorex (cis isomer), 5-MeO-DIPT (5-Methoxy-N,N-diisopropyltryptamine), 5-MeO-DMT (5-Methoxy-N,N-dimethyltryptamine), 5-Methoxy-3,4-methylenedioxyamphetamine, Acetorphin, Acetorphine, Acetyl-alpha-methylfentanyl, Acetyl-alpha-methylfentanyl, Acetyldihydrocodeine, Acetylmethadol, Acetylmethadol, Alfentanil, Allobarbital, Allylprodin, Allylprodine, Alphacetylmethadol except levo-alphacetylmethadol, Alpha-ethyltryptamine, Alphameprodine, Alphamethadol, Alphamethadol, Alpha-Methylfentanyl, Alpha-Methylthiofentanyl, Alphaprodine, Alprazolam, Amfepramon, Amfetaminil, Amineptin, Aminorex, Amobarbital, Amphetamine, Dextroamphetamine, AmyInitrit (all isomers of the amyl group), Anabolic steroids, Anileridine, Aprobarbital, Barbital, Barbituric acid derivative, BDB (3,4- methylenedioxyphenyl)-2-butanamine), Benzethidin, Benzethidine, Benzoylecgonine, Benzphetamine, Benzphetamine, Benzylmethylketon, Benzyl morphine, Betacetylmethadol, Beta-Hydroxy-3-methylfentanyl, Beta-Hydroxyfentanyl, Betameprodine, Betameprodine, Betamethadol, Betaprodine, Bezitramide, Bezitramide, Boldenone, Brolamfetamin, Bromazepam, Brotizolam, Bufotenine, Buprenorphine, Butabarbital, Butalbital, Butobarbital, Butorphanol, BZP (A 2)(1-benzylpiperazin), Camazepam, Cannabis, Carfentanil, Catha edulis, Cathine, Cathinone, Chloral betaine, Chloral hydrate, Chlordiazepoxide, Chlorhexadol, Chlorotestosterone (same as clostebol), Chlorphentermine, Clobazam, Clonazepam, Clonitazene, Clonitazene, Clorazepate, Clortermine, Clostebol, Clotiazepam, Cloxazolam, Coca Leaves, Cocaine, Codeine, Codeine & isoquinoline alkaloid, Codeine methylbromide, Codeine-N-oxide, Codoxim, Cyclobarbital (Hexemal NFN), Cyprenorphine, Dehydrochlormethyltestosterone, Delorazepam, Desomorphine, Dexamfetamine, Dexfenfluramine, Dexmethylphenidate, Dextromoramide, Dextropropoxyphene, Diacetylmorphine, Diampromide, Diazepam, Dichloralphenazone, Diethylpropion, Diethylthiambutene, Diethyltryptamine, Difenoxin, Dihydrocodeine, Dihydroetorphine, Dihydromorphine, Dihydrotestosterone, Dimenoxadol, Dimepheptanol, Dimethylthiambutene, Dimethyltryptamine, Dioxaphetyl butyrate, Diphenoxylate, Dipipanone, Diprenorphine, Dronabinol, Drostanolone, Drotebanol, Ecgonine, Estazolam, Ethchlorvynol, Ethinamate, Ethyl loflazepate, Ethylestrenol, Ethylmethylthiambutene, Ethylmorphine, Ethylmorphine, Eticyclidin, Etilamfetamine, Etonitazene, Etorphine, Etoxeridine, Etryptamine, Fencamfamin, Fenethylline, Fenetylline, Fenfluramine, Fenproporex, Fentanyl, Fludiazepam, Flunitrazepam, Fluoxymesterone, Flurazepam, Formebolone, Fungi and Spores of the species Psilocype Semilanceata, Furethidine, Gammahydroxybutanic acid, Glutethimide, Halazepam, Haloxazolam, Heroine, Hydrocodone, Hydrocodone & isoquinoline alkaloid, Hydromorphinol, Hydromorphone, Hydroxypethidine, Ibogaine, Isobutylnitrit, Isomethadone, Ketamine, Ketazolam, Ketobemidone, Levamfetamine, Levo-alphacetylmethadol, Levo-methamphetamine, Levomethorphan, Levomoramide, Levophenacylmorphan, Levorphanol, Lisdexamfetamin, Loprazolam, Lorazepam, Lormetazepam, Lysergic acid, Lysergic acid amide, Lysergic acid diethylamide, Marijuana, Mazindol, MBDN (N-methyl-1-(3,4-methylenedioxyphenyl)-2-butanamine), mCPP (1-(3-chlorphenyl)piperazine), Mebutamate, Mecloqualone, Medazepam, Mefenorex, MeOPP (1-(4-methoxyphenyl)piperazine), Meperidine, Meperidine intermediate, Meprobamate, Mescaline, Mesocarb, Mesterolone, Metamfetamine, Metazocine, Methadone, Methadone intermediate, Methamphetamine, Methandienone, Methandranone, Methandriol, Methandrostenolone, Methaqualone, Methcathinone, Methenolone, Methohexital, Methyldesorphine, Methyldihydromorphine, Methylphenidate, Methylphenobarbital (mephobarbital), Methyltestosterone, Methyprylone, Metopone, Mibolerone, Midazolam, Modafinil, Moramide-intermediate, Morpheridine, Morphine, Morphine methylbromide, Morphine methylsulfonate, Morphine-N-oxide, Myrophine, N,N-Dimethylamphetamine, Nabilone, Nalorphine, Nandrolone, N-Ethyl-1-phenylcyclohexylamine, N-Ethyl-3-piperidyl benzilate, N-Ethylamphetamine, N-Hydroxy-3,4-methylenedioxyamphetamine, Nicocodeine, Nicocodine, Nicodicodine, Nicomorphine, Nimetazepam, Nitrazepam, N-Methyl-3-piperidyl benzilate, Noracymethadol, Norcodeine, Nordiazepam, Norethandrolone, Norlevorphanol, Normethadone, Normorphine, Norpipanone, Norpipanone, Opium, Oxandrolone, Oxazepam, Oxazolam, Oxycodone, Oxymesterone, Oxymetholone, Oxymorphone, Para-Fluorofentanyl, Parahexyl, Paraldehyde, Pemoline, Pentazocine, Pentobarbital, Petrichloral, Peyote, Phenadoxone, Phenampromide, Phenazocine, Phencyclidine, Phendimetrazine, Phenmetrazine, Phenobarbital, Phenomorphan, Phenoperidine, Phentermine, Phenylacetone, Pholcodine, Piminodine, Pinazepam, Pipradrole, Piritramide, PMMA (paramethyxymethyl amphetamine), Prazepam, Proheptazine, Properidine, Propiram, Psilocybine, Psilocyn, Pyrovalerone, Quazepam, Racemethorphane, Racemoramide, Racemorphane, Remifentanil, Salvia divinorum, Salvinorin A, Secobarbital, Secobarbital, Sibutramine, SPA, Stanolone, Stanozolol, Sufentanil, Sulfondiethylmethane, Sulfonethylmethane, Sulfonmethane, Talbutal, Temazepam, Tenamfetamin, Testolactone, Testosterone, Tetrahydrocannabinols, Tetrazepam, TFMPP (1-(3-triflourmethylphenyl) piperazine), Thebacon, Thebaine, Thiamylal, Thiofentanyl, Thiopental, Tiletamine & Zolazepam in Combination, Tilidine, Trenbolone, Triazolam, Trimeperidine, Vinbarbital, Zaleplon, Zipeprol, Zolpidem and Zopiclon.

Other suitable examples of active drug substances suitable for use in the pharmaceutical compositions described herein include, for example, alfentanil, allylprodine, alphaprodine, aniloridine, benzylmorphine, bezitramide, buprenorphine, butophanol, clonitazene, codeine, cyclazocine, desomorphine, dextromoramide, dezocine, diapromide, dihydrocodeine, dihydromorphine, dimenoxadol, dimephetanol, dimethylthiambutene, dioxaphetyl butyrate, dipipanone, eptazocine, ethoheptazine, ethylmethylthiambutene, ethylmorphine, etonitazene, fentanyl, heroin, hydrocodone, hydromorphone, hydroxypethidine, isomethadone, dextropropoxyphene, ketobemidone, levallorphan, levorphanol, levophenacylmorphan, lofentanil, meperidine, meptazinol, metazocine, methadone, metopon, morphine, morphine 6-glucuronide, morphine 3-glucuronide, myrophine, nalbuphine, narccine, nicomorphine, norlevorphanol, normethadone, nalorphine, normorphine, norpipanone, opium, oxycodone, oxycodeine, oxymorphone, papavereturn, pentazocine, phenadoxone, phenomorphan, phenazocine, phenoperidine, piminodine, piritramide, propheptazine, promedol, properidine, propiram, propoxyphene, sufentanil, tilidine, tramadol, thebaine, levo-alphacetylmethadol (LAAM), remifentanil, carfentanyl, ohmefentanyl, MPPP, prodine, PEPAP, levomethorphan, etorphine, lefetamine, loperamide, diphenoxylate or pethidine.

Even further examples of active drug substances suitable for use in the pharmaceutical compositions described herein include anabolic steroids, cannabis, cocaine and diazepam.

In one embodiment, the active substance is selected from the group consisting of the therapeutic classes including non-steroidal anti-inflammatory substances and antirheumatic active substances.

In other embodiments, the active substance is selected from therapeutic classes including analgesics, opioids, antipyretics, anaesthetics, antimigraine agents, antiepileptics, anti-parkinson agents, dopaminergic agents, antipsychotics, anxiolytics, sedatives, antidepressants, psychostimulants agents, dopamine, noradrenaline, nicotinic, alfa-andrenergic, serotonin, $H_3$ antagonists used for ADHD and nootropics agents used in addictive disorders.

In still further embodiments, the active substance is selected from therapeutic classes including anaesthetics, centrally-acting analgesics, sedative-hypnotics, anxiolytics, appetite suppressants, decongestants, antitussives, antihistamines, antiemetics, antidiarrheals, and drugs used to treat narcolepsy and attention deficit hyperactivity disorder.

In certain embodiments, the active drug substance is associated with abuse syndromes and the active drug substance may, for example, be selected from opioids, CNS depressants, CNS stimulants, cannabinoids, nicotine-like compounds, glutamate antagonists and N-methyl-D-aspartate (NMDA) antagonists.

In specific embodiments, the active drug substance is an analgesic. Examples of analgesics suitable for use in the pharmaceutical compositions and methods described herein include, for example, Opioids, Natural opium alkaloids, Morphine, Opium, Hydromorphone, Nicomorphine, Oxycodone, Dihydrocodeine, Diamorphine, Papavereturn, Codeine, Phenylpiperidine derivatives, Ketobemidone, Pethidine, Fentanyl, Diphenylpropylamine derivatives, Dextromoramide, Piritramide, Dextropropoxyphene, Bezitramide, Methadone, Benzomorphan derivatives, Pentazocine, Phenazocine, Oripavine derivatives, Buprenorphine, Morphinan derivatives, Butorphanol, Nalbuphine, Tilidine, Tramadol, Dezocine, Salicylic acid and derivatives, Acetylsalicylic acid, Aloxiprin, Choline salicylate, Sodium salicylate, Salicylamide, Salsalate, Ethenzamide, Morpholine salicylate, Dipyrocetyl, Benorilate, Diflunisal, Potassium salicylate, Guacetisal, Carbasalate calcium, Imidazole salicylate, Pyrazolones, Phenazone, Metamizole sodium, Aminophenazone, Propyphenazone, Nifenazone, Anilides, Paracetamol, Phenacetin, Bucetin, Propacetamol, Other analgesics and antipyretics, Rimazolium, Glafenine, Floctafenine, Viminol, Nefopam, Flupirtine, Ziconotide.

In certain such embodiments, the active drug substance is an opioid. Where an opioid is included as an active drug substance, the opioid may be selected from naturally occurring opioids, synthetic opioids and semisynthetic opioids.

In another embodiment, the active drug substance is selected from Amfetamine, Dexamfetamine, Lisdexamfetamine, Metamfetamine, Methylphenidate, Dexmethylphenidate and combinations thereof.

In some embodiments of pharmaceutical compositions including an opioid, the opioid is selected from buprenorphine, codeine, dextromoramide, dihydrocodeine, fentanyl, hydrocodone, hydromorphone, morphine, pentazocine, oxycodeine, oxycodone, oxymorphone, norhydrocodone, noroxycodone, morphine-6-glucuronode, tramadol and dihydromorphine.

Where an opioid is used as an active drug substance, the opioid, such as morphine, hydrocodone, hydromorphone or oxycodone, may be present in any of its crystalline, polymorphous, or amorphous forms. Furthermore, an opioid used as an active drug substance may be present in one or more forms selected its crystalline, polymorphous, or amorphous forms.

In specific embodiments of the pharmaceutical compositions including an opioid as an active drug substance, the active drug substance is selected from morphine, oxycodone, hydrocodone, hydromorphone, norhydrocodone, oxymorphone, noroxycodone, morphine-6-glucuronode and pharmaceutically acceptable salts of any of the aforementioned, such as from the group consisting of oxycodone hydrochloride, hydrocodone bitartrate, hydromorphone hydrochloride and morphine sulphate pentahydrate.

All of the above mentioned active drug substances may also be in the form of pharmaceutically acceptable salts, uncharged or charged molecules, molecular complexes, solvates or anhydrates thereof, and, if relevant, isomers, enantiomers, racemic mixtures, and mixtures thereof.

In particular, the pharmaceutical compositions described herein may comprise pharmaceutically acceptable salts of any of the above mentioned active drug substances.

The term "pharmaceutically acceptable salts" of an active drug substance includes alkali metal salts such as, for example, sodium or potassium salts, alkaline earth metal salts such as, for example, calcium and magnesium salts, and salts with organic or inorganic acid like, for example, hydrochloric acid, hydrobromic acid, nitric acid, sulfuric acid, phosphoric acid, citric acid, formic acid, maleic acid, succinic acid, tartaric acid, methansulphonic acid, toluenesulphonic acid etc.

The term "pharmaceutically acceptable salts" of an opioid includes alkali metal salts such as, for example, sodium or potassium salts, alkaline earth metal salts such as, e.g., calcium and magnesium salts, and salts with organic or inorganic acids like e.g. hydrochloric acid, hydrobromic acid, nitric acid, sulfuric acid, phosphoric acid, citric acid, formic acid, maleic acid, succinic acid, tartaric acid, methansulphonic acid, toluenesulphonic acid etc or tartrate acid. In particular embodiments, pharmaceutically acceptable opioid salts may be selected from the group consisting of sulphate salts, hydrochloride salts and bitartrate salts.

The term "solvates" includes hydrates or solvates wherein other solvates than water are involved such as, for example, organic solvents like chloroform and the like.

Furthermore, the active drug substance may be in any of its crystalline, polymorphous, semi-crystalline, amorphous or polyamorphous forms and mixtures thereof.

The concentration of the active drug substance in a composition for use according to the invention depends on the specific active drug substance, the disease to be treated, the condition of the patient, the age and gender of the patient etc. The above-mentioned active drug substances are well-known active drug substances and a person skilled in the art will be able to find information as to the dosage of each active drug substance and, accordingly, he will know how to determine the amount of each active drug substance in a composition. The active drug substance is typically present in a matrix composition of the invention in a concentration amount of from 0.01-99% w/w such as, for example, from about 0.01 to about 90% w/w, from about 0.01 to about 80% w/w, from about 0.01 to about 70% w/w, from about 0.01 to about 50% w/w, from about 0.01 to about 45% w/w or from about 0.01 to about 40% w/w.

When the active drug substance is an opioid, such as morphine, oxycodone, hydromorphone or hydrocodone or salts thereof, then said opioid is typically present in the matrix compositions in a concentration of in the range of 1 to 70% w/w, for example in the range of 1 to 60% w/w, such as in the range of 1 to 50% w/w, such as in the range of 1 to 45% w/w, for example in the range of 1 to 40% w/w, such as in the range of 1 to 30% w/w, for example in the range of 1 to 20% w/w, such as in the range of 1 to 17% w/w.

When the active drug substance is an opioid, such as morphine or salts thereof, then said opioid is typically present in the matrix compositions in a concentration of in the range of 1 to 70% w/w, for example in the range of 1 to 60% w/w, such as in the range of 1 to 55% w/w, for example in the range of 1 to 50% w/w, such as in the range of 1 to 40% w/w, for example in the range of 1 to 35% w/w, such as in the range of 1 to 30% w/w, for example in the range of 1 to 20% w/w, such as in the range of 1 to 17% w/w, or the opioid, such as morphine, may be present in the matrix in the range of 5 to 60% w/w, for example in the range of 20 to 60% w/w, such as in the range of 30 to 60% w/w, for example in the range of 30 to 55% w/w, such as in the range of 35 to 55% w/w.

In one embodiment, the matrix composition comprises an opioid active drug substance in an amount ranging from 1 to 17% w/w, such as 10 to 17% w/w, for example 15 to 17% w/w, such as 16% w/w. In one such embodiment, the opioid is selected from morphine and pharmaceutically acceptable salts thereof. In other embodiments including an opioid as an active agent, the matrix composition includes the opioid active drug substance in an amount greater than 17% w/w, such as in the range of 20 to 60% w/w, and in one such embodiment, the opioid drug substance is selected from morphine and pharmaceutically acceptable salts thereof.

In another embodiment, the matrix composition comprises an opioid active drug substance in an amount ranging from 1 to 70% w/w, for example in the range of 1 to 60% w/w, such as in the range of 1 to 50% w/w, for example in the range of 1 to 45% w/w, such as in the range of 1 to 40% w/w, such as in the range of 1 to 30% w/w, for example in the range of 5 to 20% w/w, such as in the range of 10 to 20% w/w, for example in the range of 12 to 15% w/w. In certain such embodiments, the opioid active agent is hydrocodone bitartrate.

In another embodiment, the matrix composition comprises a high load of an opioid active drug substance, wherein a high load is at least 15% w/w, preferably in the range of 15 to 70% w/w, for example in the range of 15 to 60% w/w, such as in the range of 15 to 50% w/w, for example in the range of 15 to 45% w/w, such as in the range of 15 to 40% w/w, such as in the range of 15 to 30% w/w, for example in the range of 20 to 30% w/w, such as in the range of 24 to 28% w/w. In certain such embodiments, the opioid active agent is hydrocodone bitartrate.

In yet another embodiment, the matrix composition comprises oxycodone hydrochloride as an opioid active drug substance. In certain such embodiments, the matrix composition includes oxycodone hydrochloride in an amount ranging from 1 to 70% w/w, for example in the range of 1 to 60% w/w, such as in the range of 1 to 50% w/w, for example in the range of 1 to 45% w/w, such as in the range of 1 to 40% w/w, such as in the range of 1 to 30% w/w, for example at least 15% w/w, preferably in the range of 15 to 70% w/w, for example in the range of 15 to 60% w/w, such as in the range of 15 to 50% w/w, such as in the range of 15 to 45% w/w, for example in the range of 15 to 40% w/w, such as in the range of 15 to 30% w/w, for example in the range of 20 to 30% w/w, such as in the range of 24 to 28% w/w.

In certain embodiments, the matrix compositions comprise a low load of the active drug substance, such as an opioid. A low load is generally less than 50% w/w of the active drug substance. For example, in certain such embodiments, the matrix compositions may include an active drug substance in an amount selected from less than 45% w/w and less than 40% w/w.

A pharmaceutical composition according to the invention containing an active drug substance as described herein above is typically formulated for oral administration. In one embodiment, the matrix composition provides for administration only once daily. In particular such embodiments, for the pharmaceutical composition a length of in the range of 7.5 to 15 mm, preferably 8 to 15 mm, more preferably 8 to 10 mm. The matrix composition may also provide for administration twice daily, which in particular is the case for the pharmaceutical composition exhibits a length shorter than 8 mm, such as a length in a range selected from 4 to 8 mm, 5.5 to 8 mm, or 5.8 to 8 mm.

Certain active drug substances may be subject to entero-hepatic recirculation. Thus, for example, morphine, hydromorphone and other opioids are metabolised mainly in the liver to both active and inactive compounds that are excreted in urine and bile. Morphine and hydromorphone are excreted partly in the bile as water-soluble glucuronides. In the gut, these glucuronides are metabolised by the normal gut flora to the parent opioid compound and reabsorbed (entero-hepatic recirculation), which may prolong the residence of morphine and hydromorphone and theirs metabolites in the systemic circulation.

Pharmaceutical compositions comprising active drug substances subject to entero-hepatic recirculation may in general be shorter than other pharmaceutical compositions. Thus, pharmaceutical compositions comprising active drug substances subject to entero-hepatic recirculation (e.g., morphine, hydromorphone or pharmaceutically acceptable salts thereof) may have a length of in a range selected from 7.5 to 15 mm, 7.5 to 10 mm, 7.5 to 8 mm long, even when the pharmaceutical composition is prepared for continued administration of an active drug substance over an interval of about 22 to about 28 hours, such as 24 hours between individual administrations. In certain such embodiments, pharmaceutical composition is prepared to exhibit a length of 7.5 mm.

Neither Hydrocodone nor Oxycodone are metabolized by glucuronidation in the liver, but are primarily demethylated via CYP pathways. Nevertheless, pharmaceutical compositions as disclosed herein that include hydrocodone or oxycodone as an active drug substance are useful for providing continued administration of the active drug substance over an interval of about 20 to 28 hours (such a 24 hour interval) between individual administrations.

Pharmaceutical compositions comprising active drug substances which are essentially not subject to entero-hepatic recirculation, in general, may be longer than other pharmaceutical compositions. Thus, pharmaceutical compositions comprising active drug substances which are not subject to entero-hepatic recirculation (e.g., oxycodone or hydrocodone or pharmaceutically acceptable salts thereof) may have a length in a range selected from 8 to 15 mm, 8 to 12 mm, and 8 to 10 mm, when the pharmaceutical composition is prepared for continued administration of the active drug substance over an interval of about 22 to 28 hours, such as a 24 hour interval, between individual administrations.

A pharmaceutical composition as described herein may comprise one active drug substance or more than one different active drug substances. Typically, the amount of the active substance corresponds to a daily or part of a daily therapeutic dose.

Pharmaceutical compositions as described herein are suitable for use for both water soluble as well as slightly soluble or insoluble active substances.

Pharmaceutically Acceptable Excipients

The matrix composition of the formulations described herein may also contain other excipients in order to achieve the one or more desired properties, such as a stability of the active drug substance or the pharmaceutical composition itself, loading of the active drug substance or delivery characteristics, such as release rate or release profile of an active drug substance. Further, a matrix composition may include excipients that facilitate manufacture and production of dosage forms suitable for administration to individuals in need thereof.

A suitable pharmaceutically acceptable excipient for use in a matrix composition of the invention may be selected from fillers, diluents, disintegrants, glidants, pH-adjusting agents, viscosity adjusting agents, solubility increasing or decreasing agents, osmotically active agents and solvents.

Suitable excipients include conventional tablet or capsule excipients. These excipients may be, for example, diluents such as dicalcium phosphate, calcium sulfate, lactose or sucrose or other disaccharides, cellulose, cellulose derivatives, kaolin, mannitol, dry starch, glucose or other monosaccharides, dextrin or other polysaccharides, sorbitol, inositol or mixtures thereof; binders such as alginic acid, calcium alginate, sodium alginate, starch, gelatin, saccharides (including glucose, sucrose, dextrose and lactose), molasses, panwar gum, ghatti gum, mucilage of isapol husk, carboxymethylcellulose, methylcellulose, veegum, larch arabolactan, polyethylene glycols, ethylcellulose, water, alcohols, waxes, polyvinylpyrrolidone such as PVP K90 or mixtures thereof; lubricants such as talc, silicium dioxide, magnesium stearate, calcium stearate, stearic acid, hydrogenated vegetable oils, sodium benzoate, sodium chloride, leucine, carbowax 4000, magnesium lauryl sulfate, Sodium laurilsulfate, Stearyl alcohol, Polysorbate 20, Polysorbate 60, Polysorbate 80, Macrogol stearate, Macrogol lauryl ether, Stearoyl macrogolglycerides, Sorbitan stearate, Sorbitan laurate, Macrogol glycerol hydroxystearat, colloidal silicon dioxide and mixtures thereof, disintegrants such as starches, clays, cellulose derivatives including crosscarmellose, gums, aligns, various combinations of hydrogencarbonates with weak acids (e.g., sodium hydrogencarbonate/tartaric acid or citric acid) crosprovidone, sodium starch glycolate, agar, cation exchange resins, citrus pulp, veegum, glycollate, natural sponge, bentonite, sucralfate, calcium hydroxyl-apatite or mixtures thereof.

A matrix composition as described herein may comprise one or more gelling agents. Examples are polymers selected from the group consisting of modified or unmodified water soluble natural polymers such as glucomannan, galactan, glucan, polygalacturonic acid, polyxylane, polygalactomannans, polyxyloglycan, arabinogalactan, starch, cellulose, chitosan, alginate, fibrin, collagen, gelatin, amylopectin, pectin including low methylated or methoxylated pectins, dextran; synthetic polymers such as PVA and PVB; and hydrogels made from the polymers or combined polymers mentioned above and or from polymers originated from: HEMA, HEEMA, MEMA, MEEMA, EDGMA, NVP, VAc, AA, acrylamide, MAA, HPMA, PEGA, PEGMA, PEGDMA, PEGDA, and/or PEGDMA, hydroxypropyl methylcellulose, hydroxypropyl cellulose, methylcellulose, hydroxyethyl ncellulose, ethylcellulose, hydroxypropyl methylcellulose phthalate, hydroxypropyl methylcellulose Acetate Succinate or other cellulose derivates, carboxymethylcellulose sodium, carboxymethylcellulose calcium, carrageenans, guar gum, gellan gum, xanthan gum, tragacanth and Arabic gum.

Furthermore, the pharmaceutical compositions described herein may comprise one or more agents selected from sweetening agents, flavouring agents and colouring agents, in order to provide an elegant and palatable preparation. Examples include maltol, citric acid, water soluble FD&C dyes and mixtures thereof with corresponding lakes and direct compression sugars such as Di-Pac from Amstar. In addition, coloured dye migration inhibitors such as tragacanth, acacia or attapulgite talc may be added. Specific examples include Calcium carbonate, 1,3,5-trihydroxybenzene, Chromium-cobalt-aluminium oxide, ferric ferrocyanide, Ferric oxide, Iron ammonium citrate, Iron (III) oxide hydrated, Iron oxides, Carmine red, Magnesium carbonate and Titanium dioxide.

Plasticizers may be incorporated in the pharmaceutical compositions according to the present description. A suitable plasticizer may be selected from mono- and di-acetylated monoglycerides, diacetylated monoglycerides, acetylated hydrogenated cottonseed glyceride, glyceryl cocoate, Polyethylene glycols or polyethylene oxides (e.g., with a molecular weight of about 1,000-500,000 daltons), dipropylene glycol salicylate glycerin, fatty acids and esters, phthalate esters, phosphate esters, amides, diocyl phthalate, phthalyl glycolate, mineral oils, hydrogenated vegetable oils, vegetable oils, acetylated hydrogenated soybean oil glycerides, Castor oil, acetyl tributyl citrate, acetyl triethyl citrate, methyl abietate, nitrobenzene, carbon disulfide, [beta]-naphtyl salicylate, sorbitol, sorbitol glyceryl tricitrate, fatty alcohols, cetostearyl alcohol, cetyl alcohol, stearyl alcohol, oleyl alcohol, myristyl alcohol, sucrose octaacetate, alfa<~>-tocopheryl polyethylene glycol succinate (TPGS), tocopheryl derivative, diacetylated monoglycerides, diethylene glycol monostearate, ethylene glycol monostearate, glyceryl monooleate, glyceryl monostearate, propylene glycol monostearate, macrogol esters, macrogol stearate 400, macrogol stearate 2000, polyoxyethylene 50 stearate, macrogol ethers, cetomacrogol 1000, lauromacrogols, nonoxinols, octocinols, tyloxapol, poloxamers, polyvinyl alcohols, polysorbate 20, polysorbate 40, polysorbate 60, polysorbate 65, polysorbate 80, polysorbate 85, sorbitan monolaurate, sorbitan monooleate, sorbitan monopalmitate, sorbitan monostearate, sorbitan sesquioleate, sorbitan trioleate, sorbitan tristearate and sucrose esters, amyl oleate, butyl oleate, butyl stearate, diethylene glycol monolaurate, glycerol tributyrate, Cumar W-1, Cumar MH-1, Cumar V-1, Flexol B-400, monomeric polyethylene ester, Piccolastic A-5, Piccalastic A-25, Beckolin, Clorafin 40, acetyl tributyl citrate, acetyl triethyl citrate, benzyl benzoate, butoxyethyl stearate, butyl and glycol esters of fatty acids, butyl diglycol carbonate, butyl ricinoleate, butyl phthalyl butyl glycolate, camphor, dibutyl sebacate, dibutyl tartrate, diphenyl oxide, glycerine, HB-40, hydrogenated methyl ester of rosin, methoxyethyl oleate, monoamylphthalate, Nevillac 10, Paracril 26, technical hydroabietyl alcohol, Methylene glycol dipelargonate, solid aliphatic alcohols and mixtures thereof.

Exemplary stabilizers (chemical) include TPG, for example, in the form of TPGS (Vitamin E Polyethylene glycol succinate) and BHT, BHA, t-butyl hydroquinone, butylhydroxy toluene, calcium ascorbate, gallic acid, hydroquinone, maltol, octyl gallate, sodium bisulfite, sodium metabisulfite, tocopherol and derivates thereof, citric acid, tartaric acid, and ascorbic acid. Thus, in one embodiment, a matrix composition as described herein comprises TPGS and/or BHT. Other stabilisers include trivalent phosphorous, such as, for example, phosphite, phenolic antioxidants, hydroxylamines, lactones such as substituted benzofuranones, hindered phenols, thiosynergists and/or hindered amines, acids (ascorbic acid, erythorbic acid, etidronic acid, hypophosphorous acid, nordihydroguaiaretic acid, propionic acid etc.), phenols, dodecyl gallate, octyl gallate, 1,3,5-trihydroxybenzene, organic and inorganic salts (calcium ascorbate, sodium ascorbate, sodium bisulphite, sodium metabisulfite, sodium sulfite, potassium bisulphite, potassium metabisulphite), esters (calcium ascorbate, dilauryl thiodipropionate, dimyristyl thiodipropionate, distearyl thiodipropionate), pyranon (maltol), and vitamin E (tocopherol, D-[alpha]-tocopherol, DL-[alpha]-tocopherol, tocopheryl acetate, d-[alpha]-tocopheryl acetate, dl-[alpha]-tocopheryl acetate. However, other anti-oxidative agents known in the art may also be used. Other suitable stabilizers may be selected from, for example, sorbitol glyceryl tricitrate, sucrose octaacetate.

In one embodiment, a matrix composition as described herein comprises one or more stabilizers selected from above mentioned group of stabilizers. In one such embodiment, the matrix composition comprises butylhydroxytoluene as a stabilizer. In another such embodiment, the matrix composition comprises TPGS as a stabilizer.

A release modifier may be incorporated in a matrix composition as described herein. A suitable release modifier may be selected from fatty acids and esters, fatty alcohols, cetyl alcohol, stearyl alcohol, mineral oils, hydrogenated vegetable oils, vegetable oils, acetylated hydrogenated soybean oil glycerides, Castor oil, phosphate esters, amides, phthalate esters, glyceryl cocoate oleyl alcohol, myristyl alcohol, sucrose octaacetate, diacetylated monoglycerides, diethylene glycol monostearate, ethylene glycol monostearate, glyceryl monooleate, glyceryl monostearate, propylene glycol monostearate, macrogol esters, macrogol stearate 400, macrogol stearate 2000, polyoxyethylene 50 stearate, macrogol ethers, cetomacrogol 1000, lauromacrogols, poloxamers, polyvinyl alcohols, sorbitan monolaurate, sorbitan monooleate, sorbitan monopalmitate, sorbitan monostearate, sorbitan sesquioleate, sorbitan trioleate, sorbitan tristearate, ethylcellulose, cellulose acetate, cellulose propionate, cellulose nitrate, cellulose derivative selected from the group consisting of methylcellulose, carboxymethylcellulose and salts thereof, cellulose acetate phthalate, microcrystalline cellulose, ethylhydroxyethylcellulose, ethylmethylcellulose, hydroxyethylcellulose, hydroxyethylmethylcellulose, hydroxypropylcellulose, hydroxypropylmethylcellulose, hydroxymethylcellulose and hydroxymethylpropylcellulose, cellulose acetate, polylactic acid or polyglycolic acid and copolymers thereof, methacrylates, a co-polymer of methacrylate-galactomannan etc., Polyvinyl alcohols, glycerinated gelatine and cocoa butter.

Other suitable release modifiers may be selected from inorganic acids, inorganic bases, inorganic salts, organic acids or bases and pharmaceutically acceptable salts thereof, saccharides, oligosaccharides, polysaccharides, polyethylene glycol derivatives and cellulose and cellulose derivatives.

Alternatively or additionally, a matrix composition according to the present description may include a pharmaceutically acceptable excipient selected from a mono-, di-, oligo, polycarboxylic acid or amino acids such as, for example, acetic acid, succinic acid, citric acid, tartaric acid, acrylic acid, benzoic acid, malic acid, maleic acid, sorbic acid etc., aspartic acid or glutamic acid etc.

Suitable organic acids that may be included in the compositions described herein include, for example, acetic acid/ethanoic acid, adipic acid, angelic acid, ascorbic acid/vitamin C, carbamic acid, cinnamic acid, citramalic acid, formic acid, fumaric acid, gallic acid, gentisic acid, glutaconic acid, glutaric acid, glyceric acid, glycolic acid, glyoxylic acid, lactic acid, levulinic acid, malonic acid, mandelic acid, oxalic acid, oxamic acid, pimelic acid, or pyruvic acid.

Suitable inorganic acids that may be included in the compositions described herein include, for example, pyrophosphoric, glycerophosphoric, phosphoric such as ortho and meta phosphoric, boric acid, hydrochloric acid, or sulfuric acid.

Examples of suitable inorganic compounds that may be included in the compositions described herein include, for example, aluminium.

Examples of organic bases that may be included in the compositions described herein include, for example, p-nitrophenol, succinimide, benzenesulfonamide, 2-hydroxy-2cyclohexenone, imidazole, pyrrole, diethanolamine, ethyleneamine.tris(hydroxymethyl)aminomethane, hydroxylamine and derivates of amines, sodium citrate, aniline or hydrazine. Examples of inorganic bases that may be included in the compositions described herein include, for example, aluminium oxide such as, for example, aluminium oxide trihydrate, alumina, sodium hydroxide, potassium hydroxide, calcium carbonate, ammonium carbonate, ammonium hydroxide or KOH.

Pharmaceutically acceptable salts of an organic acid that may be included in the compositions described herein include, for example, an alkali metal salt or an alkaline earth metal salt such as, for example, sodium phosphate, sodium dihydrogenphosphate, disodium hydrogenphosphate etc., potassium phosphate, potassium dihydrogenphosphate, potassium hydrogenphosphate etc., calcium phosphate, dicalcium phosphate etc., sodium sulfate, potassium sulfate, calcium sulfate, sodium carbonate, sodium hydrogencarbonate, potassium carbonate, potassium hydrogencarbonate, calcium carbonate, magnesium carbonate etc., sodium acetate, potassium acetate, calcium acetate, sodium succinate, potassium succinate, calcium succinate, sodium citrate, potassium citrate, calcium citrate, sodium tartrate, potassium tartrate or calcium tartrate.

Suitable inorganic salts for that may be used in a matrix composition as described herein include, for example, sodium chloride, potassium chloride, calcium chloride or magnesium chloride.

The matrix composition may comprise at least one saccharide. Where a saccharide is included in a matrix composition as described herein, the saccharide may be selected from, for example, glucose, ribose, arabinose, xylose, lyxose, xylol, allose, altrose, inosito, glucose, sorbitol, mannose, gulose, Glycerol, idose, galactose, talose, mannitol, erythritol, ribitol, xylitol, maltitol, isomalt, lactitol, sucrose, fructose, lactose, dextrin, dextran, amylase or xylan. In one such embodiment, the matrix composition comprises mannitol.

The matrix composition may also comprise polyethylene glycol derivatives such as, for example, polyethylene glycol di(2-ethyl hexoate), polyethylene glycols (200-600 daltons) or polyethylene oxides, for example, with an average molecular weight of about 800-500,000 daltons, typically about 1,000-100,000 daltons, more typically 1,000-50,000 daltons, especially about 1,000-10,000 daltons, in particular about 1,500-5,000 daltons, or mixtures thereof.

The matrix composition may also comprise cellulose and/or cellulose derivatives selected from the group consisting of methylcellulose, carboxymethylcellulose and salts thereof, microcrystalline cellulose, ethylhydroxyethylcellulose, ethylcellulose, cellulose acetate, cellulose proprionate, cellulose nitrate, cellulose acetate phthalate, ethylmethylcellulose, hydroxyethylcellulose, hydroxyethylmethylcellulose, hydroxypropylcellulose, hydroxypropylmethylcellulose, hydroxymethylcellulose and hydroxymethylpropylcellulose.

Preparation

The pharmaceutical composition as well as the matrix composition of the invention may be produced by various methods which are either known per se in the pharmaceutical industry or which, for example, are used in the production of polymer-based materials, depending upon the desired embodiment and the materials employed in the composition in question. The compositions according to the present description may be produced by methods that are relatively simple and inexpensive.

Suitable preparation methods for compositions according to the invention include extrusion, injection moulding, moulding, tabletting, capsule filling, melt-processing, spray coating, micro encapsulation and other methods of preparing controlled release compositions. Also a combination of one or more of the aforementioned may be employed.

The controlled release composition may be prepared by several different methods. Many systems for controlled release are marketed and it is currently an aim for the industry to reduce the risk of dose dumping, drug abuse or alcohol induced dose dumping in each of the systems.

In other words, in addition to a less frequent administration, one challenge in controlled release delivery may be expressed by the goal of decreasing the incidence of adverse effects and at the same time increasing the efficacy of the treatment. This may be obtained by an interaction between the specific pharmacological properties of the active drug substance and the matrix composition.

High concentrations or a fast rise in the concentration of, for example, opioids is a significant factor associated with undesirable side effects, including the risk addiction. The fear of addiction is often an obstacle for initiation of the otherwise effective pain treatment with, for example, morphine, hydrocodone or oxycodone.

Compositions for controlled release according as described herein may be prepared in numerous ways giving rise to different release mechanisms. For example, the compositions described herein may be prepared by 1, 2 or multiple component injection mouldings, by conventional tablet compression, by micro encapsulation, by 1, 2 or multiple component extrusions, by moulding, by capsule filling or by melt-processing. In cases where a preparation is needed in order to make the controlled release properties before/after the above mentions preparation Steps, the preparation may also comprise separate steps as for example wet granulation, dry granulation, melt granulation, pelletizing, spray coating, electrostatic coating or other forms of controlled release forming preparation methods.

In a particular example, the composition is prepared by two component injection moulding of a matrix composition and a coating (which may be any of the coatings described herein below in the section "Coating") surrounding the matrix and exposing at least one surface of the matrix, preferably the two ends of the matrix composition for erosion governed release.

A composition may also be produced by, for example, moulding, injection moulding, multiple component injection moulding, co-extrusion of the coating with the matrix composition and the active drug substance, extrusion and dip coating, injection moulding and dip coating, or by extrusion or injection moulding and solvent coating by spraying or dipping, or a combination of these methods.

Geometry

As disclosed herein, the release mechanisms of the pharmaceutical compositions described herein depend, at least in part, on the geometry of the composition. For example, erosion based release from a matrix depends on the area of the matrix exposed to the environment. In embodiments of the pharmaceutical compositions described herein, wherein the opening(s) in the coating are of the same shape and size as the cross section of the matrix composition, erosion of the matrix composition will depend upon the cross sectional area of the opening(s), with the rate of erosion (and therefore the rate of delivery of active drug substance) increasing as the cross-sectional area of the matrix composition exposed by the one or more openings in the coating increases. The area of the matrix composition exposed to its surroundings (and therefore the delivery characteristics provided) may be manipulated by employment of a coat that is not subject to erosion and thus covering areas of the matrix that should not be releasing sites.

The geometric form of the composition may also be manipulated to achieve controlled release as described herein. In one embodiment, the pharmaceutical composition has a geometric shape, which enables a substantially constant surface area of the matrix composition to become exposed during erosion of the matrix and delivery of an active drug substance contained therein.

The pharmaceutical compositions described herein are cylindrical compositions with optionally tapered end(s). It follows, then, that the matrix composition included in such pharmaceutical compositions also exhibits a cylindrical shape (optionally with tapered end(s)). The matrix composition is substantially surrounded by a coating having at least one or two openings allowing exposure of at least one surface of said matrix to its surroundings.

A cylindrical shape as contemplated herein may be any geometrical shape having the same cross section area throughout the length of the geometrical shape. Thus, the term "cylindrical shape" as used herein preferably refers to any geometrical shape having the same cross section area along an axis, preferably the longitudinal axis. Within the present context, cross sections are perpendicular to the axis of the cylinder. By way of example, if the cylindrical shape is elongated then the cross sections are perpendicular to the longitudinal axis. The cylindrical shape is typically elongated. The cross section of a cylinder within the meaning of the present description may have any two dimensional shape, for example the cross section may be circular, oval, parabola, hyperbola, rectangular, triangular, otherwise angular, polygonal, star shaped or an irregular shape. In preferred embodiments of the invention the cross section is oval or circular. In particular embodiments, the pharmaceutical compositions described herein have a cylindrical shape, wherein one or both end(s) may be tapered, for example one or both end(s) may be rounded. Thus, the matrix may taper along the longitudinal axis, i.e. the area of the cross section may decrease along the longitudinal axis towards one or both ends of the matrix.

Accordingly, the cylindrical shape of a pharmaceutical composition according to the present description may for example be an elliptic cylinder, a parabolic cylinder, a hyperbolic cylinder or a prism. A prism within the present context is a cylinder whose cross-section is a polygon.

Figure 11:
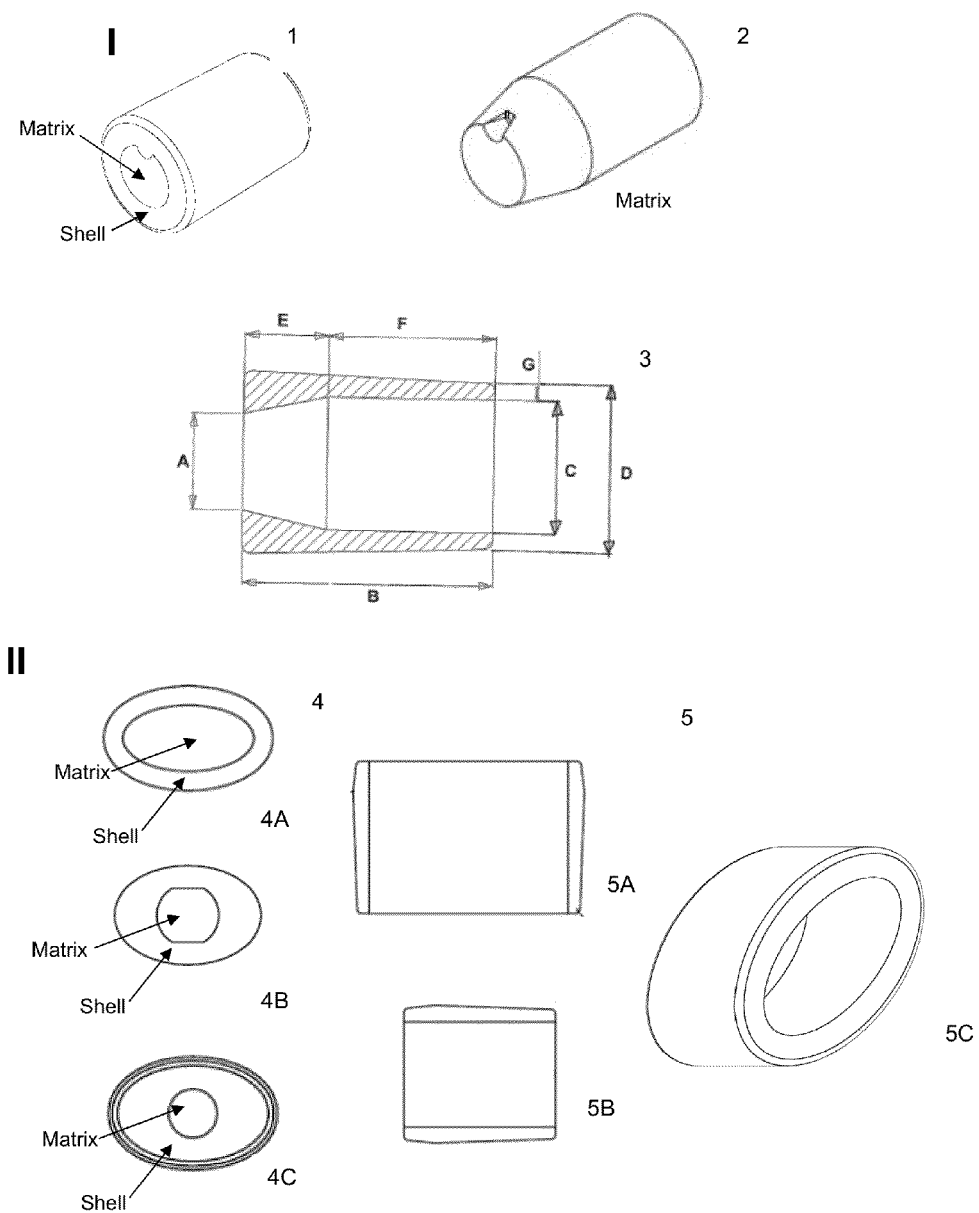
FIG. 11 shows examples of geometries of pharmaceutical compositions according to the present description. The active drug substance is dispersed in a matrix partly covered by a coating, preferably a non-impermeable coating. I: 3-D view of round tablet and a tablet with one tapered end. II: 3-D view of one type of oval tablet and matrix with different shapes. III: 3-D view of second type of oval tablet with round matrix. IV: 3-D view of third type of oval tablet with an oval matrix. Relative sizes of tablets are not shown.
Figure 11:
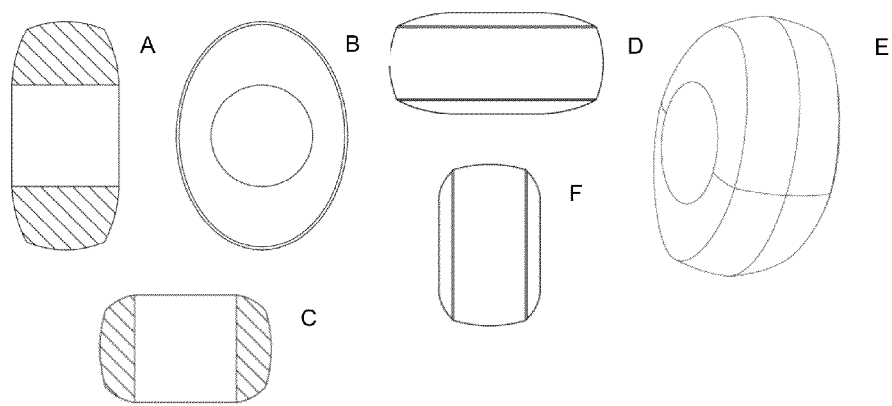
Figure 11:
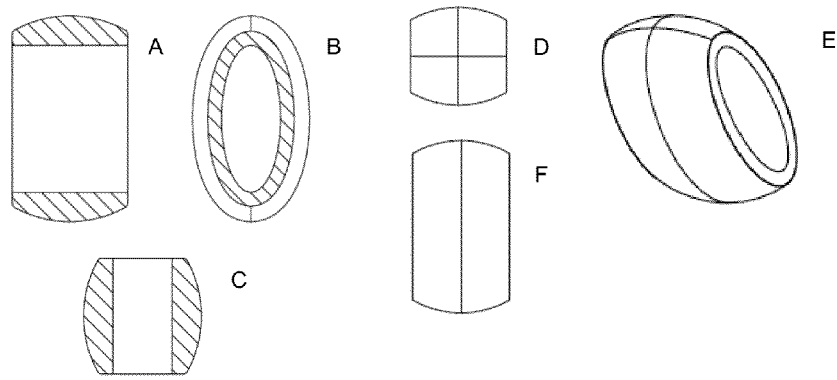

FIG. 11 shows examples of specific pharmaceutical compositions. The skilled person will appreciate that the depicted shapes also may be applied to other pharmaceutical compositions. Accordingly, the pharmaceutical compositions consisting of a matrix surrounded by a coating according to the present invention may for example have any of the cylindrical shapes shown in FIG. 11, wherein, FIG. 11 I-1 shows the 3 dimensional structure of a round pharmaceutical composition and FIG. 11 I-2 shows a 3 dimensional shape of a matrix, FIG. 11 II, III and IV show pharmaceutical compositions with an oval shape, wherein the cross section of the matrix has either an oval shape or a round shape (FIG. 11 II-4). The skilled person will appreciate that other shapes are also useful for the pharmaceutical compositions described herein. For example, the matrix shown in FIG. 11 II-2 may also be a cylinder without a tapered end or it may have two tapered ends rather than one.

FIG. 11 I-3 shows an exemplary pharmaceutical composition. The pharmaceutical composition has a matrix with a cylindrical part the length of which is designated F and the diameter designated C. The matrix further has a tapered end, the length of which is designated E and the diameter of the part of the end which is shortest is designated A. The entire length of the matrix is designated B. The matrix is surrounded by a coating, which has a thickness of G in one end. The overall diameter of the pharmaceutical composition is designated D. FIG. 11 I-3 shows an example of a pharmaceutical composition according to the present description, and it will be apparent to the skilled person that modifications may be made, for example pharmaceutical compositions as described herein may be produced without tapered ends, with two tapered, with a coating that is uniformly thick, and/or wherein the cross section of the matrix has either an oval shape or a round shape The pharmaceutical composition as well as the matrix composition used in forming the pharmaceutical composition may be a cylindrical shape with one tapered end or two tapered ends.

Thus, the shape of the matrix may be defined by a main cylindrical body (herein referred to as "cylinder part of the matrix") optionally with one or two tapered ends. FIG. 11 I-3, for example, shows a cylinder part of the matrix defined by FxC. The cylinder part of the matrix is in general completely cylindrical. In certain embodiments, the length of said cylinder part of the matrix (e.g., F in FIG. 11 I-3) is in the range of 7.5 mm to 15 mm, and may be selected from, for example, a range of 8 to 15 mm, a range of 8 to 10 mm, a range of 8.2 to 9.8 mm, a range of 8.4 to 9.6 mm, a range of 8.5 to 9.5 mm, a range of 8.7 to 9.3 mm, and a range of 8.9 to 9.1 mm. In specific such embodiments, the length of said cylinder part of the matrix may be selected from 9 mm, and 9.5 mm long along the longitudinal axis. Aforementioned lengths are in particular relevant for pharmaceutical compositions formulated for continued administration of an active drug substance over an interval ranging from about 20 to 28 hours. In certain such embodiments, the pharmaceutical composition is formulated and produced for continued administration of an active drug substance over an interval selected from about 20 to 28 hours, about 22 to 26 hours, and about 23 to 25 hours. In a specific such embodiment, the pharmaceutical composition is formulated and produced for continued administration of an active drug substance over a 24 hour interval.

In specific embodiments, the matrix is relatively long, such as longer than 9 mm, for example in the range of 9 to 15 mm, such as in the range of 9 to 12 mm, for example approximately 9 mm, such as approximately 10 mm, for example approximately 11 mm, such as approximately 12 mm, for example 9 mm, such as 10 mm, for example 11 mm, such as 12 mm long. Compositions of these longer lengths are suitable for pharmaceutical compositions formulated for continued administration of an active drug substance over an interval selected from a range of about 20 to 28 hours, about 22 to 26, and about 23 to 25 hours. In certain such embodiments, the pharmaceutical composition is formulated and produced for continued administration of an active drug substance over a 24 hour interval.

In another specific embodiment, the length of said cylinder part of the matrix (e.g., F in FIG. 11 I-3) or the entire length of the matrix (e.g., B in FIG. 11 I-3) is in a range selected from 7.5 mm to 15 mm, preferably 7.5 to 10 mm, and 7.5 to 8 mm. along the longitudinal axis. Compositions of these longer lengths are suitable for pharmaceutical compositions formulated for continued administration of an active drug substance subject to entero-hepatic recirculation over an interval selected from a range of about 20 to 28 hours, about 22 to 26, and about 23 to 25 hours. In certain such embodiments, the pharmaceutical composition is formulated and produced for continued administration of an active drug substance over a 24 hour interval.

As defined above, the cross section area along an axis, preferably the longitudinal axis of said cylinder part of the matrix is constant. In one embodiment, the cross sectional area of the cylinder part of the matrix is at least 1 $mm^2$. For example, in certain embodiments, the cross sectional area of the cylinder part of the matrix is in a range selected from 1 to 150 $mm^2$, 1 to 100 $mm^2$, 1 to 75 $mm^2$, 1 to 60 $mm^2$, and 2 to 60 $mm^2$.

In another embodiment, the cross section area of the cylinder part of the matrix is at least 20 $mm^2$. For example, in certain embodiments, the cross sectional area of the cylinder part of the matrix is selected from at least 22 $mm^2$, at least 24 $mm^2$, at least 26 $mm^2$, at least 28 $mm^2$. In other such embodiments, the cross sectional area of the cylinder part of the matrix is in a range selected from 20 to 100 $mm^2$, 20 to 75 $mm^2$, 20 to 60 $mm^2$, 20 to 40 $mm^2$, 22 to 100 $mm^2$, 22 to 75 $mm^2$, 20 to 60 $mm^2$, 22 to 40 $mm^2$, 24 to 100 $mm^2$, 24 to 75 $mm^2$, 24 to 60 $mm^2$, 24 to 40 $mm^2$, 26 to 100 $mm^2$, 26 to 75 $mm^2$, 26 to 60 $mm^2$, 26 to 40 $mm^2$, 28 to 100 $mm^2$, 28 to 75 $mm^2$, 28 to 60 $mm^2$, 28 to 40 $mm^2$.

In FIG. 11 I-3, the diameter of the cross section is indicated as C. This embodiment is in particularly useful for compositions comprising a low load of active drug substance, such as those compositions having less than 50%, such as less than 40% active drug substance. Aforementioned cross-section areas may be sued in preparation of pharmaceutical compositions formulated for continued administration of an active drug substance over a period of time ranging from about 20 to 28 hours, such as those providing continued administration of an active drug substance over a period of time in a range selected from about 22 to 26 hours and about 23 to 25 hours. In once such embodiment, pharmaceutical compositions formulated for continued administration of an active drug substance over a period of 24 hours.

Thus, in specific embodiments, the cylinder part of the matrix has a length in a range selected from 7.5 to 15 mm and 8 to 10 mm and a cross sectional area of at least 20 $mm^2$. For example, the cylinder part of the matrix may have a length selected from between 7.5 and 15 mm, and between 8 to 10 mm and a cross sectional area of in the range of 20 to 100 $mm^2$, such as a length of the range of 8.5 to 9.5 mm and a cross sectional area in the range of 20 to 100 $mm^2$, for example a length of the range of 8.9 to 9.1 mm and a cross section area of in the range of 20 to 100 $mm^2$, such as a length of 9 mm and a cross section area of in the range of 20 to 100 $mm^2$. In another embodiment, the cylinder part of the matrix may have a length selected from between 7.5 and 15 mm and between 8 to 10 mm and a cross section area of at least 1 $mm^2$. For example, in such an embodiment, the cylinder part of the matrix may have a length selected from between 7.5 to 15 mm and between 8 to 10 mm and a cross section area in a range selected from 1 to 150 $mm^2$, 1 to 100 $mm^2$, 1 to 75 $mm^2$, 1 to 60 $mm^2$, and 2 to 60 $mm^2$.

As described above, the pharmaceutical composition may comprise a main cylindrical body (also referred to as "cylinder part of the matrix") optionally with one or two tapered ends. For example, FIG. 11 I-3 shows one tapered end the length of which is E, the shortest diameter A and the longest diameter C. The length of the tapered end (e.g., E in FIG. 11 I-3) may be 0 (i.e., no tapered end) or it may be as long as 40% of the total length, preferably up to 33% of the total length. In embodiments of the invention wherein the pharmaceutical composition comprises one or two tapered ends, the total length of the matrix, including both the cylindrical part of the matrix as well as the tapered end(s) (e.g., B in FIG. 11 I-3), may be in a range selected from 7.5 to 15 mm, 8 to 15 mm, 8 to 10 mm, 8.2 to 9.8 mm, 8.4 to 9.6 mm, 8.5 to 9.5 mm, 8.7 to 9.3 mm, and 8.9 to 9.1 mm. In specific such embodiments, the total length of the matrix, including both the cylindrical part of the matrix as well as the tapered end(s), may be selected from 9 mm and 9.5 mm along the longitudinal axis.

The matrix composition may be surrounded by a coating having at least one opening exposing at least one surface of said matrix. In particular embodiments, the matrix composition may be surrounded by a coating having one opening exposing at least one surface of said matrix. In other embodiments, the matrix composition may be surrounded by a coating having at two openings exposing at least two surfaces of said matrix. Openings provided in the coating may be positioned at one or both end(s) of said cylindrical matrix, thereby exposing at least one end of the cylindrical shape to the surrounding environment. Of course, where a pharmaceutical composition as described herein is provided with a matrix having a coating that includes two openings, one at each end of a cylindrical matrix, the pharmaceutical composition includes two ends of the cylindrical shape exposed to the surrounding environment.

The inner surface of a coating provided over a matrix composition as described herein will have essentially the same shape (or generally exactly the same shape) as the matrix except that the coating contains, for example, one or two openings. In particular embodiments, the thickness of the coating is uniform and thus the coating will have essentially a similar shape as the matrix except that the coating contains, for example, one or two openings and that the coating in the absence of the matrix is hollow. Obviously, the outer diameter of the coating will be larger than the outer diameter of the matrix. The difference in diameter will be dependent on the thickness of the coating. The thickness of the coating may, for example, be as shown in FIG. 11 I-3, indicated as G.

It is, however, also contemplated that in other embodiments, the coating is not uniformly thick and, thus, while the inner surface of the coating will have essentially the same shape (or generally exactly the same shape) as the matrix, the outer surface of the coating may have a different shape. In specific such embodiments, the outer surface of the coating is, nevertheless, cylindrical and may take any of the cylindrical shapes described herein above in relation to the matrix.

The coating (sometimes also referred to as "shell") may be cylindrical, and in certain embodiments, both the inner surface and the outer surface of the coating are cylindrical. However, optionally, the coating may furthermore be rounded at the first end and/or the second end. The coating may also taper along the longitudinal axis at one or both ends.

As mentioned above, the coating is preferably cylindrical optionally with tapered ends and it is preferred that the length of said coating (e.g., B in FIG. 11 I-3) is in a range selected from 7.5 mm to 15 mm, 8 to 15 mm, 8 to 10 mm, 8.2 to 9.8 mm, 8.4 to 9.6 mm, 8.5 to 9.5 mm, 8.7 to 9.3 mm, and 8.9 to 9.1 mm. In one such embodiment, the length of said coating is 9 mm measured along the longitudinal axis of said cylinder. Aforementioned lengths of said coating are in particular relevant for pharmaceutical compositions formulated for continued administration of an active drug substance over a period of time ranging from about 20 to about 28 hours, such as those providing continued administration of an active drug substance over a period of time in a range selected from about 22 to about 26 hours and about 23 to about 25 hours. In once such embodiment, pharmaceutical compositions formulated for continued administration of an active drug substance over a period of about 24 hours.

Therefore in specific embodiments of the pharmaceutical compositions described herein, the coating is the same length as the matrix. Thus, by way of example, if the matrix is about 9 mm, then in such embodiments, the length of the coating matches the length of the matrix and is also about 9 mm. In some embodiments, wherein the matrix contains one or two tapered ends, then the coating may be shorter than the matrix. In these embodiments, the coating may have the same length as the cylindrical part of the matrix, and thus covers the cylinder part of the matrix leaving the tapered ends exposed.

Pharmaceutical compositions formulated for administration more frequent than an interval ranging from about 20 to about 28 hours between administrations are, in general, shorter that those formulated and produced to provide administration of an active drug substance over an interval of about 20 to 28 hours. In one aspect, the pharmaceutical compositions described herein include:
 a) a matrix composition comprising
  i) an active drug substance as described herein; and
  ii) at least one polyglycol as described herein,
 said matrix composition having a cylindrical shape with optionally tapered end(s), with the length of said matrix being in a range selected from 4 to 8 mm, 5.5 to 8 mm, 6 to 7.5 mm, and 6 or 7.5 mm, said matrix being surrounded by
 b) a coating having one or two openings exposing at least one surface of said matrix, said coating being substantially impermeable to an aqueous medium.

The cross section of these compositions is preferably at least 1 $mm^2$. For example, in particular embodiments, the cross sectional area of such compositions may be in a range selected from 1 to 150 $mm^2$, 1 to 100 $mm^2$, 1 to 75 $mm^2$, and 20 to 75 $mm^2$. Such embodiments can be formulated for continued administration of an active drug substance over an interval of time selected from about 5 to 20 hours, about 7 to 20 hours, and about 10 to 20 hours. In certain such embodiments, the pharmaceutical composition may be formulated for continued administration of an active drug substance over an interval of time selected from about 10 to 18 hours, about 10 to 16 hours, about 10 to 14 hours, and about 11 to 13 hours. And in one such embodiment, pharmaceutical composition may be formulated for continued administration of an active drug substance over a 12 hour interval between individual administrations.

Thus, the pharmaceutical compositions described herein may be cylindrical in shape with the two ends exposing the eroding matrix composition. Such a shape will typically give rise to zero order release because the releasing area is constant. In a specific example, the compositions employed are coated in such a manner that the surface has a substantially constant or controlled surface area during release or erosion. In the present context, controlled surface area relates to a predetermined surface area typically predicted from the shape of the coat of the unit dosage system. It may have a simple uniform cylindrical shape or the cylindrical form can have one or more tapered ends in order to decrease (or increase) the initial release period.

As yet another example, the release mechanism of dissolving/solubilization also depends on the releasing area and the release rate may be controlled by what area of the matrix is covered by said coating. In general, the majority of the matrix is covered by a coating having one or two openings. In embodiments described herein, the sides of the cylindrical shape (i.e., of the cylindrical matrix) are at least partly covered by said coating. In specific embodiments, at least 70%, at least 80%, at least 90%, at least 95%, or all of the sides of the cylindrical shape (i.e., of the cylindrical matrix) are covered by said coating. One or both ends of the matrix, including optionally tapered ends may be partly covered by said coating, or they may be uncovered by any coating. Thus, one or both ends may be exposed to the surroundings.

In a particular embodiment, the pharmaceutical composition is prepared for oral intake, preferably for oral intake by swallowing. Accordingly, the size of the pharmaceutical composition should be in a range that allows oral intake by swallowing.

Where the pharmaceutical composition is produced for oral administration, the coating or shell has outer dimensions making the shell suitable for oral administration. The shell may have a length (extension along the first axis, e.g., B in FIG. 11 I-3) in a range selected from about 7.5 mm to 15 mm and 8 mm to 10 mm (see above). The shell may have a height (extension along the second axis, e.g., the diameter, e.g., D in FIG. 11 I-3) in a range selected from about 2 mm to 20 mm, 2 mm to 15 mm, 2 to 10 mm, and 4 to 10 mm. In certain such embodiments, the shell may have a height selected from approximately 4.5 mm, approximately 5.6 mm, and approximately 8.3 mm. The shell may have a width (extension along the third axis, e.g., diameter, e.g., D in FIG. 11 I-3) in a range selected from approximately 2 mm to 20 mm, 2 mm to 15 mm, 2 to 10 mm, 4 to 10 mm, and 3 to 5 mm. In certain such embodiments, the shell may have a width selected from approximately 3.4 mm, approximately 4.3 mm, approximately 4.4 mm, approximately 4.5 mm, and approximately 4.7 mm. In this context approximately means +/−10%. The outer surface of the shell may have a double curved surface to facilitate oral administration of a pharmaceutical composition comprised in the shell.

The opening may have any suitable shape, such as, for example, circular, oval, rectangular, triangular, angular, polygonal or star shaped. The opening may have a shape similar to or the same as the cross section of the matrix. In specific embodiments, the pharmaceutical compositions comprise a matrix surrounded by a coating having two openings, wherein each opening is positioned at each end of said matrix and each opening has essentially the same shape as the cross section of said matrix. For example, in FIG. 11 I-3, one opening has a diameter of A and the other a diameter of C. It is also possible that two openings have a diameter of C. An opening may have any suitable size, such as an area in a range selected from about 1 mm² to about 150 mm², about 1 mm² to about 100 mm², about 1 mm² to about 75 mm², and about 2 mm² to about 65 mm². In one embodiment, the opening has the same area as the cross sectional area of the cylindrical part of the matrix. Thus by way of example, in such an embodiment, if the cross sectional area is in the range of 1 to 75 mm², then the area of one opening is preferably also in the range of 1 to 75 mm² and, accordingly, the area of two openings in total would then be in the range of 2 to 150 mm². Similarly, if the cross sectional area is at least 20 mm², then the area of one opening is also at least 20 mm² and, accordingly, the area of two openings in total would then be at least 40 mm².

Coating

The pharmaceutical compositions according to the invention comprise a matrix substantially surrounded by a coating with at least one opening. In certain embodiments, the coating includes one opening. In other embodiments, the coating includes two openings. In further such embodiments, the pharmaceutical compositions consist essentially of a matrix substantially surrounded by a coating as described herein.

The coating may also be referred to as "shell" herein and these terms are used interchangeably. The shape of the shell or coating is described herein above in the section "Geometry". The composition of the shell or coating is described herein below.

For the present purpose, the shell or coating is impermeable to an aqueous medium, such as water. This ensures that the matrix is in contact with surrounding aqueous media via the one or more openings in the coating. In addition, in particular embodiments, the coating is substantially insoluble in an aqueous medium, and in certain such embodiments, the coating is insoluble in an aqueous medium.

In a specific example, the coating is substantially insoluble, non-erodible and impermeable to water leaving only the exposed areas of the matrix for release. Within the present context, the coating is considered substantially insoluble in an aqueous medium if the coating dissolves so much slower in an aqueous medium than the matrix composition that the coating remains intact until the matrix has eroded and/or released the active drug substance.

A coating is considered substantially insoluble in water when it has a solubility in water of at least 100, for example at least 1000, wherein solubility is determined as parts of water needed to dissolve 1 part of solute at ambient temperature. The coating is considered insoluble in water, when it has a solubility in water of at least 10,000, wherein solubility is determined as parts of water needed to dissolve 1 part of solute at ambient temperature.

In an embodiment, the coating is one which biodegrades, disintegrates crumbles or dissolves after erosion of the matrix and/or during the release of the active drug substance. In particular embodiments, therefore, a coating applied for an erosion matrix will remain intact as long as it is supported by the matrix containing the active drug substance, but it lacks the ability to remain intact after erosion of the matrix, because it then biodegrades, disintegrates or crumbles, so that it will not remain in, for example, a human for any significant amount of time after the complete erosion of the matrix and the release of the active drug substance.

In a one embodiment, the shell (coating) may biodegrade, disintegrate, crumble or dissolve after erosion of the matrix composition and/or during the release of the active drug substance in the matrix composition.

The coating or shell in general comprises or even consist of one or more polymers. It is preferred that at least one such polymer is a thermoplastic polymer. In some embodiments, all polymers included in the shell are thermoplastic polymers.

Thus, in one embodiment all the polymers used to form the shell (coating) are thermoplastic polymers. As used herein, "thermoplastic polymers" refers to polymers that are an elastic and flexible liquid when heated and freezes to a solid state when cooled (e.g., cooled to 20° C. or to ambient temperature).

The shell (coating) may be made of a material comprising one or more of the polymers described herein in this section. For example, the shell may be made of a material comprising one or more starch based polymers, one or more cellulose based polymers, one or more synthetic polymers, one or more biodegradable polymers or a combination thereof, such as mixtures of starch and synthetic polymers or mixtures of starch and biodegradable polymers.

In some embodiments, the shell (coating) may be made of a material comprising one or more polymers selected from the group consisting of Ethyl cellulose grade 20 and 100, polylactic acid (PLA), Cornpack 200, polycaprolactone, PEO 7000000 and polyhydroxybuturate.

Starch Based Polymers

The shell (coating) may comprise one or more starch based polymers. In particular embodiments, the starch based polymer may be starch as such or a polymer having a high starch content selected from more than 70% starch, more than 80% starch, or more than 90% starch. Starch is a linear polysaccharide made up of repeating glucose groups with glyco-sidic linkages in the 1-4 carbon positions with chain lengths of 500 to 2,000 glucose units. There are two major polymer molecules in starch-amylose and amylopectin.

Starch based polymers that may be used in forming a shell suitable for use in pharmaceutical compositions described herein may be thermoplastic starch biodegradable plastics (TPS). TPS have a starch (amylose) content greater than 70% and are, in general, based on gelatinised vegetable starch. Said vegetable starch may for example be selected from the group consisting of potato starch, rice starch, maize starch, tapioca starch, wheat starch, dextrin, carrageenan and chitosan. Said vegetable starch may provide suitable polymers used in the shell (coating) composition. Starch based polymers, in general, do not have a specified melting point, but typically change phase within a temperature range of 90° C. to 260° C., depending upon the chain length of the starch based polymer, water content, and their branching and added side-groups as does the degree of crystallinity of the starch. Long chained-starches are usually completely amorphous, while shorter length starches may be semi-crystalline (20-80% crystalline). In specific embodiments relatively long polymer chains can contribute to the hardness of the shell, while not being too brittle.

Starch-based polymers are in general fully biodegradable as they are product of plant materials. The degradation rate varies and can be further induced by addition of other biodegradable polymers as listed herein.

One example of a starch based polymer, which may be used to form the shell or coating described herein is maize starch. Maize starch is a linear polysaccharide made up of repeating glucose groups with glyco-sidic linkages in the 1-4 carbon positions with chain lengths of 500 to 2,000 glucose units. There are two major polymer molecules in starch-amylose and amylopectin. An example of a suitable maize starch is cornpack. Cornpack is the maize starch used in some examples described herein below.

Starch is widely used in the food and pharmaceutical industries as a binder and diluent. It is edible and essentially nontoxic. Starch is in general cheap and obtains a good hardness when moulded. Starch may, in general, also be reheated several times without losing its thermodynamic properties. Accordingly, in particular embodiments of the pharmaceutical compositions described herein, the coating comprises at least one starch based polymer, and in certain such embodiments, the coating comprises a starch. Utilization of a starch in forming the coating compositions may be a great advantage when applying injection moulding or co-extrusion as a production process.

Starch based polymers are in general decomposable, and usually have a fast disintegration rate, especially in mixture with biodegradable polymers. Starch based polymers are in generally recognized as stable and inert in solid dosage forms.

Cellulose Based Polymers

The coating or the shell may also comprise one or more cellulose based polymers. In certain embodiments, the coating may even consist of one or more cellulose based polymers (such as ethyl cellulose) combined with one or more and plasticizers (such as any of the plasticizers described in this section below) and UV stabilisers (such as any of the UV stabilisers described in this section below).

Cellulose based polymers are useful in forming a shell (coating) composition because cellulose based polymers, for example, ethylcellulose (particularly grade 100-300), frequently have increased hardness and high ductility.

Therefore, in particular embodiments, the coating comprises a cellulose based polymer which is substantially insoluble or is insoluble in an aqueous medium. The cellulose based polymer may be cellulose, wherein one or more of the free —OH groups have been substituted with an R-group to form a —O—R group. R may in this context, for example, be linear or branched lower alkyl, linear or branched lower alkyl-OH, linear or branched lower alkyl-COOH, —CO-(linear or branched lower alkyl), nitrate, aromatic rings or combinations of the aforementioned. Lower alkyl is preferably a $C_{1-10}$ alkyl, more preferably $C_{1-6}$ alkyl.

Accordingly, the cellulose based polymer may, for example, be one or more selected from ethylcellulose, cellulose acetate, cellulose propionate, cellulose nitrate, methylcellulose, carboxymethylcellulose and salts thereof, cellulose acetate phthalate, ethylhydroxyethylcellulose, ethylmethylcellulose, hydroxyethylcellulose, hydroxyethylmethylcellulose, hydroxypropylcellulose, hydroxypropylmethylcellulose, hydroxymethylcellulose and hydroxymethylpropylcellulose and cellulose acetate.

The coating may also comprise one or more cellulose based polymers selected from cellulose acetate, cellulose propionate, silicified microcrystalline cellulose, cellulose nitrate, methylcellulose, carboxymethylcellulose and salts thereof, cellulose acetate phthalate, microcrystalline cellulose, ethylhydroxyethylcellulose, ethylmethylcellulose, hydroxyethylcellulose, hydroxyethylmethylcellulose, hydroxypropylcellulose, hydroxypropylmethylcellulose, hydroxymethylcellulose phthalate, hydroxymethylcellulose and hydroxymethylpropylcellulose, cellulose acetate, ceratonia (high molecular-weight 310 000 daltons).

Cellulose based polymers are, in general fully, biodegradable as they preferably are products of plant materials. The degradation rate of cellulose based polymers is, in general, slower than that of starch based polymers. This degradation rate can be induced or increased by addition of other biodegradable polymers as listed herein. These other polymers may be polymers which can be attacked by microorganism which degrades the shell (coating) composition into smaller pieces giving rise to a bigger surface and thereby faster degradation.

In particular embodiments, the coating comprises ethyl cellulose $C_{12}H_{23}O_6(C_{12}H_{22}O_5)_nC_{12}H_{23}O_5$, where n can vary to provide a wide variety of molecular weights. Ethylcellulose, an ethyl ether of cellulose, is a long-chain polymer of β-anhydroglucose units joined together by acetal linkages. Ethyl cellulose comes in different grades, which vary in molecular weight and number of ethoxy groups. In certain embodiments, the ethylcellulose is selected from one or more of grades from 20-300, which are commercially available. Grades with high molecular weights may also be used because they are optimal to give a hard shell (coating). The shell (coating) may comprise one or more ethyl celluloses with different grades. For example, the shell may include a first ethyl cellulose with a grade selected from a grade ranging from 20 to 300, a grade ranging from 20 to 100, a grade ranging from 20 to 40, and a grade of 20 and a second ethyl cellulose with a grade selected from a grade ranging from 20 to 300, a grade ranging from 50 to 200, a grade ranging from 80 to 120, and a grade of 100. Ethyl cellulose generally has a glass transition temperature within 129-133° C. These polymers are widely used in food and pharmaceutical industry as coater, stabilizer, matrix former and taste masking and are regarded as non toxic substances.

Cellulose based polymers are, in general, derived from plant material and may subsequently be modified. Many cellulose based polymers are cheap and give a good hardness when moulded. As derivatives of plants, cellulose based polymers are in general easily decomposable when disposed. These polymers are generally stable and inert when incorporated in solid dosage forms.

Synthetic Polymers

The coating used in a pharmaceutical composition as described herein may also comprise one or more synthetic polymers. Suitable synthetic polymers for use in the shell (coating) composition may, for example, be one or more selected from polyamide, polyethylene, polyethylene terephthalate, polypropylene, polyurethane, polyvinyl acetate, polyvinyl alcohol, polyvinyl butural, polyvinyl chloride,), Eudragit L methyl ester, Eudragit RL, Eudragit RS, Eudragit S and Eudragit E, silicone rubber, latex, teflon, copolymers such as ethylene vinyl acetate (EVA), styrene-butadienestyrene (SBS) and styrene-isoprene-styrene (SIS), Polyethylene glycols, polyvinylpyrrolidone, polyethylene oxide (ranging in molecular weights 100,000 to 8,000,000 daltons), carboxymethylene (Carbomer) and sugars thereof (e.g., allylsucrose,) and co-polymers of ethylene and propylene oxide (PoloXamer).

Biodegradable Polymers

Biodegradation is the process by which microorganisms (microbes such as bacteria, fungi or algae) convert materials into biomass, carbon dioxide and water. Biomass is a general term used to refer to the cells of the microorganisms that are using the material as a carbon source.

The coating used in the pharmaceutical compositions described herein may also comprise one or more biodegradable polymers. Said biodegradable polymer(s) may be one or more selected from starch based polymers as described herein above in this section and cellulose based polymers as described herein above in this section. The biodegradable polymer may also be one or more selected from polyhydroxybutyrate (PHB), polyhydroxyvalerate (PHV), polyhydroxyvalerate-co-hydroxyvalerate (PHV/VH), Polyhydroxylakanoates (PHA), poly-3-hydroxy-5-phenylvalerate (PHPV), aliphatic polyesters, polycaprolactone (PCL), polylactic acid (PLA), polyglycolic acid (PGA), copolymers or block copolymers of polycaprolactone (PCL), polylactic acid (PLA) and/or polyglycolic acid (PGA), poly-propylene carbonate (PPC), polyester amide (PEA), polybutylene succinate adipate (PBSA), polybutylene adipate co-terephtalate (PBAT) and polybutylene succinate-adipate (PESA).

Copolymers or block copolymers of polycaprolactone (PCL), polylactic acid (PLA) and/or polyglycolic acid (PGA) may, for example, be selected from poly(lactic-co-glycolic acid) (PLGA), polylactic acid and epsilon-caprolactone copolymer (PLA/CL) and polylactic acid/glycolic acid polymers) (PLA/GA), which are all commercially available.

In one embodiment, the coating comprises one or more biodegradable polymers selected from polylactic acid (PLA), polycaprolactone (PCL) and polyhydroxybutyrate (PHB), preferably the coating comprises both polylactic acid (PLA), polycaprolactone (PCL) and polyhydroxybutyrate (PHB).

The use of polycaprolactone and other polymers in this group has been increased over the last decade, while the demand for environmental friendly plastics has grown. These polymers are regarded as nontoxic and are already used in parenteral, pharmaceutical formulations. Such polymers can facilitate formulation of a more flexible shell (coating) when moulded in mixture with starch derived polymers. The somewhat rigid structure of pure thermoplastic starch may be adjusted as desired by inclusion polycaprolactone or other biodegradable polymers disclosed herein. Furthermore the biodegradable polymers are decomposable and disintegrate by microorganisms.

Polylactic Acid

Polylactic acid or polylactide (PLA) may be used in forming the coatings included in the pharmaceutical compositions described herein. PLA is biodegradable, thermoplastic, aliphatic polyester derived from renewable resources, such as corn starch. PLA belongs to the chemical family of polyesters, such as, for example, ε-caprolactone, PLA-caprolactone in different ratios 15% PLA to 100% (25, 35, 50, 75, 85%), polyglycolides, polyglycolic acids (PGA), poly(lactide-co-glycolide) in different ratios 15 to 100% PLA (25, 35, 50, 75, 85%), poly(lactide-co-glycolide)-OH in different ratios 15% PLA to 100% (25, 35, 50, 75, 85%). Each of the before mentioned polymers exist in L or D-form (making them optically active) and in equal amounts (1:1) of L- and D-forms results in an amorphous mixture, while the L- or D-forms possess a certain degree of crystallinity. The degree of crystallinity is related to the mechanical properties (including processability) and physico-chemical properties, such as stability, of the polymer. The form and level of crystallinity or extent of amorphous characteristics of such polymers can therefore be selected to enhance one or more of processability, mechanical attributes of the pharmaceutical composition, or stability of an active drug substance or the pharmaceutical composition itself. Therefore, with PLA, the degree of crystallinity can be selected and optimized for a particular application. Each degree of crystallinity has different mechanical properties, thus, for example, adhesion of the polymer material to the matrix may vary depending on the degree of crystallinity of the given material (PLA).

The skeletal structure of PLA is shown below.

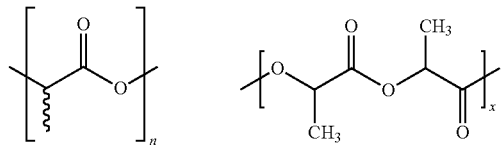

Due to the chiral nature of lactic acid, several distinct forms of polylactide exist: poly-L-lactide (PLA in its L-form), referred to as PLLA, is the product resulting from polymerization of L,L-lactide (also known as L-lactide), and poly-D-lactide (PLA in its D-form) referred to as PDLA is the product resulting from polymerization of L,L-lactide (also known as L-lactide). Furthermore, PLLA and PDLA may be mixed with various ratios of the two stereo forms. The L-form generally has more robust mechanical properties than the D-form and the L-form has been typically used in pharmaceutical products. In order to achieve mechanical or other properties that may not be obtained through use of a D-form or L-form alone, targeted properties of a shell (coating) may, in some embodiments, be achieved by blending the D-form to the L-form. For example, in some such embodiments, the D-form may be added to the L-form in amounts of 5, 10, 20, 30, 40% w/w, up to a ratio of 1:1. Blending of the D-form with the L-Form may result in a completely amorphous material or, alternatively, such blending may also form a highly regular stereo complex with increased crystallinity, since addition of PDLA increases the molecular energy of the mixture by forming a concentration gradient. PLA in its L-form has a crystallinity of around 35-45%, a glass transition temperature between 35-80° C. and a melting temperature between 173-178° C.

Due to the structure of PLA, PLA may be exposed to hydrolysis during its path through the gastro-intestinal tract. However PLA is impermeable and insoluble in aqueous media, and in relation to applying PLA as shell (coating) material, shells (coatings) formed using PLA, at least macroscopically, have proven to remain intact within the first 48 hours of exposure. Furthermore, the possible degradation product of PLA is merely lactic acid.

Polyglycols

The coating used in the pharmaceutical compositions described herein may also comprise any of the above-mentioned polyglycols in a form, which erodes at a substantially slower rate than the matrix composition. The coating may thus be one which is eroded in an aqueous medium at a substantially slower rate than the matrix composition comprising the active drug substance, whereby a substantially controlled area of the matrix composition comprising the active drug substance is exposed during erosion and/or release of the matrix composition, and whereby the coating is substantially eroded upon erosion and/or release of the matrix composition comprising the active drug substance. Such a coating may be designed so that its longitudinal erosion rate is substantially the same as the longitudinal erosion and/or release rate of the matrix, whereby the matrix and the coating will erode longitudinally towards the centre of the composition at substantially the same rate. Thus, in such embodiments, when the matrix composition has been completely eroded and/or released by the aqueous medium, the coating will also be substantially completely eroded. A matrix composition having such a coating has the advantage of being completely biodegraded upon release of the active drug substance.

A polyglycol suitable for inclusion in a coating used in a pharmaceutical composition as described herein is high molecular weight PEO, such as a PEO with an average molecular weight which is significantly higher than the average molecular weight of any of the PEOs contained in the matrix composition. Thus, for any given pharmaceutical composition it is preferred that any PEO contained in the shell (coating) has a significantly higher average molecular weight than any PEO contained in the matrix. Accordingly, where the coating comprises one or more PEO, in certain embodiments, the average molecular weight of the PEO may be selected from at least 900,000 daltons, at least 2,000,000 daltons, at least 4,000,000 daltons, and at least 6,000,000 daltons. In a particular embodiment, the coating includes a PEO having a molecular weight of about 7,000,000 daltons.

Mixtures of Polymers

As noted herein above the coating may comprise one or more different polymers. In some embodiments, the coating may comprise one or more different polymers selected from starch based polymers, cellulose based polymers, synthetic polymers and biodegradable polymers described herein.

In one embodiment, the coating comprises polymers selected from starch based polymers and biodegradable polymers. In one such embodiment the polymers may be selected from any of the starch based polymers and biodegradable polymers described herein above in this section. In particular, biodegradable polymers such as polycaprolactone, polyhydroxybuturate, polyhydroxyvalerate, polylactic acid, polyhydroxyalkanoates and/or polypropylenecarbonate can be blended with various starches (such as any of the starches described herein above in this section) in different ratios. Suitable mixtures for use in the shell (coating) composition are, for example, polycaprolactone and sago and/or cassava starch, polycaprolactone or polyhydroxybuturate and predried, thermoplastic starch, polycaprolactone and gelatinized starch or thermoplastic starch. Other suitable mixtures include starch-based blends with biodegradable thermoplastic components like polyester amide, polyhydroxybuturate-co-valerate or polybutylene succinate-adipate. Polymers starches can be cross-linked with Maleic anhydride (MA) and dicumyl peroxide (DCP) giving harder items when moulded.

In another embodiment, the coating may comprise polymers selected from starch based polymer and synthetic polymers. In particular such embodiments, the coating comprises polymers selected from any of the starch based polymers and synthetic polymers described herein above in this section. Suitable mixtures for use in the shell (coating) composition include, for example, native granular starch, modified starch, plasticized starch blended or grafted with many synthetic polymers such as polyethylene, polystyrene, Purified Terephthalic acid (PTA), optionally in mixture with aliphatic polyesters or polyvinyl alcohols in different ratios. Polybutylene succinate (PBS), polybutylene succinate adipate in blend with various starches in different ratios are also suitable such as, for example, Polybutylene succinate in mixture with thermoplastic starch, and alkylene oxide modified starches in combination with hydrolyzed polyvinyl alcohol.

In yet another embodiment, the coating may comprise polymers selected from cellulose based polymers and biodegradable polymers, such as, for example, any of the cellulose based polymers and biodegradable polymers described herein above in this section. Thus, the coating may for example comprise a mixture of PLA and ethylcellulose. In a specific embodiment, the coating consists of PLA, ethyl cellulose, one or more plasticizers (such as any of the plasticizers described herein below) and one or more UV stabilisers (such as any of the UV stabilisers described herein below).

UV Stabiliser

Radiation from sunlight can accelerate the degradation of plastics, such as the shell (coating) described herein. The packaging material to protect the pharmaceutical compositions (e.g., tablets) from direct sunlight may not be enough protection. Especially for a shell (coating) with high concentration of biodegradable polymers, it may be useful to add UV-stabilizers to the compositions, due to many unsaturated functional groups (e.g., carbonyl groups). UV-stabilizers may be, selected from, for example, titanium dioxide, metal complexes with sulfur containing groups, hindered amine light stabilisers (HALS), benzophenones, benzotriazoles. Titanium dioxide is already widely used in pharmaceutical preparations as pigment and is considered non toxic.

Plasticizer

In addition to above mentioned polymers, the coating may comprise one or more additional components. Thus, the coating may comprise at least one selected from the group consisting of i) polymers which are soluble or dispersible in water,
ii) plasticizers, and
iii) fillers in some embodiments the polymers, which are soluble or dispersible in water, are cellulose derivatives, which are soluble or dispersible in water. Thus, the shell (coating) material may comprise one or more plasticizers, preferably, any of the plasticizers described herein above in the section "pharmaceutically acceptable excipients" and/or any of the plasticizers described below. Where a plasticizer is included, the shell (coating) material may include one or more of the following plasticizers: Cetostearyl alcohol, castor oil, dibutyl sebacate, polyethylene oxides and/or PoloXamer. However other plasticizers may also be used to provide desired material properties.

Other suitable plasticizers may be selected from mono- and di-acetylated monoglycerides, diacetylated monoglycerides, acetylated hydrogenated cottonseed glyceride, glyceryl cocoate, Polyethylene glycols or polyethylene oxides (e.g., with a molecular weight of about 1,000-500,000 daltons), dipropylene glycol salicylate glycerin, fatty acids and esters, phthalate esters, phosphate esters, amides, diocyl phthalate, phthalyl glycolate, mineral oils, hydrogenated vegetable oils, vegetable oils, acetylated hydrogenated soybean oil glycerides, Castor oil, acetyl tributyl citrate, acetyl triethyl citrate, methyl abietate, nitrobenzene, carbon disulfide, β-naphtyl salicylate, sorbitol, sorbitol glyceryl tricitrate, fatty alcohols, cetostearyl alcohol, cetyl alcohol, stearyl alcohol, oleyl alcohol, myristyl alcohol, sucrose octaacetate, alfa-tocopheryl polyethylene glycol succinate (TPGS), tocopheryl derivative, diacetylated monoglycerides, diethylene glycol monostearate, ethylene glycol monostearate, glyceryl monooleate, glyceryl monostearate, propylene glycol monostearate, macrogol esters, macrogol stearate 400, macrogol stearate 2000, polyoxyethylene 50 stearate, macrogol ethers, cetomacrogol 1000, lauromacrogols, nonoxinols, octocinols, tyloxapol, poloxamers, polyvinyl alcohols, polysorbate 20, polysorbate 40, polysorbate 60, polysorbate 65, polysorbate 80, polysorbate 85, sorbitan monolaurate, sorbitan monooleate, sorbitan monopalmitate, sorbitan monostearate, sorbitan sesquioleate, sorbitan trioleate, sorbitan tristearate and sucrose esters, amyl oleate, butyl oleate, butyl stearate, diethylene glycol monolaurate, glycerol tributyrate, Flexol B-400, monomeric polyethylene ester, Piccolastic A-5, Piccalastic A-25, Clorafin 40, acetyl tributyl citrate, acetyl triethyl citrate, benzyl benzoate, butoxyethyl stearate, butyl and glycol esters of fatty acids, butyl diglycol carbonate, butyl ricinoleate, butyl phthalyl butyl glycolate, camphor, dibutyl sebacate, dibutyl tartrate, diphenyl oxide, glycerine, HB-40, hydrogenated methyl ester of rosin, methoxyethyl oleate, monoamylphthalate, Nevillac 10, Paracril 26, technical hydroabietyl alcohol, triethylene glycol dipelargonate, solid aliphatic alcohols and mixtures thereof.

In certain embodiments, the shell (coating) is made of a material, wherein the concentration of plasticizer is from 0 to 30% w/w. In particular such embodiments, the shell comprises one or more plasticizer(s) and one or more polymer(s). In further such embodiments, the shell consists essentially of one or more plasticizer(s) and one or more polymer(s).

Furthermore, the coating may comprise sweetening agents, flavouring agents and/or colouring agents, which may be any of the sweetening agents, flavouring agents and/or colouring agents described herein above in the section "pharmaceutically acceptable excipients".

In particular embodiments, the shell (coating) may be made of a material comprising a single polymer material, and wherein the concentration of the polymer is from 5 to 100% w/w.

In other embodiments, the shell (coating) may be made of a material comprising a mixture of polymers, and wherein the total concentration of polymers is from 70 to 100% w/w.

In yet further embodiments, the coating comprises an amount of one or more polymers selected from at least 50% w/w, at least 60% w/w, at least 70% w/w, and at least 80% w/w, wherein said one or more polymers are substantially insoluble in water as described herein above.

Thus, in specific embodiments, wherein the coating comprises cellulose derivatives (such as ethyl cellulose), then the coating may comprise cellulose derivatives in an amount selected from at least 50% w/w, at least 60% w/w, at least 70% w/w, at least 80% w/w, at least 85% w/w. In one such embodiment, the coating comprises 87% w/w of a cellulose derivative polymer material (such as ethyl cellulose).

In certain embodiments, the coating comprises an amount of plasticizer selected from at the most 19% w/w, at the most 15% w/w, and at the most 12% w/w. In one such embodiment, the coating comprises at the most 12% w/w plasticizer (such as cetostearyl alcohol).

In still further embodiments, wherein the coating comprises biodegradable polymers (such as polylactic acid), then the coating may include the biodegradable polymer material in an amount selected from at least 50% w/w, at least 60% w/w, at least 70% w/w, at least 80% w/w, and at least 85% w/w. In one such embodiment, the coating comprises 86% w/w biodegradable polymer material (such as polylactic acid).

In s additional embodiments, the coating comprises an amount of plasticizer selected from at the most 20% w/w, at the most 17% w/w, and at the most 15% w/w. In one such embodiment, the coating comprises 14% w/w plasticizer (polyethylene oxides 200,000 daltons).

Outer Coat

In some cases the pharmaceutical composition of the present invention may also comprise an outer coat that fully covers the pharmaceutical composition (fully covers both the matrix composition and the coating or shell). Said outer coat may be selected from the group consisting of task masking coats, coats with aqueous moisture barriers and/or oxidative barriers to improve the stability of the composition, and cosmetic coats, such as, for example, a coat containing colouring agents, sweetening agents and/or flavouring agents in order to provide an elegant and palatable tablet and/or to easy distinguishable dose strengths. It can be particularly useful to coat compositions having different dose strengths or active drug substances with outer coats of different colours so that the different actives and dose strengths are easily distinguished. Where provided, the outer coat will typically be easily soluble in aqueous media in order to facilitate contact of the matrix composition with the surrounding aqueous media via the openings in the coating rapidly after administration.

Pharmaceutical Compositions

In particular embodiments, pharmaceutical compositions as described herein comprise: an active drug selected from oxycodone, hydrocodone, hydromorphone, norhydrocordone, oxymorphone, noroxycodone, morphine, morphine-6-glucuronode and pharmaceutically acceptable salts thereof, such as morphine sulphate, morphine sulphate pentahydrate, oxycodone hydrochloride, hydrocodone bitartrate and hydromorphone hydrochloride; at least one polyglycol selected from polyethyleneglycol and polyethylene oxide and any mixtures thereof; and a coating comprising (i) a material selected from ethyl cellulose, polylactic acid, polycaprolactone, polyhydroxy butyrate and polyethylene oxide and any mixtures thereof, (ii) a plasticizer selected from the group consisting of poloxamer, polyethylene oxide, cetostearyl alcohol, castor oil and dibutyl sebacate and any mixtures thereof, and (iii) a filler, which is titanium dioxide.

In further embodiments, pharmaceutical compositions as described herein comprise: an active drug selected from morphine, oxycodone, hydrocodone, hydromorphone, norhydrocordone, oxymorphone, noroxycodone, morphine-6-glucuronode and pharmaceutically acceptable salts thereof, such as morphine sulphate, morphine sulphate pentahydrate, oxycodone hydrochloride, hydrocodone bitartrate and hydromorphone hydrochloride; at least one polyglycol selected from polyethyleneglycol and polyethylene oxide and any mixtures thereof; at least one plasticizer which is poloxamer; at least one stabilizer selected from mannitol, butylated hydroxytoluene and Vitamin E Polyethylene Glycol Succinate, Eudragit L, Eudragit RL, Eudragit RS, Eudragit E, Eudragit S, and at least one gelling agent selected from the group consisting of carrageenan and hydroxypropylmethylcellulose; and a coating material comprising (i) a material selected from ethyl cellulose, polylactic acid, polycaprolactone and polyethylene oxide and any mixtures thereof, (ii) a plasticizer selected from polyethylene oxide and cetostearyl alcohol and any mixtures thereof, and (iii) a filler, which is titanium dioxide.

In cases where the pharmaceutical composition also comprises an outer coat, in specific embodiments, the pharmaceutical composition as described herein may comprise: an active drug substance selected from morphine, oxycodone, hydrocodone, hydromorphone, norhydrocordone, oxymorphone, noroxycodone, morphine-6-glucuronode and pharmaceutically acceptable salts thereof, such as morphine sulphate, morphine sulphate pentahydrate, oxycodone hydrochloride, hydrocodone bitartrate and hydromorphone hydrochloride; at least one polyglycol selected from polyethyleneglycol and polyethylene oxide and any mixtures thereof; and a coating comprising (i) a material selected from ethyl cellulose, polylactic acid, polycaprolactone, polyhydroxy butyrate and polyethylene oxide, and any mixtures thereof, (ii) a plasticizer selected from poloxamer, polyethylene oxide, cetostearyl alcohol, castor oil and dibutyl sebacate and any mixtures thereof, and (iii) a filler, which is titanium dioxide; and an outer coat selected from task masking coats, coats with aqueous moisture barriers and/or oxidative barriers, cosmetic coats, and any mixtures thereof.

In a specific embodiment the pharmaceutical composition includes a matrix composition comprising morphine sulphate as the active drug substance, a mixture of polyethylene oxide 200,000 and polyethylene oxide 300,000 as polyglycols, poloxamer as a plasticizer, mannitol as a stabilizer, a mixture of carrageenan and hydroxypropylmethylcellulose as gelling agents, and butylated hydroxytoluene as antioxidant and a coating disposed over the matrix composition comprising a mixture of polylactic acid and polyethylene oxide.

In another specific embodiment the pharmaceutical composition comprises a matrix composition that comprises morphine sulphate as the active drug, a mixture of polyethylene oxide 200,000 and polyethylene oxide 300,000 as polyglycols, poloxamer as a plasticizer, mannitol as a stabilizer, and butylated hydroxytoluene as an antioxidant and a coating disposed over the matrix composition comprising a mixture of polylactic acid and polyethylene oxide.

In yet another specific embodiment, the pharmaceutical composition comprises a matrix composition comprising morphine sulphate as the active drug, polyethylene oxide 300,000 as a polyglycol, poloxamer as a plasticizer, and a mixture of mannitol and butylated hydroxytoluene as stabilizers and a coating disposed over the matrix composition comprising a mixture of ethylcellulose, cetostearyl alcohol and titanium dioxide.

In still another specific embodiment, the pharmaceutical composition includes a matrix composition comprising morphine sulphate as the active drug, polyethylene oxide 200,000 as a polyglycol, and a mixture of mannitol and Vitamin E Polyethylene Glycol Succinate as stabilizers and a coating disposed over the matrix composition comprising a mixture of ethylcellulose, cetostearyl alcohol and titanium dioxide.

In another specific embodiment the pharmaceutical composition includes a matrix composition comprising oxycodone hydrochloride as the active drug, a mixture of polyethylene oxide 200,000 and polyethylene oxide 300,000 as polyglycols, poloxamer as a plasticizer, Eudragit as a stabilizer, hydroxypropylmethylcellulose as a gelling agent, and butylated hydroxytoluene as an antioxidant and a coating disposed over the matrix composition comprising a mixture of polylactic acid and polyethylene oxide.

In another embodiment, the pharmaceutical composition includes a matrix composition comprising oxycodone hydrochloride as the active drug, a mixture of polyethylene oxide 200,000 and polyethylene oxide 300,000 as polyglycols, poloxamer as a plasticizer, Eudragit as a stabilizer, and butylated hydroxytoluene as an antioxidant and a coating disposed over the matrix composition comprising a mixture of polylactic acid and polyethylene oxide.

In yet another embodiment, the pharmaceutical composition includes a matrix composition comprising oxycodone hydrochloride as the active drug, a mixture of polyethylene oxide 200,000 and polyethylene oxide 300,000 as polyglycols, poloxamer as a plasticizer, Eudragit as a stabilizer, and butylated hydroxytoluene as an antioxidant and a coating disposed over the matrix composition comprising a mixture of ethylcellulose, cetostearyl alcohol and titanium dioxide.

In still another embodiment the pharmaceutical composition includes a matrix composition comprising hydrocodone bitartrate as the active drug, a mixture of polyethylene oxide 200,000 and polyethylene oxide 300,000 as polyglycols, poloxamer as a plasticizer, hydroxypropylmethylcellulose as a gelling agent, and butylated hydroxytoluene as an antioxidant and a coating disposed over the matrix composition comprising a mixture of polylactic acid and polyethylene oxide.

In yet another embodiment, the pharmaceutical composition includes a matrix composition comprising hydrocodone bitartrate as the active drug, a mixture of polyethylene oxide 200,000 and polyethylene oxide 300,000 as polyglycols, poloxamer as a plasticizer, and butylated hydroxytoluene as an antioxidant and a coating disposed over the matrix composition comprising a mixture of polylactic acid and polyethylene oxide.

In another embodiment, the pharmaceutical composition includes a matrix composition comprising hydrocodone bitartrate as the active drug, a mixture of polyethylene oxide 200,000 and polyethylene oxide 300,000 as polyglycols, poloxamer as a plasticizer, and butylated hydroxytoluene as a stabilizer and a coating disposed over the matrix composition comprising a mixture of ethylcellulose, cetostearyl alcohol and titanium dioxide.

In another embodiment the pharmaceutical composition includes a matrix composition comprising hydromorphone hydrochloride as the active drug, a mixture of polyethylene oxide 200,000 and polyethylene oxide 300,000 as polyglycols, poloxamer as a plasticizer, hydroxypropylmethylcellulose as a gelling agent, and butylated hydroxytoluene as an antioxidant and a coating disposed over the matrix composition comprising a mixture of polylactic acid and polyethylene oxide.

In another embodiment the pharmaceutical composition includes a matrix composition comprising hydromorphone hydrochloride as the active drug, a mixture of polyethylene oxide 200,000 and polyethylene oxide 300,000 as polyglycols, poloxamer as a plasticizer, and butylated hydroxytoluene as an antioxidant and a coating disposed over the matrix composition comprising a mixture of polylactic acid and polyethylene oxide.

In still another embodiment, the pharmaceutical composition includes a matrix composition comprising hydromorphone hydrochloride as the active drug, a mixture of polyethylene oxide 200,000 and polyethylene oxide 300,000 as polyglycols, poloxamer as a plasticizer, and butylated hydroxytoluene as an antioxidant and a coating disposed over the matrix composition comprising a mixture of ethylcellulose, cetostearyl alcohol and titanium dioxide.

Administration

The pharmaceutical composition according to the invention can be designed for oral administration. For example, the pharmaceutical compositions described herein may be produced as unit dosage forms, such as, for example, tablets, for oral intake by swallowing one or more intact units of the pharmaceutical composition.

Due to the possibility of controlling the release profile of the active drug substance, the pharmaceutical composition may be adapted for oral administration 1-6 times a day, normally 1-4 times daily, such as 1-3 times, 1-2 times or 1 time daily. In one such embodiment, a pharmaceutical composition as described herein comprising one or more unit dosage forms, is administered once or twice daily. In yet another embodiment, a pharmaceutical composition as described herein comprising one or more unit dosage forms is administered once daily.

In one embodiment, the pharmaceutical composition is prepared in unit dosage forms, such that a desired dose of the active drug substance is included within one unit dosage form, wherein the dose is selected for administration with an interval of in the range of about 20 to 28 hours, such as a 24 hour interval. The pharmaceutical composition may, in certain embodiments, be in the form of tablets. In specific such embodiments, each tablet may comprise one dose of the active drug substance, wherein the dose is selected for administration at an interval of in the range of about 20 to 28 hours, such as a 24 hour interval.

Furthermore, the pharmaceutical compositions described herein may be prepared for continued administration, wherein dosages are preferably administered with an interval of in the range of about 20 to about 28 hours, such as about 24 hours. The pharmaceutical compositions described herein can be prepared to deliver clinically effective amounts of active drug substance for at least 24 hours after intake. In particular embodiments, wherein the pharmaceutical compositions are for treatment of pain, then the pharmaceutical compositions may be formulated to relieve or ameliorate pain for a period of time selected from 20, 22, 24, 26, and 28 hours after intake. In one such embodiment, pharmaceutical compositions as described herein for treatment of pain, and are formulated to relieve or ameliorate pain for at least 24 hours after intake.

Pharmaceutical compositions as described herein are, in specific embodiments, prepared for continued administration, and accordingly, the composition is prepared for repeated administration with an interval of in the range of about 20 to about 28 hours, such as about 24 hours between administrations. In such embodiments, the continued administration may be administration over several days. In particular embodiments, administration of the pharmaceutical compositions may take place over a period of time selected from at least 3 days, at least 4 days, at least 5 days, at least 6 days, at least 7 days, at least 9 days, at least 11 days, at least 14 days, and at least 30 days, wherein the pharmaceutical composition is continuously administered at intervals in the range of about 20 to 28 hours, such as a 24 hour interval. In one such embodiment, the pharmaceutical composition is administered to a patient in need thereof at intervals of about 20 to about 28 hours, such as about 24 hour intervals, over a period of time selected from at least 3 days, at least 4 days, at least 5 days, at least 6 days, at least 7 days, at least 9 days, at least 11 days, at least 14 days, and for at least 30 days. Continued administration may be carried out over a period of time that is at least sufficient to arrive at steady state in the individual to whom the pharmaceutical composition of the invention is being administered.

The pharmaceutical compositions described herein can be prepared for delivery of desired dosage active drug substance. The dosage will be dependent on the individual to whom the pharmaceutical composition of the invention is being administered and the active drug substance.

In particular embodiments, the dosage for each administration, wherein dosages are prepared for administration with an interval of in the range of about 20 to 28 hours, such as a 24 hour interval, is in the range of 1 to 1000 mg, such as in the range of 10 to 1000 mg, for example in the range of 30 to 1000 mg, such as in the range of 1 to 750 mg, for example in the range of 1 to 500 mg, such as in the range of 1 to 250 mg. In certain such embodiments, the dosage for each administration is in a range selected from 10 to 500 mg and 10 to 240 mg of an active drug substance.

In particular, when the active drug substance included in the pharmaceutical compositions is an opioid, and more particularly, when the active drug substance is morphine or a pharmaceutically acceptable salt thereof, then, in specific embodiments, the daily dosage may be selected from a range of 1 to 1000 mg, a range of 10 to 1000 mg, a range of 15 to 1000 mg, a range of 1 to 750 mg, a range of 1 to 500 mg, a range of 1 to 250 mg, a range of 10 to 500 mg, a range of 15 to 240 mg, a range of 15 to 200 mg, and a range of 30 to 200 mg. In certain such embodiments, the pharmaceutical composition includes morphine or a pharmaceutically acceptable salt thereof as an active drug substance and the daily dosage of morphine or a pharmaceutically acceptable salt thereof is selected from 15, 20, 30, 45, 60, 75, 90, 100, 120, 140, 160, 180 or 200 mg.

In particular, when the active drug substance included in the pharmaceutical compositions is an opioid, and more particularly, when the active drug substance is oxycodone or a pharmaceutically acceptable salt thereof, then, in specific embodiments, the daily dosage may be selected from a range of 1 to 1000 mg, a range of 10 to 1000 mg, a range of 30 to 1000 mg, a range of 10 to 500 mg, a range of 10 to 250 mg, a range of 10 to 200 mg, a range of 10 to 50, a range of 10 to 500 mg, a range of 10 to 160 mg, a range of 10 to 100 mg, a range of 10 to 80 mg, a range of 20 to 80 mg, a range of 40 to 80 mg, and a range of 30 to 50 mg. In certain such embodiments, the pharmaceutical composition includes oxycodone or a pharmaceutically acceptable salt thereof as an active drug substance and the daily dosage of oxycodone or a pharmaceutically acceptable salt thereof is selected from 10, 15, 20, 30, 40, 50, 60, 70, 80, 90, 100 or 160 mg.

In particular, when the active drug substance included in the pharmaceutical compositions is an opioid, and more particularly, when the active drug substance is hydrocodone or a pharmaceutically acceptable salt thereof, then, in specific embodiments, the daily dosage may be selected from a range of 1 to 1000 mg, a range of 10 to 1000 mg, a range of 15 to 1000 mg, a range of 1 to 750 mg, a range of 1 to 500 mg, a range of 1 to 250 mg, a range of 1 to 100 mg, a range of 1 to 30 mg, a range of 10 to 500 mg, a range of 10 to 200 mg, a range of 10 to 160 mg, a range of 10 to 30 mg, a range of 20 to 160 mg, and a range of 20 to 80 mg. In certain such embodiments, the pharmaceutical composition includes hydrocodone or a pharmaceutically acceptable salt thereof as an active drug substance and the daily dosage of hydrocodone or a pharmaceutically acceptable salt thereof is selected from 10, 20 30, 40, 50, 60, 70, 80, 100, 120, 140, 160 mg.

In particular, when the active drug substance included in the pharmaceutical compositions is an opioid, and more particularly, when the active drug substance is hydromorphone or a pharmaceutically acceptable salt thereof, then, in specific embodiments, the daily dosage may be selected from a range of 1 to 1000 mg, a range of 1 to 500 mg, a range of 1 to 250 mg, a range of 1 to 100 mg, a range of 2 to 250 mg, a range of 2 to 100 mg, a range of 4 to 100 mg, a range of 4 to 80 mg, and a range of 4 to 64 mg. In certain such embodiments, the pharmaceutical composition includes hydromorphone or a pharmaceutically acceptable salt thereof as an active drug substance and the daily dosage of hydromorphone or a pharmaceutically acceptable salt thereof is selected from 2, 4, 6, 8, 10, 12, 14, 16, 18, 20, 24, 28, 32, 40, 48, 56, 64, 72 or 80 mg.

Above-mentioned dosages are in particular relevant when the individual in need of treatment is a human being, such as an adult human being.

Individuals in Need of Treatment

The pharmaceutical composition of the invention is prepared for administration to an individual in need thereof. Said individual may be a mammal, and in specific embodiments the individual is a human being.

In certain embodiments, the pharmaceutical composition is for continuous treatment of pain and accordingly, the individual in need of treatment is an individual suffering from pain. In particular such embodiments, the individual is an individual suffering from pain for a prolonged period of time requiring continuous treatment, wherein continuous treatment is as described herein.

In embodiments of the invention, wherein the active drug substance is an opioid, such as oxycodone, hydrocodone, morphine or pharmaceutically acceptable salts thereof, then the pharmaceutical compositions are suitable for treatment of moderate to severe pain such as severe pain.

Examples of individuals, who may benefit from treatment with the pharmaceutical compositions according to the invention include, for example, the following:

The individual may be an individual suffering from chronic pain, such as moderate to severe chronic pain;

The individual may be an individual suffering from cancer and the pharmaceutical composition may be useful for continuous treatment of pain or even moderate to severe pain, such as severe pain in an individual suffering from cancer;

The individual may also be an individual who has suffered a moderate to severe injury;

The individual may be an individual suffering from pain associated with surgical conditions, such as a pre-surgical individual (an individual in need of surgery) or a post surgical individual (an individual who has undergone surgery);

The individual may also be an individual suffering from or having suffered from a myocardial infarction, sickle cell crises, kidney stone or severe back pain;

The individual may also be an individual suffering from degenerative pain, herniated disc pain, fibromyalgia, neuropathic pain and/or nociceptive pain; and The individual may also be an individual suffering from arthritis, such as arthritis osteo, arthritis rheumatoid, arthritis psoriatica and/or arthritis urica.

Pharmacokinetics

The pharmaceutical compositions described herein are useful for continued administration of an active drug substance over an interval of about 20 to about 28 hours between individual administrations, and accordingly, in particular embodiments, pharmaceutical compositions as described herein have the pharmacokinetic profiles described in this section. Accordingly, in specific embodiments, upon administration, pharmaceutical compositions according to the present description give rise to a ratio between trough (or $C_{24}$ in embodiments wherein the pharmaceutical composition is for continued administration with an interval of 24 hours between individual administrations) and $C_{max}$, which is sufficiently high. In particular embodiments the pharmaceutical compositions described herein, upon administration to an individual, do not reach the maximal concentration of the active drug substance too soon. For example, in such embodiments, 50% of $C_{max}$ is not reached too soon after the $C_{max}$, and in certain such embodiments, 50% of $C_{max}$ is never reached because the trough/$C_{max}$ ratio is >0.5. In yet further embodiments, pharmaceutical compositions as described herein, when administered frequently enough to reach steady state, the trough provided by the pharmaceutical composition is sufficiently high to ensure continuous efficacy over the entire administration period.

An individual is in steady state with regard to a particular active drug substance when the plasma concentration level after one dosing is the same within the standard deviation as the plasma concentration level after the following dosing. Thus, for pharmaceutical compositions for continued administration with a 24 hour interval between individual administrations, steady state $AUC_{(0-24h)d} = AUC_{(0-24h)d+1} +/-$ the standard deviation, and $C_{max(0-24h)d} = C_{max(0-24h)d+1} +/-$ the standard deviation, where d is day. AUC refers to the "area under the curve" and is a measurement for the plasma concentration over the entire dosing interval.

In order to determine steady state parameters, pharmaceutical compositions as described herein may be administered for a sufficient amount of time to reach steady state. However, theoretical steady state parameters may be determined by a simulation based on information on serum concentration of an active drug substance or its metabolites after a single administration. Such a simulation may for example be prepared as described in Example 1 or Example 2 herein below.

Thus, in some embodiments, the pharmaceutical compositions described herein have a length in a range selected from 7.5 to 15 mm and 8 to 10 mm, said compositions comprise an active drug substance (e.g., an analgesic, such as an opioid, for example morphine, oxycodone or hydrocodone) described herein, and upon administration, the pharmaceutical compositions, provide an average steady state trough (such as the theoretical steady state trough) of the active drug substance selected from at least 30%, at least 35%, and at least 40% of the average steady state $C_{max}$ of the active drug substance. In certain such embodiments, upon administration, the pharmaceutical compositions, provide an average steady state trough of the active drug substance selected from a range of 30% to 80%, a range of 35 to 80%, and a range of 40 to 80% of the average steady state $C_{max}$ of the active drug substance. Again, in such embodiments, the active drug substance maybe an opioid such as those described herein. In one such embodiment, the opioid is hydrocodone or a pharmaceutically acceptable salt thereof.

In some embodiments; the pharmaceutical compositions described herein have a length in a range selected from 7.5 to 15 mm and 8 to 10 mm, said compositions comprise an active drug substance (for example, an analgesic, such as an opioid, for example morphine, oxycodone or hydrocodone) described herein, and upon administration, the pharmaceutical compositions, provide an average steady state trough (such as the theoretical steady state trough) of the active drug substance selected from at least 20%, at least 25%, and at least 30% of the average steady state $C_{max}$ of the active drug substance. In certain such embodiments, upon administration, the pharmaceutical compositions, provide an average steady state trough of the active drug substance selected from a range of 20% to 80%, a range of 25 to 80%, and a range of 30 to 80% of the average steady state $C_{max}$ of the active drug substance. Again, in such embodiments, the active drug substance maybe an opioid such as those described herein. In one such embodiment, the opioid is oxycodone or a pharmaceutically acceptable salt thereof.

In some embodiments, the pharmaceutical compositions described herein have a length in a range selected from 7.5 to 15 mm and 7.5 to 10 mm, said compositions comprise an active drug substance (for example, an analgesic, such as an opioid, for example morphine, oxycodone or hydrocodone) described herein, and upon administration, the pharmaceutical compositions, provide a steady state $C_{24}$ of the active drug substance selected from at least 20%, at least 25%, at least 30%, at least 40%, and at least 50% of steady state $C_{max}$ of the active drug substance. In such embodiments, the active drug substance maybe an opioid such as those described herein. In one such embodiment, the opioid is morphine.

The average steady state maybe based on measurements in at least 5 different individuals, such as 5 different human beings. Similarly, said average steady state trough may be based on measurements in at least 5 different individuals, such as 5 different human beings.

In respect of the pharmaceutical compositions formulated for continued administration with a 24 hour interval between administrations, then trough will in general be similar too, or even identical to steady state $C_{24}$.

In particular embodiments, upon administration of the pharmaceutical compositions described herein (in particular, such compositions which have a length of 7.5 to 15 mm such as, for example, a length of between about 8 to 10 mm), $C_{min}$ is preferably not reached too early after $C_{max}$. Thus, in such embodiments, $C_{min}$ is reached no earlier than half way through a given dosing interval in a steady state individual. Thus, in particular embodiments, where the pharmaceutical compositions are prepared for continued administration of an active drug substance (for example, an analgesic, such as an opioid, including for example, morphine, oxycodone or hydrocodone) over an interval of about 20 to 28 hours, such as a 24 hour interval, between administrations, $C_{min}$ may be reached at a time selected from no earlier than 10 hours after, no earlier than 12 hours after, no earlier than 14 hours after, at least 16 hours after, at least 18 hours after the last administration to an individual, such as a human being. In specific such embodiments, the time when $C_{min}$ is reached is determined as an average based on measurements in at least 5 different individuals, such as 5 human beings.

In embodiments of the pharmaceutical compositions described herein, the pharmaceutical compositions, after administration, provide a plasma concentration of the active drug substance that reaches 50% of steady state $C_{max}$ twice after each administration. Once at the time when plasma concentration is rising soon after administration (referred to 1$^{st}$ point), and once when plasma concentration is decreasing after the peak concentration has been reached (referred to as 2$^{nd}$ point).

For continued administration of an active drug substance over period of time of about 20 to 28 hours, such as a 24 hour interval, in certain embodiments, the pharmaceutical compositions described herein provide a pharmacological profile of the active drug substance (for example, an analgesic, such as an opioid, including, for example, morphine, oxycodone or hydrocodone), wherein the 2$^{nd}$ point where the plasma concentration reaches 50% of steady state $C_{max}$ is not reached too fast or even not at all. In certain such embodiments, the pharmaceutical composition described herein is a composition which exhibits a length selected from a range of 7.5 to 15 mm and a range of 8 to 15 mm. Additionally, fast onset of action for the active drug substance may be an advantage. Therefore, in particular embodiments, the pharmaceutical compositions described herein are formulated such that, after administration to an individual, the pharmaceutical composition provides a pharmacological profile of the active drug substance with a short time to the 1$^{st}$ point where the plasma concentration reaches 50% of steady state $C_{max}$. Depending on the active drug substance to be delivered and the desired pharmacological profile, after the initial administration of the pharmaceutical composition and during a period of continuous administration of the pharmaceutical composition, 50% of steady state $C_{max}$ may not be reached a second time until administration of the pharmaceutical composition is terminated. In such a situation, if desired, another marker, such as, for example, 75% of steady state $C_{max}$ may be chosen to define the period for the passing the first and second time.

Pharmaceutical compositions as described herein are able to both provide a profile with a high minimum plasma concentration ($C_{min}$) and a long time between the first and second time of passing a fraction of $C_{max}$ (e.g., 50% or 75% $C_{max}$) and as compared to other controlled release formulations. In particular embodiments, the pharmaceutical compositions described herein provide a pharmacological profile of the active drug substance, wherein the 2$^{nd}$ point where a concentration of 50% of steady state $C_{max}$ is reached is selected from no earlier than 4 hours, no earlier than 6 hours, no earlier than 8 hours, no earlier than 10 hours, no earlier than 12 hours, no earlier than 14 hours, and no earlier than 15 hours after last administration of the pharmaceutical composition to a steady state individual. For example, the 2$^{nd}$ point where a concentration of 50% of steady state $C_{max}$ is reached may be in a range selected from 4 to 48 hours, 6 to 48 hours, 8 to 48 hours, 10 to 48 hours, 12 to 48 hours, 14 to 48 hours, 4 to 34 hours, 6 to 34 hours, and 8 to 34 hours after last administration of the pharmaceutical composition to a steady state individual. In some embodiments, the 2$^{nd}$ point where the plasma concentration reaches 50% of steady state $C_{max}$ is not reached within the interval between administrations, and where such compositions are administrated continually, the 2$^{nd}$ point where the plasma concentration reaches 50% of steady state $C_{max}$ is not reached. In particular embodiments, time to 50% of $C_{max}$ is determined based on measurements in least 5 different individuals, such as human beings.

For continuous administration of an active drug substance over an interval of about 20 to 28 hours, such as a 24 hour interval, between administrations, pharmaceutical compositions as described herein comprising an active drug substance (for example, an analgesic, such as an opioid, including, for example morphine, oxycodone or hydrocodone), may be formulated such that, after administration to an individual, the 1$^{st}$ point where the plasma concentration reaches 50% of steady state $C_{max}$ is not reached too fast. Pharmaceutical compositions described herein, in particular such compositions which have a length selected from a range of 7.5 to 15 mm and a range of 8 to 10 mm are suited to achieving such a pharmacological profile. In certain such embodiments, the 1$^{st}$ point where a concentration of 50% of steady state $C_{max}$ is reached is selected from no earlier than 30 min. and no earlier than 45 min. In some such embodiments, the 1$^{st}$ point where a concentration of 50% of steady state $C_{max}$ is reached occurs in a range selected from 45 to 150 min, 45 to 120 min, and 45 to 90 min. after last administration of the pharmaceutical composition to a steady state individual. For example, in certain such embodiments, the 1$^{st}$ point where a concentration of 50% of steady state $C_{max}$ is reached occurs in a range selected from 0.25 to 2 hours and 0.5 to 2 hours after last administration of the pharmaceutical composition to a steady state individual. In particular embodiments, the time to 50% of $C_{max}$ is determined based on measurements in least 5 different individuals, such as human beings.

In specific embodiments, pharmaceutical compositions as described herein are formulated to provide a $T_{max}$ of an active drug substance (for example, an analgesic, such as an opioid, including, for example, morphine, oxycodone or hydrocodone) selected from a range of 3 to 10 hours, 4 to 7 hours, and 4 to 6 hours after last administration to a steady state individual. In specific embodiments, $T_{max}$ is based on an average of measurements in at least 5 different individuals, preferably 5 human beings.

In some embodiments, the pharmaceutical compositions described herein include 30 mg of an active drug substance (such as an analgesic, for example, an opioid such as morphine) and exhibit a length of in a range selected from 7.5 to 15 mm and 8 to 10 mm, and the pharmaceutical composition is formulated to provide a steady state $AUC_{0-24h}$ of the active drug substance selected from at least 200 nmol*h/L, at least 300 nmol*h/L, and at least 350 nmol*h/L. In certain such embodiments, the steady state $AUC_{0-24h}$ of the active drug substance is selected from a range of 200 to 1000 nmol*h/L, a range of 300 to 1000 nmol*h/L, a range of 300 to 500 nmol*h/L, and a range of 300 to 400 nmol*h/L.

In some embodiments, the pharmaceutical compositions described herein include 100 mg of an active drug substance (such as an analgesic, for example, an opioid such as morphine) and exhibit a length of in a range selected from 7.5 to 15 mm and 8 to 10 mm, and the pharmaceutical composition is formulated to provide a steady state $AUC_{0-24h}$ of the active drug substance selected from at least 400 nmol*h/L, at least 600 nmol*h/L, at least 800 nmol*h/L, at least 1000 nmol*h/L, at least 1200 nmol*h/L and at least 1400 nmol*h/L. In certain such embodiments, the steady state $AUC_{0-24h}$ of the active drug substance is selected from a range of 1000 to 3000 nmol*h/L, a range of 1000 to 2000 nmol*h/L, a range of 1200 to 2000 nmol*h/L, a range of 1200 to 1600 nmol*h/L, and a range of 1400 to 1600 nmol*h/L.

In some embodiments, the pharmaceutical compositions described herein include 20 mg of an active drug substance (such as an analgesic, for example, an opioid such as hydrocodone) and exhibit a length of in a range selected from 7.5 to 15 mm and 8 to 10 mm, and the pharmaceutical composition is formulated to provide an $AUC_{0-42h}$ of the active drug substance selected from at least 800,000 pmol*h/L, at least 900,000 pmol*h/L, and at least 940,000 pmol*h/L. In certain such embodiments, the $AUC_{0-42h}$ of the active drug substance is selected from a range of 800,000 to 1,200,000 pmol*h/L, a range of 900,000 to 1,200,000 pmol*h/L, and a range of 940,000 to 1,100,000 pmol*h/L.

In some embodiments, the pharmaceutical compositions described herein include 40 mg of an active drug substance (such as an analgesic, for example, an opioid such as oxycodone) and exhibit a length of in a range selected from 7.5 to 15 mm and 8 to 10 mm, and the pharmaceutical composition is formulated to provide an $AUC_{0-48h}$ of the active drug substance selected from at least 400 nmol*h/L, at least 450 nmol*h/L, and at least 500 nmol*h/L. In certain such embodiments, the $AUC_{0-48h}$ of the active drug substance is selected from a range of 400 to 1,000 nmol*h/L, a range of 450 to 1000 nmol*h/L, a range of 500 to 1000 nmol*h/L, and a range of 500 to 600 nmol*h/L.

Preferably, $AUC_{0-24h}$ and $AUC_{0-48h}$ are determined as an average based on measurements in at least 5 different individuals, for example 5 human beings.

In particular embodiments, the MRT (mean residence time) of the pharmaceutical compositions described herein is sufficiently long. Thus, in certain embodiments, the pharmaceutical compositions described herein are formulated for delivery of an active drug substance (such as an analgesic, including, for example, an opioid such as morphine, oxycodone or hydrocodone) over an interval of about 20 to 28 hours, such as a 24 hour interval, and to provide an MRT selected from at least 11 hours, at least 12 hours, at least 13 hours, at least 14 hours, and at least 15 hours. In particular such embodiments, the MRT are selected from a range of 11 to 30 hours, 12 to 30 hours, 13 to 30 hours, 14 to 30 hours, and 15 to 30 hours.

The controlled release formulations of active drug substances described herein can be formulated to release the active drug substance in a manner that the desired clinical efficacy is achieved. For example, where the active drug substance is an analgesic for the treatment of pain, the pharmaceutical compositions described herein can be formulated to provide continued release of the active drug substance in a manner that pain is relieved or ameliorated in the individual to whom the pharmaceutical composition is administered continuously throughout the treatment period.

For pharmaceutical compositions prepared for continued administration of an active drug substance over an interval of about 5 to 20 hours, such as a 12 hour interval or an interval in a range selected from a of about 7 to 20 hours, a range of about 6 to 18 hours, a range of about 10 to 20 hours, a range of about 10 to 18 hours, and a range of about 10 to 16 hours, the pharmacokinetic profile may be different from those provided by pharmaceutical compositions formulated for longer dosing intervals.

Thus, for such formulations, upon administration the average steady state trough (such as the theoretical steady state trough) of the active drug substance may be in a range selected from a range of 5 to 40%, a range of 5 to 30%, a range of 10 to 30%, a range of 10 to 20%, a range of 14 to 27%, and a range of 8 to 20% of average steady state $C_{max}$ of the active drug substance. In certain such embodiments, the pharmaceutical compositions may be formulated with a length selected from a range of 4 to 8 mm, a range of 5.5 to 8 mm, and a range of 6 to 7.5 mm, with said compositions comprising an active drug substance (for example, an analgesic, such as an opioid, including, for example, morphine, oxycodone or hydrocodone) as described herein.

In specific embodiments, of pharmaceutical compositions formulated for continued administration of an active drug substance over an interval of about 7 to 20 hours, such as a 12 interval, between individual administrations, the pharmaceutical compositions may be formulated to provide a MRT in a range selected from a range of 8 to 15 hours, a range of 10 to 15 hours, and a range of 11 to 14.5 hours. In certain such embodiments, the pharmaceutical compositions may be formulated with a length selected from a range of 4 to 8 mm, a range of 5.5 to 8 mm, and a range of 6 to 7.5 mm, with said compositions comprising an active drug substance (for example, an analgesic, such as an opioid, including, for example morphine, oxycodone or hydrocodone) as described herein.

In specific embodiments of pharmaceutical compositions formulated for delivery of an active drug substance over an interval of about 7 to 20 hours, such as a 12 hour interval, between administrations, the pharmaceutical compositions may comprise an active drug substance (for example, an analgesic, such as an opioid, including, for example morphine, oxycodone or hydrocodone) as described herein, and be formulated such that, after administration to an individual in need thereof, the active drug substance is delivered from the pharmaceutical composition such that the $2^{nd}$ point where the plasma concentration reaches 50% of steady state $C_{max}$ occurs in the range of 4 to 6 hours. In certain such embodiments, the pharmaceutical composition is formulated such the length of the pharmaceutical compositions are selected from a range 4 to 8 mm, a range of 5.5 to 8 mm, and a range of 6 to 7.5 mm.

In particular embodiments of the pharmaceutical compositions described herein, the Protraction index lies as closely to 1 as possible. In such embodiments, the plasma concentration is substantially constant throughout the 24 hour dosing interval, i.e., throughout the period between two consecutive administrations. Hence, in specific embodiments of the pharmaceutical compositions described herein, the pharmaceutical compositions are formulated to provide a Protraction index selected from at least 0.2, at least 0.25, at least 0.30, at least 0.35, at least 0.40, at least 0.45, at least 0.50, at least 0.55, at least 0.60, at least 0.70, and at least 0.80.

Drug Abuse

Pharmaceutical compositions as described herein can be formulated to provide a reduced risk for drug abuse and/or alcohol induced dose dumping.

In particular embodiments, the pharmaceutical compositions described herein may be formulated to mitigate or prevent alcohol induced dose dumping. In certain such embodiments, the pharmaceutical compositions are formulated such that the ratio (R50) between $t_{50\%}$ w/w (40% w/w ethanol in medium 1) and $t_{50\%}$ w/w (medium 1) is 1 or more. $t_{50\%}$ w/w (medium 1) denotes the time it takes to release 50% w/w of the active drug substance from the pharmaceutical composition in an in vitro dissolution test according to USP 30, NF 25, (711), Apparatus 2, paddle employing water optionally buffered to a specific pH as dissolution medium (medium 1), and $t_{50\%}$ w/w (40% w/w ethanol in medium 1) denotes the time it takes to release 50% w/w of the active drug substance from the pharmaceutical composition in an in vitro dissolution test according to USP 30, NF 25, (711), Apparatus 2, paddle employing 40% w/w ethanol in medium 1 as dissolution medium.

In a specific embodiment, the ratio R50 is at the most 5, such as at the most 4, at the most 3, or at the most 2. Notably, in specific such embodiments, the ratio R50 provided by the pharmaceutical compositions described herein is from 1 to 1.5 such as, for example, from 1 to 1.4, from 1 to 1.3, from 1 to 1.2, from 1 to 1.1, from 1 to 1.05, about 1, from 1 to 0.95 or from 1 to 0.9.

The same may also apply for ratios determined, for example, when 25%, 30%, 40%, 60%, 70%, 80%, 90% and/or 95% w/w has been released, the conditions being as described above.

The likelihood of a composition being subject to drug abuse may for example be tested by different tests:
1. Crushing test
2. Melting test
3. Extraction/dissolving test
4. Injection test In the crushing test, the composition is subjected to crushing using a hammer or an apparatus designed to measure the hardness of an oral dosage form. A suitable apparatus is specified in Ph. Eur. If the composition disintegrates into particles, then it may be possible to dissolve or suspend these particles and use them for abuse purposes. Moreover, if it is possible to disintegrate (crush) the composition, then it is possible to use the powder for snorting or sniffing and in this way abuse the composition. However, if it is not possible to crush the composition in this test, then there will be no particles to use for such abuse purposes. In particular embodiments, the pharmaceutical compositions described herein cannot be crushed into particles by the apparatus specified in Ph. Eur.

In the melting test, the composition is subjected to heating, for example, on a spoon or by exposure to microwave induced heating. If the composition is suitable for susceptible to abuse, when subject to such a test, the composition will become so liquid that it is possible to inject it, without being too hot. However, a composition that is not susceptible to abuse, when subject to a standard melting test, will not become a liquid suitable for injection. Accordingly, in specific embodiments, compositions as described herein may be formulated such that they do not become so liquid that it is possible to inject them upon subjecting the compositions heating in a standard melt test.

In the extraction test, the ease with which it is possible to extract the active drug substance from the composition by means of normally available organic solvents is evaluated. If it is possible to dissolve the composition or extract the active drug substance from the composition using such organic solvents, then such a composition is susceptible to abuse. Conversely, if it is not possible to dissolve or extract significant quantities of the active drug substance from the composition using such solvents, then the composition may not be susceptible to misuse. Thus, in particular embodiments, the pharmaceutical compositions described herein may be formulated such that it is not possible to dissolve the pharmaceutical compositions or extract significant amounts of active drug substance faster than in a dissolution medium which may be either ethanol or phosphate buffer pH 6.8

In the Injection test, the composition is dissolved in 2 ml water possibly after extensive heating. The preparation is put into a syringe and the time of passage through a fitted 0.5 mm needle is measured upon a weight applied to the syringe of 3 kg. In specific embodiments, the pharmaceutical compositions described herein are formulated such that the time of passage of the pharmaceutical compositions subjected to the Injection Test is at least 10 sec., such as at least 15 sec., or at least 20 sec.

Pharmaceutical compositions described herein are formulated to resist abuse by crushing, melting, extraction, dissolution, or similar techniques. Furthermore, the pharmaceutical compositions described herein can be formulated to exhibit decreased (or essentially the same) release rate in alcohol containing media as compared to a purely aqueous media. The release rate from the pharmaceutical composition will depend on several parameters, including, but not limited to: solubility of the polyglycol, active drug substance and any excipients included in the composition; the wettability of the composition; the diffusion of water into the composition; the enthalpy of melting and enthalpy of solubilization; and the disentanglement rate of the polyglycol during dissolution. Controlled release dosage forms are used to extend the release from the dosage form for an extended period of time. In the present context the term "controlled release" is used to designate a release a desired rate during a predetermined release period.

All patent and non-patent references cited in the application are hereby incorporated by reference in their entirety.

EXAMPLES

The invention is further illustrated in the following non-limiting examples.

Example 1

A Single-Center, Single Dose, Randomised, Open Label; Exploratory, 5-Way Cross-Over Study Evaluating the Pharmacokinetic Profile of Various Egalet® Hydrocodone Test Formulations in Healthy Volunteers Under Fasting Conditions This study is also referred to as HC-EG-001 herein.
Design The study was a single centre, open-label, single-dose, randomised, 4-way crossover, comparative Phase I study, in which the pharmacokinetic profile of four different Egalet® hydrocodone test-formulations was evaluated and compared to a marketed, reference listed drug (NORCO® 10/325). Two (2) different chemical formulations (with medium and a high drug load respectively) and three (3) different geometries (6.0 mm, 7.5 mm, and 9.0 mm) were developed. For the medium load formulation, all three geometries were available, whereas only the 9 mm was available in the high load formulation.

Hydromorphone contributes to the total analgesic effect and norhydrocodone is an abundant metabolite. Therefore, for the purposes of this study, hydrocodone, hydromorphone and norhydrocodone were measured in plasma samples.

Investigational Products

Treatment A: 1×20 mg Egalet® hydrocodone PR tablet of Formulation A, 6.0 mm.

Treatment B: 1×20 mg Egalet® hydrocodone PR tablet of Formulation A, 7.5 mm.

Treatment C: 1×20 mg Egalet® hydrocodone PR tablet of Formulation A, 9.0 mm.

Treatment D: 1×20 mg Egalet® hydrocodone PR tablet of Formulation B, 9.0 mm.

Treatment E (Reference): 1×NORCO® 10/325 IR tablet (containing 10 mg hydrocodone bitartrate and 325 mg acetaminophen).

Treatments A through D are pharmaceutical compositions prepared according to the present description. The compositions of the products are shown herein below in Example 3, Tables 16 and 17.

Methodology

The 28 healthy, adult subjects enrolled in this study were members of the community at large. Subjects were judged eligible for participation in the study when assessed against the inclusion and exclusion criteria.

In each period, drug administration was performed on the morning of Day 1, after subjects had undergone a supervised overnight fast of at least 10 hours. Subjects, seated in upright position, were administered a single oral dose of either Egalet® hydrocodone 20 mg test formulations or NORCO® 10/325 with approximately 240 mL of water.

Subjects were dosed as specified in the protocol, and subsequently fasted for a period of at least 4 hours. Subjects were instructed to swallow the study medication whole. There were washout periods of 6-7 days or more between doses.

Sample Collection

In each period, all blood samples were drawn into blood collection tubes (1×4 mL) containing EDTA $K_2$; prior to drug administration and 0.333, 0.667, 1.00, 1.33, 1.67, 2.00, 2.50, 3.00, 3.50, 4.00, 4.50, 5.00, 6.00, 7.00, 8.00, 10.0, 12.0, 15.0, 18.0, 21.0, 24.0, 27.0, 30.0, 36.0, and 42.0 hours post-dose. When deemed appropriate by the clinical staff, and as agreed upon by the subject, a dead-volume intravenous catheter was used for blood collection to avoid multiple skin punctures. Otherwise, blood samples were collected by direct venipuncture.

Safety

The safety assessments were including vital signs, ECGs, biochemistry, hematology, urine analysis, urine drug screen, pregnancy tests and adverse experience recording. They were conducted according to standard medical practices and are generally accepted as reliable, accurate, and relevant. The study data were analysed using standard methods widely accepted by medical and regulatory agencies.

Pharmacokinetic Parameters

The following pharmacokinetic parameters were calculated by standard non-compartmental methods for hydrocodone plasma concentrations:

1) AUC(0-t): area under the concentration-time curve from time zero to the last non-zero concentration: The area under the concentration-time-curve from time 0 h until the last concentration sample at time 42 h, $AUC_{0-t}$, were calculated by the linear trapezoidal method, using the actual sampling time points. If the last blood sample was taken less than 42 hours after drug administration, the 42 h values were extrapolated using the terminal elimination rate constant, Kel as described below. If the last sample was taken after 42 hours, a 42 h value was estimated by interpolation. Intermediate missing values remained missing (equivalent to interpolating between neighbouring points when calculating AUC). Intermediate values below the limit of quantification (LOQ) were assigned a value of LOQ/2, while trailing values below LOQ were assigned a value of zero.

2) $AUC_{(0-inf)}$: area under the concentration-time curve from time zero to infinity (extrapolated): was determined for profiles that did not return to zero within 42 hours. $AUC_{0-inf}$ was calculated as the sum of $AUC_{0-t}$ and Ct Primary bioequivalence analysis of hydrocodone where Ct was the last sample above LOQ.

3) $C_{max}$: maximum observed concentration: were derived from the samples 0-42 h after drug administration. Actual sampling time points were used for $T_{max}$.

4) Residual area: calculated as $100*(1-AUC_{(0-t)}/AUC_{(0-inf)})$.

5) $T_{max}$: time of observed $C_{max}$: were derived from the samples 0-42 h after drug administration. Actual sampling time points were used for $T_{max}$.

6) $T_{1/2}$ el: elimination half-life was found by $Ln(2)/K_{el}$.

7) $K_{el}$: elimination rate constant: was the slope of the terminal part of the log-concentration-time-curve and was found using log-linear regression. The final three plasma concentrations above LOQ were included in the calculation as a minimum. However, the log-linear plots of plasma concentration were inspected and a different selection of data points could have been chosen to ensure that the time period represented the terminal elimination phase. Actual time values were used.

8) MRT: Mean residence time; was calculated as $MRT_{0-inf} = AUMC_{0-inf}/AUC_{0-inf}$, where $AUMC_{0-inf} = AUMC_{0-t} + t*Ct/K_{el} + Ct/(K_{el})2$, and where $AUMC_{0-t}$ was the area under the first moment curve from time 0 until the last valid measurement at the time point t. Ct was the last valid plasma concentration found at this time point, t.

9) $AUC_{0-12}$ and $AUC_{0-24}$: were calculated by utilisation of the linear trapezoidal method in the same way as for $AUC_{0-t}$.

11) Proportion $AUC_{(0-Tmax)}$: was calculated as

Proportion $AUC_{(0-Tmax)} = 100*AUC_{0-Tmax}/AUC_{0-inf}$

12) Protraction index $(AUC_{0-24h}/24 h)/C_{max}$ was calculated for each individual with regard to the hydrocodone concentration profile Pharmacokinetic Methods Numerical data was presented in summary tables by number of subjects, arithmetic mean (geometric mean and CV where applicable), median, standard deviation, minimum and maximum. Categorical data is presented by number and percent of subjects as well as number events (where applicable).

All calculations of endpoints, analyses and presentation of endpoints were carried out in SAS version 9.1 (Statistical Analysis System) or later versions. Analysis datasets were derived from the study data and was adhere to the CDISC ADaM standard (Clinical Data Interchange Standard Consortium Analysis Data Model).

For the hydrocodone $AUC_{0-42}$, $AUC_{0-inf}$ and $C_{max}$ primary PK parameters, the ratio between test treatments A, B, C and D compared to treatment E (reference) were, after log transformation, estimated in a mixed linear model as Log (Endpoint)=Treatment+Period+Subject+random error, Where treatment (A, B, C, D or E) and period were fixed effects and subject was a random effect.

The estimation included all valid PK data from all treatments for each comparison. Treatment sequence was included as a fixed effect in the above model.

The ratios of means (NE, B/E, C/E and D/E) were calculated with 90% geometric confidence intervals based on least squares means. The treatment difference and corresponding confidence interval were back-transformed, thus yielding ratio estimates. Hence, the CI was evaluated against the range (0.80; 1.25).

Other endpoints were tabulated.

Pharmacokinetic Results

A total of 28 subjects were enrolled in the study. Twenty-eight (28) subjects received at least one dose of the study medication and comprised the safety population. The pharmacokinetic analyses included 22 subjects who completed at least 2 periods, 21 subjects who completed at least 4 periods, and 19 subjects who completed the study.

The mean dose-normalized $AUC_{0-t}$ and $AUC_{0-inf}$ values for all Egalet® test PR formulations were similar to those obtained for the reference IR formulation (NORCO® 10/325) as evidenced by the ratios and 90% confidence intervals contained within the interval limits of 80%-125%. As expected, the mean $C_{max}$ values for all test PR formulations were lower than those observed for the reference IR formulation (NORCO® 10/325). The ratios of the least-squares means (Test/Reference) were 48%, 40%, 30% and 28% for formulations A1, A2, A3 and B1, respectively.

TABLE 1

Hydrocodone pharmacokinetic parameters (dose-normalised to 10 mg) for each treatment (N = 22)

| Treatment | $AUC_{0-42}$ (pmol · h/mL) | $AUC_{0-inf}$ (pmol · h/mL) | $C_{max}$ (pmol/mL) |
|---|---|---|---|
| Formulation A; 6 mm (A) | 526858.92 | 533766.04 | 38434.97 |
| Formulation A; 7.5 mm (B) | 541913.82 | 554169.22 | 31949.23 |
| Formulation A; 9 mm (C) | 479527.18 | 499662.11 | 24018.17 |

TABLE 1-continued

Hydrocodone pharmacokinetic parameters (dose-normalised to 10 mg) for each treatment (N = 22)

| Treatment | $AUC_{0-42}$ (pmol · h/mL) | $AUC_{0-inf}$ (pmol · h/mL) | $C_{max}$ (pmol/mL) |
|---|---|---|---|
| Formulation B; 9 mm (D) | 506327.16 | 528655.35 | 23021.18 |
| NORCO ® 10/325 (E) | 534903:70 | 541562.13 | 81660.68 |

TABLE 2

Hydromorphone pharmacokinetic parameters (dose-normalised to 10 mg) for each treatment (N = 22)

| Treatment | $AUC_{0-42}$ (pmol · h/mL) | $AUC_{0-inf}^*$ (pmol · h/mL) | $C_{max}$ (pmol/mL) |
|---|---|---|---|
| Formulation A; 6 mm (A) | 9070.15 | 9994.89 | 465.64 |
| Formulation A; 7.5 mm (B) | 8318.16 | 9255.32 | 369.78 |
| Formulation A; 9 mm (C) | 8405.98 | 9639.06 | 313.23 |
| Formulation B; 9 mm (D) | 8534.74 | 10443.43 | 306.84 |
| NORCO ® 10/325 (E) | 8590.99 | 9550.34 | 989.60 |

*For this parameter, N = 20 for Treatments C and D.

TABLE 3

Norhydrocodone pharmacokinetic parameters (dose-normalised to 10 mg) for each treatment (N = 22)

| Treatment | $AUC_{0-42}$ (pmol · h/mL) | $AUC_{0-inf}$ (pmol · h/mL) | $C_{max}$ (pmol/mL) |
|---|---|---|---|
| Formulation A; 6 mm (A) | 182950.37 | 188351.73 | 10492.78 |
| Formulation A; 7.5 mm (B) | 178872.71 | 188108.45 | 8431.64 |
| Formulation A; 9 mm (C) | 159263.00 | 173834.25 | 6938.85 |
| Formulation B; 9 mm (D) | 157005.92 | 173530.75 | 5988.92 |
| NORCO ® 10/325 (E) | 191267.71 | 196338.68 | 17984.46 |

TABLE 4

Summary of hydrocodone pharmacokinetic parameters for each treatment (N = 22)

| Parameters | | Formulation A 6 mm (A) (N = 20) Mean (min-max) | Formulation A 7.5 mm (B) (N = 20) Mean (min-max) | Formulation A 9 mm (C) (N = 20) Mean (min-max) | Formulation B 9 mm (D) (N = 20) Mean (min-max) | NORCO ® 10/325 (E) (N = 21) Mean |
|---|---|---|---|---|---|---|
| $AUC_{0-t}$ | (pmol · h/mL) | 1053717.85 (566723-1501558) | 1083827.64 (573855-1601524) | 959054.36 (513753-1412443) | 1012654.33 (511294-1488550) | 534903.70 (263032-854269) |
| $AUC_{inf}$ | (pmol · h/mL) | 1067532.07 (570971-1525746) | 1108338.44 (579026-1640043) | 999324.21 (518525-1455476) | 1057310.70 (518118-1587096) | 541562.13 (268171-867127) |
| Residual area | (%) | 1.25 (0.64-2.48) | 2.10 (0.81-4.38) | 3.73 (0.76-11.89) | 4.13 (1.32-9.53) | 1.23 (0.59-2.62) |
| $C_{max}$ | (pmol/mL) | 76869.94 (52083-105730) | 63898.46 (44804-93280) | 48036.34 (31808-88033) | 46042.36 (28407-69417) | 81660.68 (44714-130655) |
| $T_{max}$ | (h) | 6.25 (4.5-10.0) | 5.38 (2.5-15) | 5.25 (3.5-10.0) | 4.52 (3.00-7.00) | 1.08 (0.67-2.00) |
| $T_{max}^*$ | (h) | 4.75 | 4.50 | 4.75 | 4.50 | 1.00 |
| $K_{el}$ | ($h^{-1}$) | 0.1204 (0.0839-0.1611) | 0.1178 (0.0870-0.1684) | 0.1196 (0.0568-0.1794) | 0.1174 (0.0733-0.1737) | 0.1176 (0.0695-0.1569) |
| $T_{1/2\ el}$ | (h) | 5.91 (4.30-8.26) | 6.07 (4.11-7.97) | 6.11 (3.86-12.20) | 6.11 (3.99-9.46) | 6.16 (4.42-9.97) |
| MRT | (h) | 11.73 (9.49-13.99) | 14.23 (10.63-16.75) | 17.09 (10.18-21.61) | 18.12 (15.72-20.89) | 7.69 (5.73-10.56) |

*Median.

The protraction index was determined, and the data below in Table 5 are derived from the hydrocodone concentration profile obtained in the individuals that participated in this study.

TABLE 5

Protraction index

| Formulation A (6 mm) | Formulation A (7.5 mm) | Formulation A (9 mm) | Formulation B (9 mm) | Norco |
|---|---|---|---|---|
| \multicolumn{5}{c}{$(AUC_{0-24\,h}/24\,h)/C_{max}$} |||||
| 0.43 | 0.65 | 0.70 | 0.63 | 0.31 |
| 0.56 | 0.63 | 0.67 | 0.64 | 0.30 |
| 0.51 | 0.53 | 0.63 | 0.72 | 0.24 |
| 0.52 | 0.58 | 0.60 | 0.69 | 0.26 |
| 0.58 | 0.47 | 0.64 | 0.67 | 0.24 |
| 0.39 | 0.54 | 0.49 | 0.58 | 0.25 |
| 0.42 | 0.46 | 0.56 | 0.61 | 0.24 |
| 0.43 | 0.72 | 0.48 | 0.55 | 0.25 |
| 0.66 | 0.51 | 0.80 | 0.68 | 0.24 |
| 0.51 | 0.62 | 0.66 | 0.73 | 0.41 |
| 0.48 | 0.56 | 0.74 | 0.61 | 0.20 |
| 0.49 | 0.74 | 0.76 | 0.69 | 0.18 |
| 0.63 | 0.67 | 0.72 | 0.79 | 0.37 |
| 0.67 | 0.63 | 0.38 | 0.57 | 0.32 |
| 0.59 | 0.63 | 0.67 | 0.79 | 0.27 |
| 0.49 | 0.53 | 0.74 | 0.72 | 0.29 |
| 0.47 | 0.68 | 0.61 | 0.62 | 0.25 |
| 0.50 | 0.60 | 0.62 | 0.51 | 0.31 |
| 0.52 | 0.67 | 0.63 | 0.65 | 0.26 |
| — | 0.73 | 0.68 | 0.79 | 0.22 |
| — | — | 0.56 | 0.61 | 0.23 |
| — | — | 0.70 | 0.81 | — |
| \multicolumn{5}{c}{Mean} |||||
| 0.52 | 0.61 | 0.64 | 0.67 | 0.27 |
| \multicolumn{5}{c}{Min} |||||
| 0.39 | 0.46 | 0.38 | 0.51 | 0.18 |
| \multicolumn{5}{c}{Max} |||||
| 0.67 | 0.74 | 0.80 | 0.81 | 0.41 |

Figure 2:
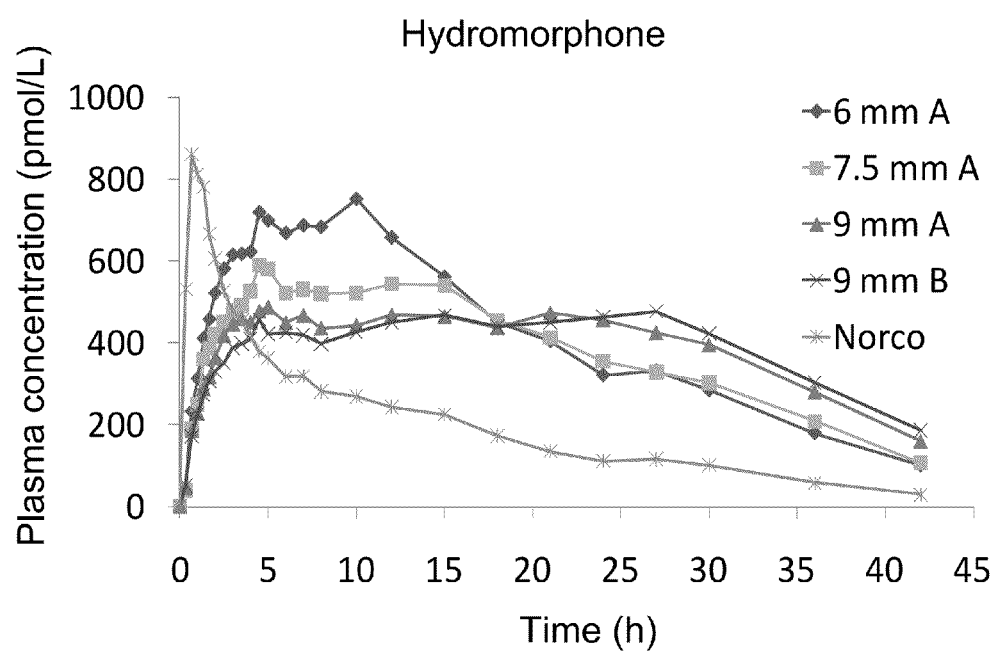
FIG. 2 shows the mean hydromorphone plasma concentration (pmol/L) versus time (h) curve after single dose administration by dose group (0-42 h). Formulation A (6 mm) is treatment A, formulation A (7.5 mm) is treatment B, formulation A (9 mm) is treatment C, formulation B (9 mm) is treatment D and Norco® is treatment E.
Figure 3:
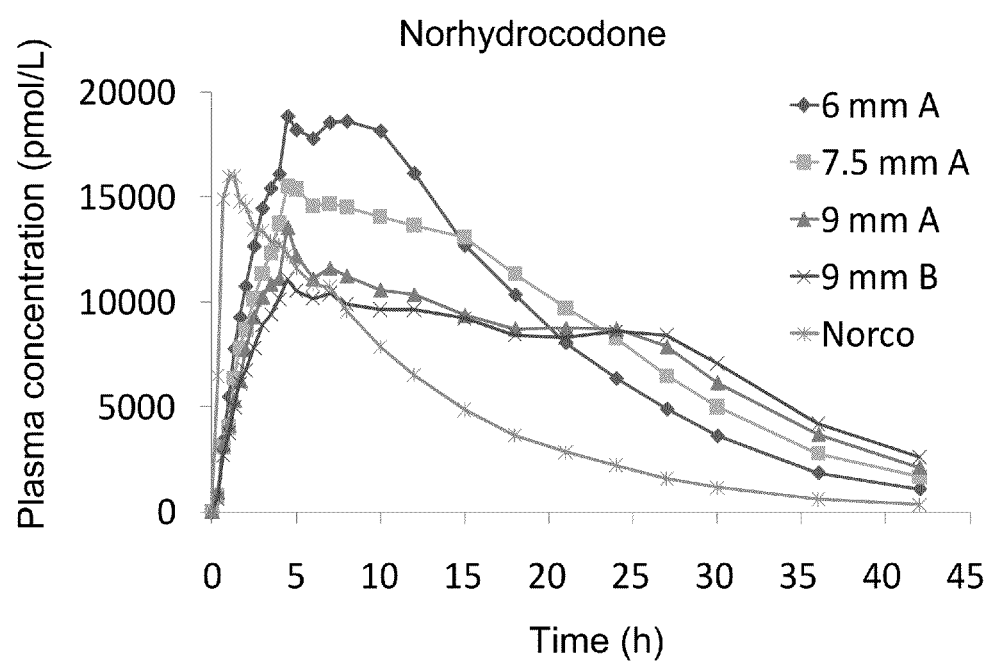
FIG. 3 shows the mean norhydrocodone plasma concentration (pmol/L) versus time (h) curve after single dose administration by dose group (0-42 h). Formulation A (6 mm) is treatment A, formulation A (7.5 mm) is treatment B, formulation A (9 mm) is treatment C, formulation B (9 mm) is treatment D and Norco® is treatment E.

FIGS. 1 to 3 show the mean plasma concentration versus time profiles for hydrocodone, hydromorphone and norhydrocodone after single dose administration by dose group (0-42 h).

Safety Results

No severe, significant, or serious adverse events were reported during the study. The frequency of adverse event observations did not appear to be related to treatment. Overall, adverse events were mild or moderate in intensity and were, except for a few, expected opioid effects. No safety concerns with respect to the clinical laboratory tests, vital signs, and ECGs were raised.

Discussion

The median $T_{max}$ for the four Egalet® formulations was almost identical and between 4.50 hours (treatment A & C) and 4.75 (treatment B & D), whereas the median $T_{max}$ for Norco 10/325 was 1.00 hour.

NORCO® 10/325, when dosed in half nominal dosage of the Egalet® formulations gave rise to a $C_{max}$ of 81661 pmol/mL, slightly higher than the $C_{max}$ (76870 pmol/mL) obtained for treatment A, the Egalet® formulation resulting in the highest $C_{max}$. When dose-normalized and tested for equivalence, the ratios of least-square means were below 50% for all Egalet® formulations, which indicates the prolonged and slower release from the Egalet® formulations.

Both treatment A and treatment B might be relevant candidates to consider for a twice daily dosage regimen. For treatment C and D, which both have the same geometry, but different chemical compositions, the mean concentration-time-curves display an almost identically pattern. These two formulations have prolonged in-vivo profiles, with fairly constant hydrocodone concentrations until the 24 hours post-dose time-point, after which elimination occurs. Both release profiles provide once-daily dosing characteristics. Further, treatment D, for example, illustrates the viability of developing relatively higher dose-strength compositions, which can be relevant for opioid tolerant patients.

When dose-normalized, all Egalet® formulations were found to provide the same total hydrocodone exposure as Norco 10/325. CI's for point-estimates for Egalet® treatments A and B did include 100%; CI's for treatment A ranging from approximately 95%-103% and for Treatment B ranging between 97-107%. Point-estimates for treatment C and D were below 100%, lowest for formulation C, but point estimates and corresponding 90% confidence limits were all within 80-125% acceptance limits, and thus considered equivalent. AUC equivalence was also found for metabolites.

Steady State Pharmacokinetics Simulation

The individual patient data from study HC-EG-001 were simulated to Steady state to derive the steady state parameters of the Egalet® formulations tested and to assess the individual ranges for $C_{24}/C_{max}$ supporting the use of Egalet® Hydrocodone for administration with 24 hours interval.

Method for SS Simulation

The individual steady state data in the time interval [0 h, 24 h] were estimated as a sum of two components a) the sample values in the [0 h, 24 h] interval and b) estimated tail values in the interval [24 h, infinity], for example, the estimated value at 1 hour on day 2, 3, 4 etc. This corresponds to the superimposition principle. The tail was assumed to follow the standard one-compartment elimination (i.e. exponential function), and was estimated based on sample data from 24-42 hours for Hydrocodone and derivatives.

The estimated tails after 42 h were less than 20% of total area and were included in the modelling.

For Hydrocodone the reference dose was 10 mg while test-doses were 20 mg. No dose normalisation was performed.

Results

TABLE 6

Summary of Steady State Parameters

| Treatment | | Peak (pmol/mL) | Trough (pmol/mL) | Trough/Peak Ratio | $T_{max}$ (Hours) |
|---|---|---|---|---|---|
| A 6.0 mm | N | 20 | 20 | 20 | 20 |
| | Mean | 82873 | 12136 | 0.14 | 6.25 |
| | Median | 82296 | 11931 | 0.14 | 4.75 |
| | Range | 54340-111354 | 4620-25139 | 0.06-0.27 | 4.50-10.00 |

TABLE 6-continued

Summary of Steady State Parameters

| Treatment | | Peak (pmol/mL) | Trough (pmol/mL) | Trough/Peak Ratio | $T_{max}$ (Hours) |
|---|---|---|---|---|---|
| A 7.5 mm | N | 20 | 20 | 20 | 20 |
| | Mean | 75908 | 20241 | 0.26 | 5.38 |
| | Median | 74781 | 19423 | 0.27 | 4.50 |
| | Range | 51907-107306 | 5954-33512 | 0.11-0.37 | 2.50-15.00 |
| A 9.0 mm | N | 22 | 22 | 22 | 22 |
| | Mean | 67119 | 26909 | 0.40 | 5.25 |
| | Median | 65726 | 27115 | 0.42 | 4.75 |
| | Range | 43067-109224 | 4626-41216 | 0.08-0.52 | 3.50-10.00 |
| B 9.0 mm | N | 22 | 22 | 22 | 22 |
| | Mean | 68359 | 29121 | 0.42 | 4.52 |
| | Median | 66746 | 26434 | 0.42 | 4.50 |
| | Range | 38985-107507 | 12482-48370 | 0.30-0.56 | 3.00-7.00 |
| Reference | N | 20 | 20 | 20 | 20 |
| | Mean | 86525 | 3368 | 0.04 | 1.05 |
| | Median | 83719 | 2855 | 0.03 | 1.00 |
| | Range | 54982-137908 | 1324-7698 | 0.02-0.08 | 0.67-2.00 |

Figure 4:
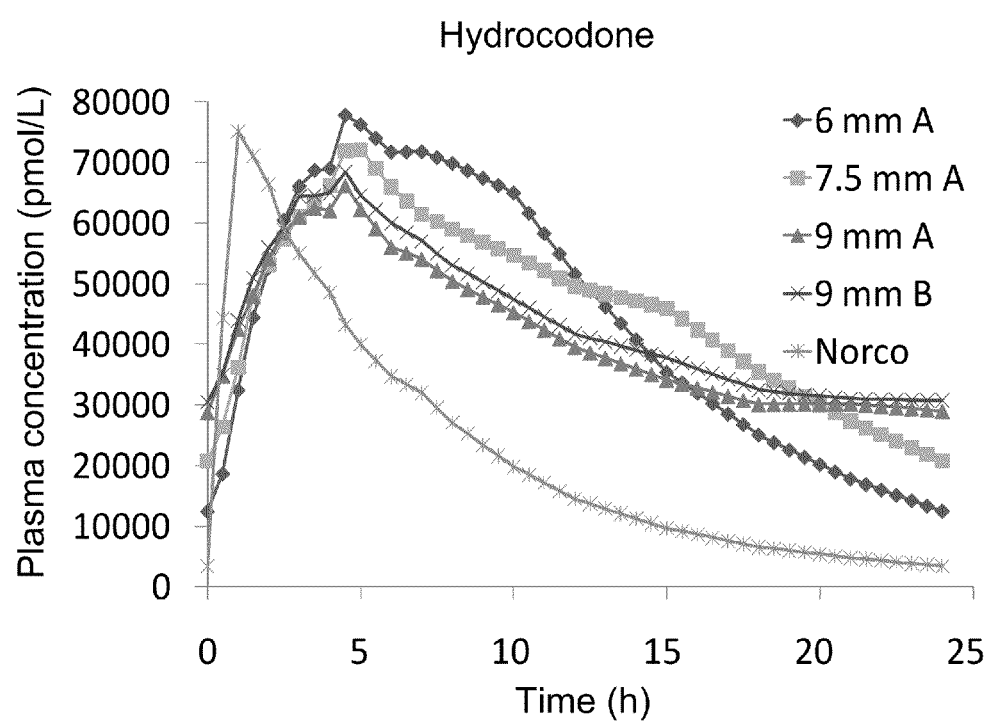
FIG. 4 shows an estimated steady state hydrocodone curve, plasma concentration (pmol/L) versus time (h). Formulation A (6 mm) is treatment A, formulation A (7.5 mm) is treatment B, formulation A (9 mm) is treatment C, formulation B (9 mm) is treatment D and Norco® is treatment E.

FIG. 4 shows an estimated steady state hydrocodone curve

The results of this study further illustrate that the formulation and configuration of pharmaceutical compositions according to the present description can be adjusted to achieve desired delivery characteristics and pharmacokinetic profiles. For example, in this study, a relatively short Egalet® formulation with a relatively wide release area (A1, 6 mm length) provides a relative fast release rate and a $C_{max}$ and AUC equivalent to the immediate release comparator product Norco®. The profile patterns are similar for the metabolites. A longer geometry with a smaller area exposed for release at the open ends of the Egalet® formulation provides a lower $C_{max}$ and release over a longer period providing a more sustained plasma profile.

Example 2

A Randomized, Comparative, Open-Label, Crossover, Phase I Study Evaluating Single Dose Pharmacokinetic Profiles of Various Egalet® Oxycodone 40 mg Test Formulations Versus OxyContin® in Healthy Volunteers Using Naltrexone Blockade Under Fasting Conditions The study is also referred to as OC-EG-001 herein.

Design

The study was a single centre, open-label, single-dose, randomised, 4-way crossover, comparative Phase I study, wherein the PK profiles of single doses of three different geometries (6.0 mm, 7.5 mm and 9.0 mm) of Egalet® oxycodone 40 mg tablets prepared according to the present description were evaluated and compared to a marketed, reference listed drug, OxyContin® 40 mg.

Primary pharmacokinetic analyses were performed with measurements of oxycodone plasma concentrations and secondary analysis of the plasma concentrations of the active metabolites noroxycodone and oxymorphone.

TABLE 7

Treatments

| Treatment regimens | Co-administration |
|---|---|
| Treatment A (test 1, 6.0 mm): 1 × 40 mg Egalet ® oxycodone | Naltrexone 1 × 50 mg 12 and 1 hour prior to dosing of treatment regimen A-D |

TABLE 7-continued

Treatments

| Treatment regimens | Co-administration |
|---|---|
| Treatment B (test 2, 7.5 mm): 1 × 40 mg Egalet ® oxycodone | Naltrexone 1 × 50 mg 12 and 1 hour prior to dosing of treatment regimen A-D |
| Treatment C (test 3, 9.0 mm): 1 × 40 mg Egalet ® oxycodone | Naltrexone 1 × 50 mg 12 and 1 hour prior to dosing of treatment regimen A-D |
| Treatment D (reference): 1 × 40 mg OxyContin ® (containing oxycodone) | Naltrexone 1 × 50 mg 12 and 1 hour prior to dosing of treatment regimen A-D |

The composition of the formulations is given in Example 3, Table 12 herein below.

Methodology

For each period, subjects were confined to the clinical research facility from at least 14 hours prior to drug administration and were discharged from the clinic at least 48 hours after study drug administration. The treatment phases were separated by washout periods of 7 days.

In each period, subjects were administered a single oral dose of one of the three Egalet® oxycodone 40 mg or OxyContin® (as one 40 mg controlled release tablet), in accordance with the subjects' randomization sequence under fasting conditions. 50 mg Naltrexone was co-administered (to alleviate or avoid opioid side effects) in opioid-naïve subjects, as presented in Table 7.

Sample Collection

In each period, all blood samples were drawn into blood collection tubes (1×4 mL) containing potassium EDTA K2; prior to drug administration and 0.333, 0.667, 1.00, 1.50, 2.00, 2.50, 3.00, 3.50, 4.00, 4.50, 5.00, 6.00, 7.00, 8.00, 10.0, 12.0, 16.0, 20.0, 24.0, 30.0, 36.0, and 48.0 hours post dose.

When deemed appropriate by the clinical staff, and as agreed upon by the subject, a dead-volume intravenous catheter was used for blood collection to avoid multiple skin punctures; collections were performed via direct venipuncture, otherwise.

Pharmacokinetic Parameters

The following PK parameters were calculated and summarised by standard non-compartmental methods for oxycodone plasma concentrations, noroxycodone and oxymorphone plasma concentrations respectively. The PK endpoints were calculated individually for each subject and treatment for the plasma concentrations obtained on Days 1-3 (0-48 h) within each period.

1) $AUC_{(0-t)}$: area under the concentration-time curve from time zero to the last non-zero concentration: The area under the concentration-time-curve from time 0 h until the last concentration sample at time 48 h, $AUC_{0-t}$, were calculated by the linear trapezoidal method, using the actual sampling time points. If the last blood sample was taken less than 48 hours after drug administration, the 48 h values were extrapolated using the terminal elimination rate constant, Kel as described below. If the last sample was taken after 48 hours, a 48 h value was estimated by interpolation. Intermediate missing values remained missing (equivalent to interpolating between neighbouring points when calculating AUC). Intermediate values below the limit of quantification (LOQ) were assigned a value of LOQ/2, while trailing values below LOQ were assigned a value of zero.
2) $AUC_{(0-inf)}$: area under the concentration-time curve from time zero to infinity (extrapolated): was determined for profiles that did not return to zero within 48 hours. $AUC_{(0-inf)}$, was calculated as the sum of $AUC_{0-t}$ and Ct Primary bioequivalence analysis of Oxycodone where Ct was the last sample above LOQ.
3) $C_{max}$: maximum observed concentration: were derived from the samples 0-48 h after drug administration. Actual sampling time points were used for $T_{max}$.
4) Residual area: calculated as $100*(1-AUC_{(0-t)}/AUC_{(0-inf)})$.
5) $T_{max}$: time of observed $C_{max}$: were derived from the samples 0-48 h after drug administration. Actual sampling time points were used for $T_{max}$.
6) $T_{1/2}$ el: elimination half-life was found by $Ln(2)/K_{el}$.
7) $K_{el}$: elimination rate constant: was the slope of the terminal part of the log-concentration-time-curve and was found using log-linear regression. The final three plasma concentrations above LOQ were included in the calculation as a minimum. However, the log-linear plots of plasma concentration were inspected and a different selection of data points could have been chosen to ensure that the time period represented the terminal elimination phase. Actual time values were used.
8) MRT: Mean residence time; was calculated as $$MRT_{0-inf} = AUMC_{0-inf}/AUC_{0-inf} \text{ where}$$

$$AUMC_{0-inf} = AUMC_{0-t} + t*Ct/K_{el} + Ct/(K_{el})2,$$

and where $AUMC_{0-t}$ was the area under the first moment curve from time 0 until the last valid measurement at the time point t. Ct was the last valid plasma concentration found at this time point, t.

9) $AUC_{0-12}$ and $AUC_{0-24}$: were calculated by utilisation of the linear trapezoidal method in the same way as for $AUC_{0-t}$.
11) Proportion $AUC_{(0-T\,max)}$: was calculated as Proportion $AUC_{(0-Tmax)} = 100*AUC_{0-Tmax}/AUC_{0-inf}$ 12) Protraction index $(AUC_{0-24h}/24\,h)/C_{max}$ was calculated for each individual with regard to the hydrocodone concentration profile Pharmacokinetic Methods Numerical data was presented in summary tables by number of subjects, arithmetic mean (geometric mean and CV where applicable), median, standard deviation, minimum and maximum. Categorical data is presented by number and percent of subjects as well as number events (where applicable).

All calculations of endpoints, analyses and presentation of endpoints were carried out in SAS version 9.1 (Statistical Analysis System) or later versions. Analysis datasets were derived from the study data and was adhere to the CDISC ADaM standard (Clinical Data Interchange Standard Consortium Analysis Data Model).

For the oxycodone $AUC_{0-48}$, $AUC_{0-inf}$ and $C_{max}$ primary PK parameters, the ratio between test treatments A, B, and C compared to treatment D (reference) were, after log transformation, estimated in a mixed linear model as Log (Endpoint)=Treatment+Period+Subject+random error, Where treatment (A, B, C, or D) and period were fixed effects and subject was a random effect.

The estimation included all valid PK data from all treatments for each comparison. Treatment sequence was included as a fixed effect in the above model.

The ratios of means (A/D, B/D, and C/D) were calculated with 90% geometric confidence intervals based on least squares means. The treatment difference and corresponding confidence interval were back-transformed, thus yielding ratio estimates. Hence, the CI was evaluated against the range (0.80; 1.25).

Other endpoints were tabulated.

Pharmacokinetic Results 28 subjects were screened for this study and upon completion of all screening procedures a total of 16 healthy, adult non-smokers were enrolled in the study, of which 9 completed all treatment groups.

TABLE 8

Primary Analysis of Oxycodone, Noroxycodone and Oxymorphone (Bioequivalence), Full PK data set:

| | | Test/Reference | | | | | |
|---|---|---|---|---|---|---|---|
| | | Test | | Reference | | | |
| | | N | Mean | n | Mean | Ratio (%) | 90% CI | P-value |
| | | Oxycodone | | | | | | |
| 6.0 mm vs Reference | $AUC_{(0-48\,h)}$ (nmol*h/L) | 12 | 574.7 | 11 | 547.8 | 104.9 | (95.8, 115.0) | 0.3790 |
| | $AUC_{(0-inf)}$ nmol*h/L) | 12 | 575.0 | 11 | 549.6 | 104.6 | (95.3, 114.8) | 0.4162 |
| | $C_{max}$ (nmol/L) | 12 | 45.4 | 11 | 52.2 | 87.0 | (79.0, 95.8) | 0.0201 |

TABLE 8-continued

Primary Analysis of Oxycodone, Noroxycodone and Oxymorphone (Bioequivalence), Full PK data set:

| | | Test | | Reference | | | | |
|---|---|---|---|---|---|---|---|---|
| | | N | Mean | n | Mean | Ratio (%) | 90% CI | P-value |
| 7.5 mm vs Reference | $AUC_{(0-48\,h)}$ (nmol*h/L) | 12 | 526.6 | 11 | 547.8 | 96.1 | (87.6, 105.5) | 0.4756 |
| | $AUC_{(0-inf)}$ nmol*h/L) | 12 | 529.1 | 11 | 549.6 | 96.3 | (87.6, 105.8) | 0.4992 |
| | $C_{max}$ (nmol/L) | 12 | 37.4 | 11 | 52.2 | 71.7 | (65.0, 79.1) | <.0001 |
| 9.0 mm vs Reference | $AUC_{(0-48\,h)}$ (nmol*h/L) | 11 | 534.9 | 11 | 547.8 | 97.7 | 88.9, 107.3 | 0.6711 |
| | $AUC_{(0-inf)}$ nmol*h/L) | 11 | 542.6 | 11 | 549.6 | 98.7 | 89.7, 108.7 | 0.8222 |
| | $C_{max}$ (nmol/L) | 11 | 31.4 | 11 | 52.2 | 60.1 | 54.5, 66.4 | <.0001 |
| Noroxycodone | | | | | | | | |
| 6.0 mm vs Reference | $AUC_{(0-48\,h)}$ (nmol*h/L) | 12 | 606.6 | 11 | 576.3 | 105.3 | (97.8, 113.3) | 0.2469 |
| | $AUC_{(0-inf)}$ nmol*h/L) | 12 | 612.8 | 11 | 586.5 | 104.5 | (97.3, 112.3) | 0.3064 |
| | $C_{max}$ (nmol/L) | 12 | 37.3 | 11 | 38.3 | 97.4 | (90.9, 104.3) | 0.5175 |
| 7.5 mm vs Reference | $AUC_{(0-48\,h)}$ (nmol*h/L) | 12 | 508.2 | 11 | 576.3 | 88.2 | (81.8, 95.1) | 0.0082 |
| | $AUC_{(0-inf)}$ nmol*h/L) | 12 | 519.1 | 11 | 586.5 | 88.5 | (82.3, 95.2) | 0.0084 |
| | $C_{max}$ (nmol/L) | 12 | 28.9 | 11 | 38.3 | 75.6 | (70.5, 81.1) | <.0001 |
| 9.0 mm vs Reference | $AUC_{(0-48\,h)}$ (nmol*h/L) | 11 | 540.1 | 11 | 576.3 | 93.7 | (86.9, 101.1) | 0.1575 |
| | $AUC_{(0-inf)}$ nmol*h/L) | 11 | 565.9 | 11 | 586.5 | 96.5 | (89.6, 103.9) | 0.4185 |
| | $C_{max}$ (nmol/L) | 11 | 38.3 | 11 | 25.6 | 67.0 | (62.4, 71.9) | <.0001 |
| Oxymorphone | | | | | | | | |
| 6.0 mm vs Reference | $AUC_{(0-48\,h)}$ (nmol*h/L) | 12 | 9.6 | 11 | 11.5 | 83.6 | (69.5, 100.6) | 0.1100 |
| | $AUC_{(0-inf)}$ nmol*h/L) | 11 | 14.9 | 9 | 16.4 | 90.8 | (78.0, 105.6) | 0.2829 |
| | $C_{max}$ (nmol/L) | 12 | 0.7 | 11 | 0.8 | 87.5 | (76.9, 99.5) | 0.0882 |
| 7.5 mm vs Reference | $AUC_{(0-48\,h)}$ (nmol*h/L) | 12 | 9.2 | 11 | 11.5 | 80.1 | (66.3, 96.7) | 0.0551 |
| | $AUC_{(0-inf)}$ nmol*h/L) | 11 | 14.8 | 9 | 16.4 | 90.1 | (77.3, 104.9) | 0.2506 |
| | $C_{max}$ (nmol/L) | 12 | 0.6 | 11 | 0.8 | 75.7 | (66.4, 86.3) | 0.0012 |
| 9.0 mm vs Reference | $AUC_{(0-48\,h)}$ (nmol*h/L) | 11 | 10.4 | 11 | 11.5 | 90.4 | (74.7, 109.5) | 0.3778 |
| | $AUC_{(0-inf)}$ nmol*h/L) | 10 | 18.7 | 9 | 16.4 | 113.9 | (97.5, 133.0) | 0.1635 |
| | $C_{max}$ (nmol/L) | 11 | 0.5 | 11 | 0.8 | 70.6 | (61.9, 80.6) | 0.0001 |

TABLE 9

Endpoints for Oxycodone

| Treatment | 6.0 mm | 7.5 mm | 9.0 mm | Reference |
|---|---|---|---|---|
| $AUC_{(0-48\,h)}$ (nmol*h/L): | | | | |
| Mean | 586 | 537 | 562 | 569 |
| Min, Max | 462-880 | 402-693 | 384-774 | 403-806 |
| $AUC_{(0-inf)}$ (nmol*h/L): | | | | |
| Mean | 587 | 540 | 571 | 571 |
| Min, Max | 461-882 | 414-695 | 387-778 | 405-811 |
| $C_{max}$ (nmol): | | | | |
| Mean | 46 | 38 | 33 | 54 |
| Min, Max | 32-59 | 27-56 | 23-45 | 39-79 |
| Residual area (Pct.): | | | | |
| Mean | 0 | 1 | 1 | 0 |
| Min, Max | 0-0 | 0-3 | 0-7 | 0-1 |

TABLE 9-continued

Endpoints for Oxycodone

| Treatment | 6.0 mm | 7.5 mm | 9.0 mm | Reference |
|---|---|---|---|---|
| $T_{max}$ (h): | | | | |
| Mean | 4.9 | 4.4 | 4.2 | 2.2 |
| Min, Max | 2.5-10.0 | 2.0-6.0 | 1.0-6.0 | 0.7-4.0 |
| $T_{(1/2)}$(h): | | | | |
| Mean | 4.5 | 5.2 | 5.7 | 5.2 |
| Min, Max | 3.5-5.5 | 4.1-10.3 | 3.7-12.5 | 4.2-6.3 |
| Elimination rate (1/h): | | | | |
| Mean | 0.16 | 0.14 | 0.13 | 0.14 |
| Min, Max | 0.13-0.20 | 0.07-0.17 | 0.06-0.19 | 0.11-0.17 |
| MRT (h): | | | | |
| Mean | 10.0 | 11.9 | 15.6 | 10.1 |
| Min, Max | 8.1-11.6 | 9.2-14.0 | 13.1-21.7 | 9.5-10.7 |
| Proportion $AUC_{(0-Tmax)}$ (Pct.): | | | | |
| Mean | 26 | 20 | 15 (7) | 12 |
| Min, Max | 11-50 | 9-30 | 3-25 | 2-24 |

The protraction index was determined, and the data below in table 10 are derived from the oxycodone concentration profile obtained in the individuals, which participated in this study.

TABLE 10

Protraction index

| 6 mm | 7.5 mm | 9 mm | Reference |
|---|---|---|---|
| $(AUC_{0-24\,h}/24\,h)/C_{max}$ | | | |
| 0.48 | 0.56 | 0.64 | 0.47 |
| 0.48 | 0.50 | 0.50 | 0.38 |
| 0.48 | 0.47 | 0.55 | 0.41 |
| 0.45 | 0.46 | 0.53 | 0.32 |
| 0.60 | 0.58 | 0.56 | 0.44 |
| 0.52 | 0.63 | 0.48 | 0.37 |
| 0.59 | 0.52 | 0.68 | 0.50 |
| 0.54 | 0.68 | 0.53 | 0.46 |
| 0.51 | 0.58 | 0.63 | 0.33 |
| 0.51 | 0.59 | 0.51 | 0.47 |
| 0.51 | 0.56 | 0.54 | 0.49 |
| 0.55 | 0.53 | 0.54 | — |
| 0.62 | — | — | — |

TABLE 10-continued

Protraction index

| 6 mm | 7.5 mm | 9 mm | Reference |
|---|---|---|---|
| Mean | | | |
| 0.53 | 0.55 | 0.56 | 0.42 |
| Min | | | |
| 0.45 | 0.46 | 0.48 | 0.32 |
| Max | | | |
| 0.62 | 0.68 | 0.68 | 0.50 |

Figure 5:
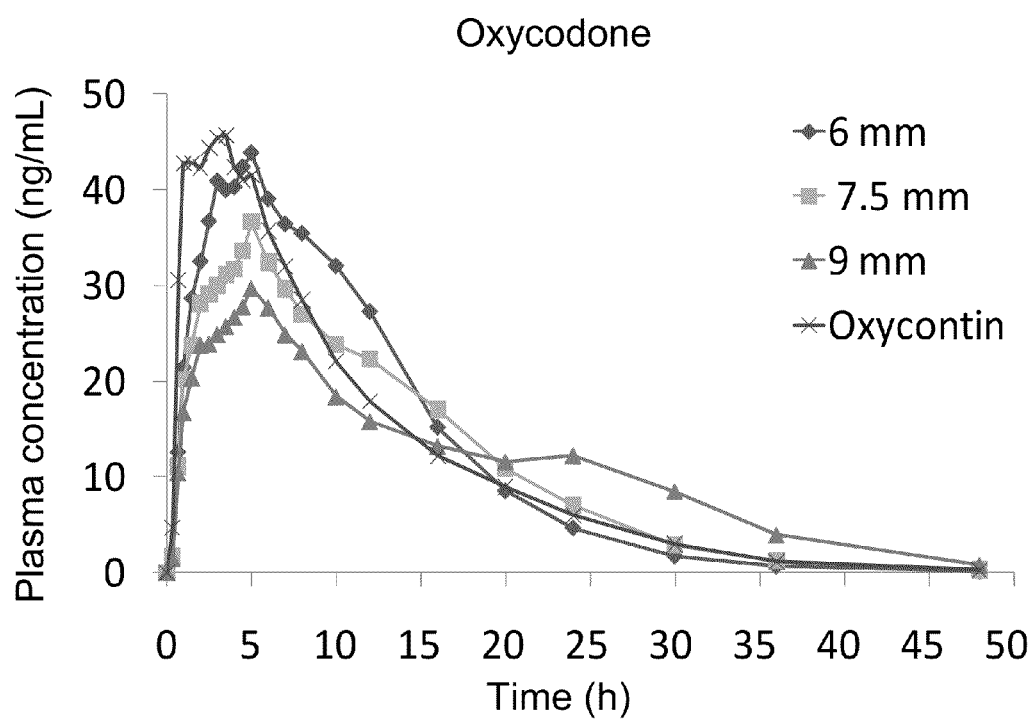
FIG. 5 shows the mean oxycodone plasma concentration (ng/mL) versus time (h) curve after single dose administration by dose group (0-48 h). 6 mm is treatment A, 7.5 mm is treatment B, 9 mm is treatment C and Oxycotin® is treatment D.
Figure 6:
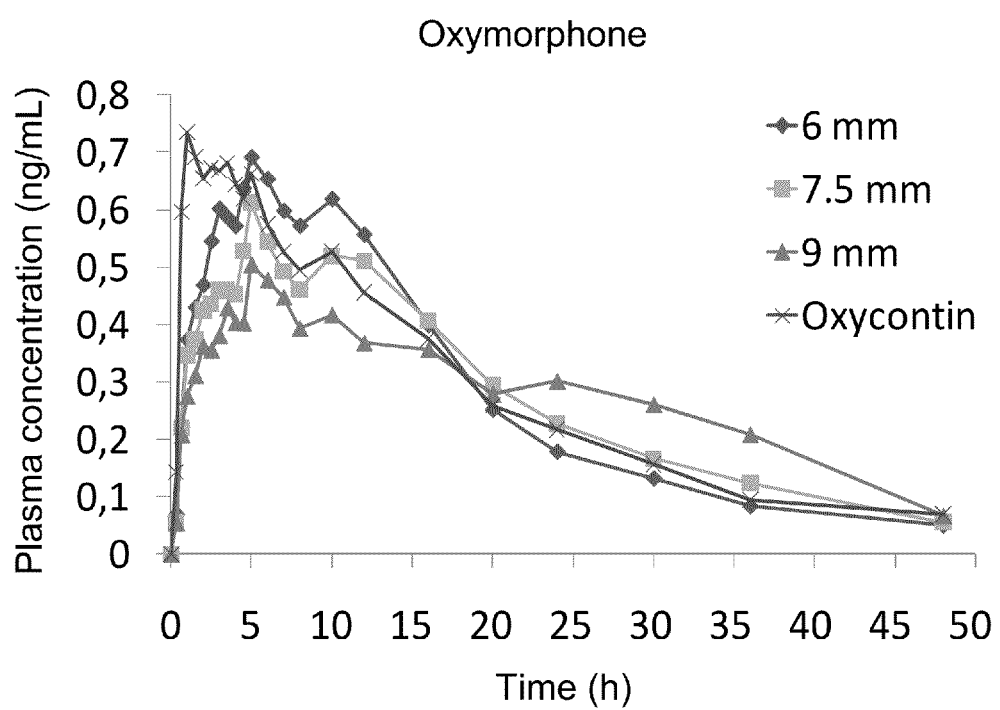
FIG. 6 shows the mean oxymorphone plasma concentration (ng/mL) versus time (h) curve after single dose administration by dose group (0-48 h). 6 mm is treatment A, 7.5 mm is treatment B, 9 mm is treatment C and Oxycotin® is treatment D.
Figure 7:
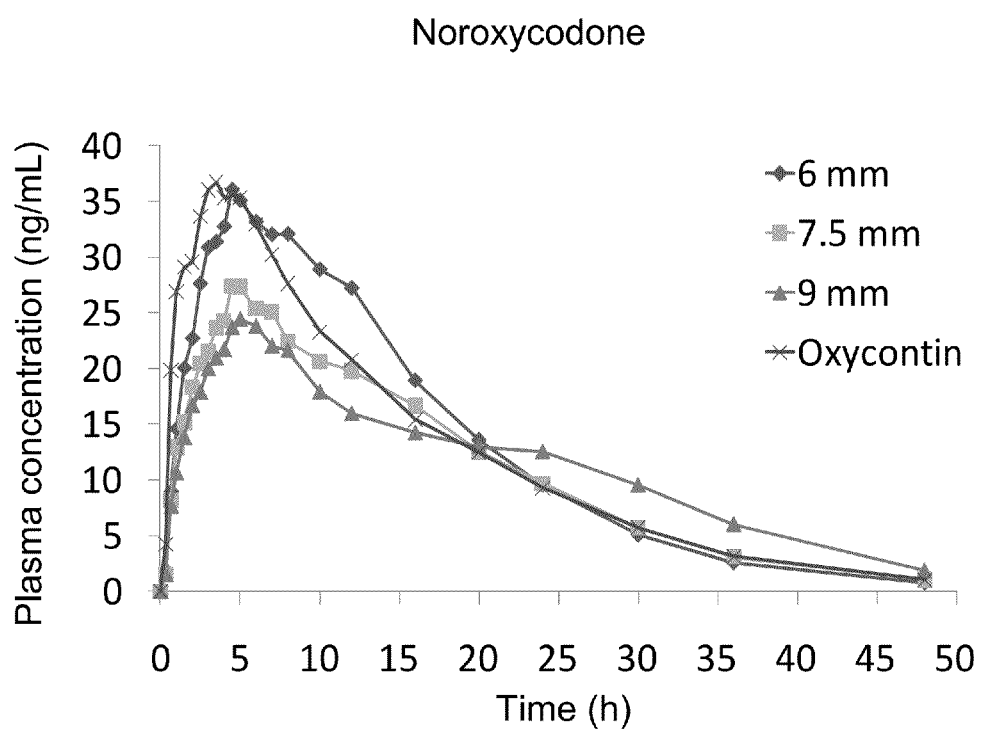
FIG. 7 shows the mean noroxycodone plasma concentration (ng/mL) versus time (h) curve after single dose administration by dose group (0-48 h). 6 mm is treatment A, 7.5 mm is treatment B, 9 mm is treatment C and Oxycotin® is treatment D.

FIGS. 5 to 7 show the mean plasma concentration versus time profiles for oxycodone, oxymorphone and noroxycodone after single dose administration by dose group (0-48 h)

Safety Results

No severe, significant, or serious adverse events were reported during the study. The most frequently occurring adverse events were expected or procedure-related and were mild or moderate in intensity Discussion From, the descriptive summaries of $AUC_{(0-48)}$ and $AUC_{(0-inf)}$ in Table 8 and 9, it was clear that the reference group had similar values of $AUC_{(0-48)}$ and $AUC_{(0-inf)}$ compared to the values for the test tablets. $C_{max}$ decreased with increasing size of the tablets. The pattern was repeated for the metabolites noroxycodone and oxymorphone. The elimination rate was almost the same for all four treatment groups. Mean MRT increased with increasing size of the tablet, with the reference group matching the 6.0 mm group. The mean proportion of $AUC_{(0-Tmax)}$ decreased with increasing size of the tablet, as with $AUC_{0-48}$ and $C_{max}$.

The ratio for $C_{max}$ showed a decreasing trend with increasing size of tablets. It was indicated that the 6.0 mm tablet was closest to the reference tablet, as the 90% confidence intervals for $C_{max}$ were 79.0-95.8 and that the 9.0 mm tablet had the most sustained profile, with a potential for QD (once daily) dosing.

Method for SS Simulation

The individual steady state data in the time interval [0 h, 24 h] were estimated as a sum of two components a) the sample values in the [0 h, 24 h] interval and b) estimated tail values in the interval [24 h, infinity], for example the estimated value at 1 hour on day 2, 3, 4 etc. This corresponds to the superimposition principle. The tail was assumed to follow the standard one-compartment elimination (i.e. exponential function), and was estimated based on sample data from 24-48 hours for Oxycodone and derivatives.

Steady State Results

TABLE 11

Summery of Steady State parameters

| Analyte | Treatment | | Peak (ng/mL) | Trough (ng/mL) | Trough/Peak Ratio | $T_{max}$ (Hours) |
|---|---|---|---|---|---|---|
| Oxycodone | Reference | N | 11 | 11 | 11 | 11 |
| | | Mean | 58.78 | 6.39 | 0.11 | 2.20 |
| | | Median | 60.29 | 5.89 | 0.11 | 2.50 |
| | | Range | 41.31-85.57 | 4.35-9.81 | 0.09-0.14 | 0.67-4.0 |
| | Test 6.0 mm | N | 13 | 13 | 13 | 13 |
| | | Mean | 48.04 | 4.44 | 0.09 | 4.89 |
| | | Median | 43.57 | 3.92 | 0.08 | 5.00 |
| | | Range | 33.80-60.94 | 1.56-7.91 | 0.04-0.17 | 2.50-10.0 |
| | Test 7.5 mm | N | 12 | 12 | 12 | 12 |
| | | Mean | 42.22 | 6.95 | 0.17 | 4.38 |
| | | Median | 40.47 | 6.30 | 0.16 | 4.75 |
| | | Range | 34.22-58.74 | 2.62-11.08 | 0.07-0.32 | 2.00-6.0 |

TABLE 11-continued

Summery of Steady State parameters

| Analyte | Treatment | | Peak (ng/mL) | Trough (ng/mL) | Trough/Peak Ratio | $T_{max}$ (Hours) |
|---|---|---|---|---|---|---|
| | Test 9.0 mm | N | 11 | 11 | 11 | 11 |
| | | Mean | 42.42 | 13.86 | 0.33 | 4.23 |
| | | Median | 39.73 | 12.30 | 0.31 | 4.50 |
| | | Range | 31.38-58.58 | 9.31-19.84 | 0.25-0.43 | 1.00-6.0 |

Figure 8:
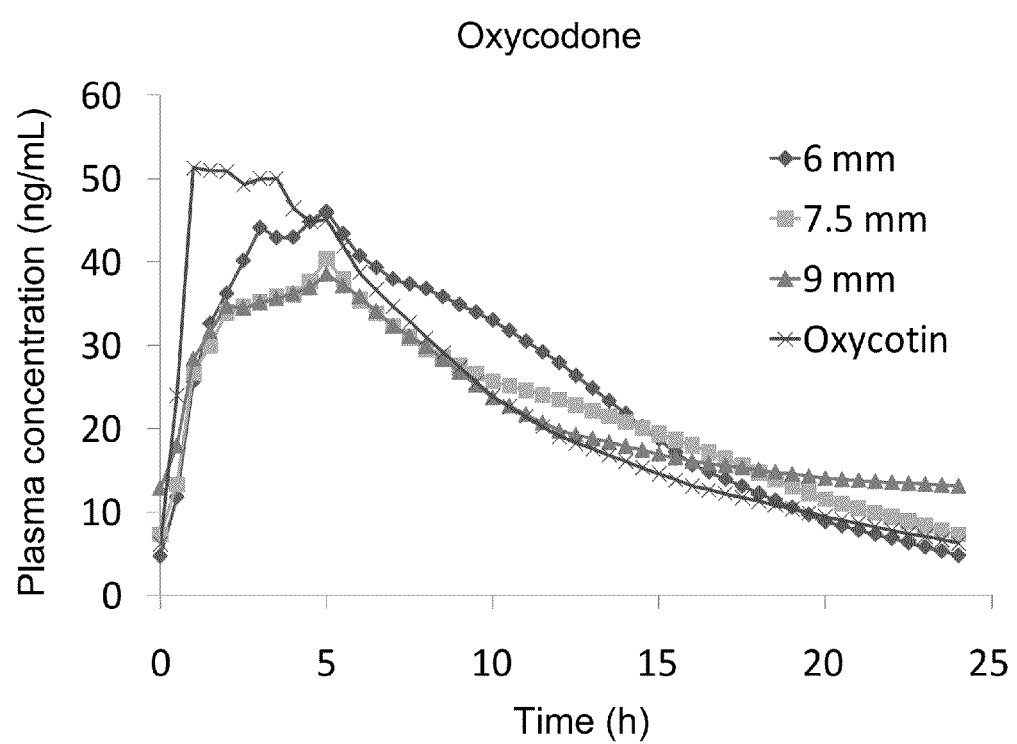
FIG. 8 shows an estimated steady state oxycodone curve, plasma concentration (ng/mL) versus time (h). 6 mm is treatment A, 7.5 mm is treatment B, 9 mm is treatment C and Oxycotin® is treatment D.

FIG. 8 shows an estimated steady state oxycodone curve.

From FIG. 8, it is seen that, in this study, the concentration profile curve of oxycodone flattens with an increase of size of the tablet, and an increase in the tablet size correlated to a decrease in $C_{max}$.

The individual steady state data [0 h, 24 h] is estimated as sum of observed data in the [0 h, 24 h] interval and estimated tail values [24 h, infinity]. Peak and trough were derived from these individual steady state data. The tails were estimated by standard one-compartment terminal elimination approach.

The pattern of increasing Trough/$C_{max}$ ratio with increasing length for mean oxycodone plasma concentrations is similar for the active metabolites mean noroxycodone and mean oxymorphone plasma.

Conclusions

The curve demonstrates that the pharmaceutical compositions prepared as described herein facilitate controlled delivery of active drug substances and that the geometry of such compositions can be adjusted to achieve desired, prolonged release of drug suited to once daily dosing.

It is commonly known that enterohepatic cycling causes a multiple peak phenomenon in the concentration-time profiles. Oxycodone does not show enterohepatic cycling.

Example 3

Compositions

The tablets formulated and used in the Examples are a combination of a matrix polymer system and a water-impermeable, essentially non-erodible shell (coating) partly covering this matrix. The active drug substance is dispersed and/or dissolved in the matrix.

The active drug substance is released substantially by surface erosion. The erosion of the matrix occurs when water diffuses into the matrix at a constant rate, leading to polymer hydration, swelling, disentanglement and dissolution.

A cylindrical shaped shell (coating) with a well defined surface area in both ends of the tablet leads to constant dissolution because of a constant release area. Accordingly, a zero-order release mechanism can be obtained. The shell (coating) can formulated such that it is slowly degradable and passes substantially (or entirely) intact through the GI tract and is excreted with feces. For tablets of a given length, extended release over a pre-defined period of time can be achieved, and as illustrated by the examples provided herein, in certain embodiments, tablets with a length in a range selected from a range of 8 to 10 mm and a range of 9 mm to 9.5 mm can be formulated to provide in vivo efficacy for 24 hours.

Geometry

By varying the size of the tablet and the thickness of the shell (coating), and thereby the matrix weight and size of the erosion area controlled release properties can by varied. Thus, the release area can be adjusted to alter the rate of which drug is released, and the length of the matrix can be adjusted to alter the duration of the release of drug. It is thus possible, if desired, to use the same matrix composition for all strengths that is needed. By varying the length of the tablet, keeping the volume fixed, it is possible to vary dissolution time with a fixed matrix composition. Thus, the duration of the release depend on the length of the composition. The rate of release (mg/h) may depend on the release area. To increase the strength of a pharmaceutical composition without changing the duration of the dissolution process, the length is kept constant while the area may be increased proportionally with the dose. The pharmaceutical compositions disclosed herein, therefore, enable formulations with different release properties without changing chemistry of the formulation.

The release rate of an active drug substance can also be altered by varying matrix composition. For example the dissolution rate of the matrix depends on ingoing components solubility, hydration rate and disentanglement rate among other properties. Accordingly, the dissolution rate may be increased by choosing hydrophilic or low molecular weight components in the matrix.

Table 12 discloses a preparation according to the invention controlling release by tablet length. These preparations were used in Example 2.

The composition was prepared by two component injection molding. The matrix volume was 125 mm³ and the lengths of the different dosage forms were 6 mm, 7.5 mm and 9 mm, respectively.

TABLE 12

| Component | Function | Quantity per unit (mg) | % w/w |
|---|---|---|---|
| Matrix | | | |
| Oxycodone hydrochloride | Active ingredient | 40.0 | 26.8 |
| Polyethylene oxide 200,000 | Carrier | 38.4 | 25.7 |
| Polyethylene oxide 300,000 | Carrier | 29.9 | 20.0 |
| Poloxamer 188 | Co-carrier, Plasticizer | 14.9 | 10.0 |
| Poloxamer 407 | Co-carrier, Plasticizer | 20.9 | 14.0 |
| Butylhydroxytoluene | Antioxidant, Stabilizer | 0.07 | 0.5 |
| Eudragit L100-55 | Carrier, Stabilizer | 4.48 | 3.0 |
| Total, matrix | | 148.7 | 100.0 |
| Shell (coating) | | | |
| Ethylcellulose | Coat material | 84.2 | 87.0 |
| Cetostearyl alcohol | Plasticizer | 10.1 | 12.0 |
| Titanium dioxide | Colorant | 0.97 | 1.0 |
| Total, shell (coating) | | 96.8 | 100.0 |
| Total | | 245.4 | |

The release time in an in vitro study (tested in an USP 2 apparatus at 50 rpm and pH 6.8) is proportional to the length of the tablet. The release time is shown in Table 13.

TABLE 13

| Batch | Release time (release) |
|---|---|
| 6 mm length (batch no. 08-0088-114) | 405 min (94%) |
| 7.5 mm length (batch no. 08-0089-114) | 510 min (88%) |
| 9 mm length (batch no. 08-0090-114) | 600 min (88%) |

Figure 9:
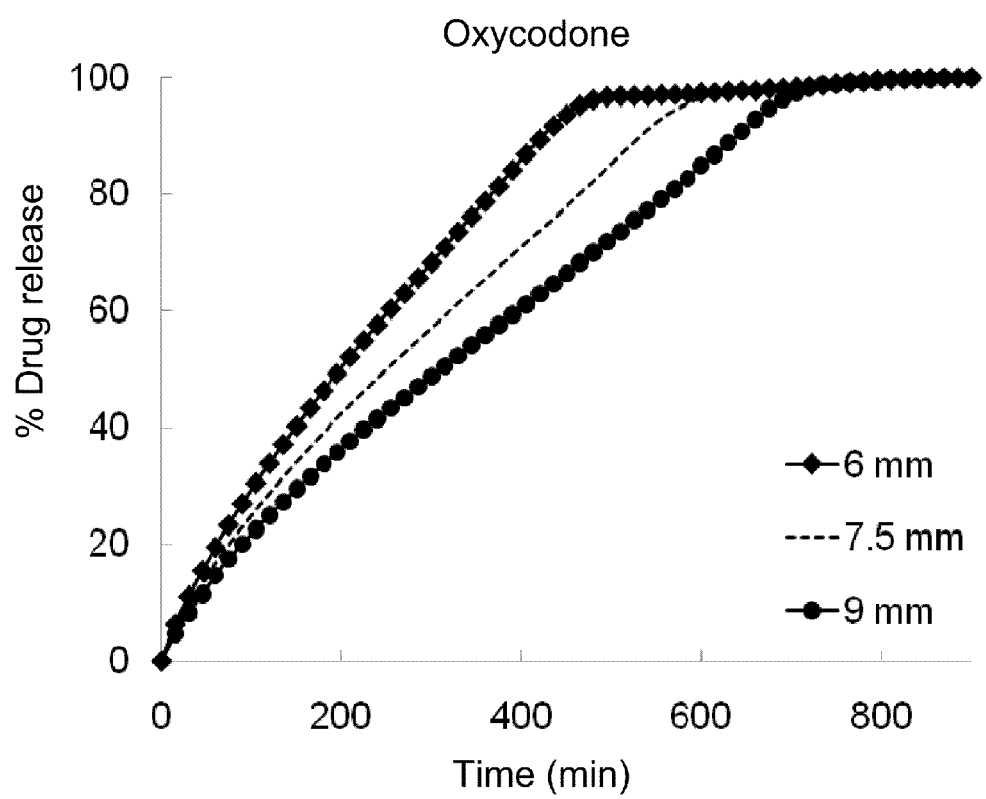
FIG. 9 shows the relationship between release times (% drug release versus time (minutes)) in vitro for a pharmaceutical composition according to the present description containing oxycodone 40 mg versus tablet length 6, 7.5 and 9 mm.

The relationship between release time and tablet length is shown in FIG. 9.

Table 14 discloses compositions designated formulation A and B.

Figure 10:
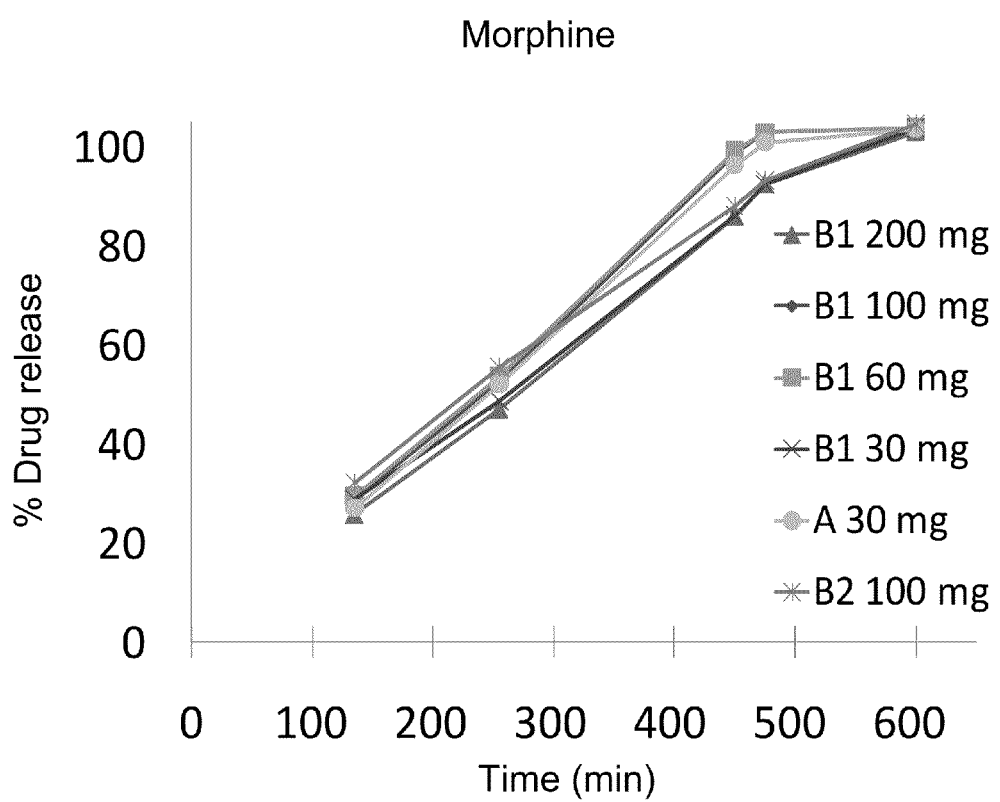
FIG. 10 shows in vitro dissolution results (drug release (%) versus time (minutes)) of pharmaceutical composition A (30 mg morphine), B1 (30, 60, 100 and 200 mg morphine) and B2 (100 mg morphine) according to the present description.

The compositions were prepared by two component injection molding. Two different formulations with different compositions were tested. Both formulations showed the same dissolution properties as tested in an USP 2 apparatus at 50 rpm and pH 6.8 (see FIG. 10). The two formulations were tested in two different tablet shapes: round (formulation A) and elliptical (formulation B). Formulation B was tested in different sizes, systematically varying volume and release area. It was found that the release duration for these formulations did not vary with volume, area or shape, but appeared to be dependent on the length. The dose was released proportionally to the release area, such that each composition released the complete dose (100%) at the same timepoint.

TABLE 14

| | Amount per tablet (% w/w) | | Function |
|---|---|---|---|
| Components | Form. A | Form. B | |
| Matrix | 100 | 100 | |
| Morphine sulfate pentahydrate | 16.0 | 51.5 | Active ingredient |
| Polyethylene oxide 200 000 | 71.4 | — | Carrier, release modifier |
| Polyethylene oxide 300 000 | — | 32.0 | Carrier, release modifier |
| Poloxamer 188 | — | 13.4 | Co-carrier, Plasticizer |
| Mannitol | 10.0 | 3.0 | Release modifier and stabilizer |
| Butylated hydroxytoluene (BHT) | — | 0.1 | Antioxidant, Stabilizer |
| Vitamin E Polyethylene Glycol Succinate (TPGS) | 2.6 | — | Stabilizer |
| Shell (coating) | 100 | 100 | |
| Ethylcellulose | 87.0 | 87.0 | Coat material |
| Cetostearyl alcohol | 12.0 | 12.0 | Plasticizer |
| Titanium dioxide | 1.0 | 1.0 | Coloring agent, UV stabiliser |

TABLE 15

| Shape | Batch no. | Length (mm) | Volume (mm$^3$) | Release area (mm$^2$) | Dose (mg) |
|---|---|---|---|---|---|
| Round | 08-0141-066 | 9 | 150 | 16.67 | 30 |
| Ellipse | 08-0140-066 | 7.5 | 42.08 | 5.61 | 30 |
| ellipse | 08-0138-066 | 7.5 | 89.94 | 11.99 | 60 |
| ellipse | 08-0137-066 | 7.5 | 150.2 | 20 | 100 |
| Ellipse | 08-0139-066 | 7.5 | 300.02 | 40 | 200 |

Table 16 and 17 shows preparations according to the invention controlling the release by tablet length. These preparations were used in the study described in Example 1.

Compositions were prepared by injection molding. Two formulations were prepared: a medium load composition tested in three different tablet lengths; and a high load formulation tested in 9 mm length unit of half the volume. The medium load formulations were shown to release in dissolution test (USP 2, pH 6.8, 50 RPM) with durations that were proportional to the tablet length. The high load formulation was adjusted by chemical formulation to a release time that was intermediate of the medium formulation release times.

TABLE 16

| | | Formulation A1-A3 | | | | | |
|---|---|---|---|---|---|---|---|
| | | Formulation A1 20 mg medium load 6.0 mm, length Quantity per unit | | Formulation A2 20 mg medium load 7.5 mm, length Quantity per unit | | Formulation A3 20 mg medium load 9 mm, length Quantity per unit | |
| Component | Function | (mg) | (% w/w) | (mg) | (% w/w) | (mg) | (% w/w) |
| Matrix | | | | | | | |
| Hydrocodone bitartrate | Active ingredient | 20 | 13.6 | 20 | 13.6 | 20 | 13.6 |
| Polyethylene oxide 200,000 | Carrier | 77.8 | 52.9 | 77.8 | 52.9 | 77.8 | 52.9 |
| Polyethylene oxide 300,000 | Carrier | 14.7 | 10.0 | 14.7 | 10.0 | 14.7 | 10.0 |
| Poloxamer 188 | Co-carrier, Plasticizer | 23.5 | 16.0 | 23.5 | 16.0 | 23.5 | 16.0 |
| Poloxamer 407 | Co-carrier, Plasticizer | 5.9 | 4.0 | 5.9 | 4.0 | 5.9 | 4.0 |
| Butylhydroxytoluene | Antioxidant, Stabilizer | 0.7 | 0.5 | 0.7 | 0.5 | 0.7 | 0.5 |
| Mannitol | Carrier, Stabilizer | 4.4 | 3 | 4.4 | 3 | 4.4 | 3 |
| Total, matrix | | 147 | 100 | 147 | 100 | 147 | 100 |

TABLE 16-continued

| | | Formulation A1-A3 | | | | | |
|---|---|---|---|---|---|---|---|
| | | Formulation A1 20 mg medium load 6.0 mm, length Quantity per unit | | Formulation A2 20 mg medium load 7.5 mm, length Quantity per unit | | Formulation A3 20 mg medium load 9 mm, length Quantity per unit | |
| Component | Function | (mg) | (% w/w) | (mg) | (% w/w) | (mg) | (% w/w) |
| Shell (coating) | | | | | | | |
| Ethylcellulose | Coat | 80.9 | 87 | 95.7 | 87 | 145.3 | 87 |
| Cetostearyl alcohol | Plasticizer | 11.2 | 12 | 13.2 | 12 | 20.0 | 12 |
| Titanium dioxide | Colorant | 0.93 | 1 | 1.1 | 1 | 1.7 | 1 |
| Total, shell (coating) | | 93 | 100 | 110 | 100 | 167 | 100 |
| Total | | 240 | 200 | 257 | 200 | 314 | 200 |

TABLE 17

| | | Formulation B1 | |
|---|---|---|---|
| | | 20 mg high load (9.0 mm length) Quantity per unit | |
| Component | Function | (mg) | % w/w |
| Matrix | | | |
| Hydrocodone bitartrate | Active ingredient | 20.0 | 26.2 |
| Polyethylene oxide 200,000 | Carrier | 40.7 | 53.3 |
| Polyethylene oxide 300,000 | Carrier | 7.6 | 10.0 |
| Poloxamer 188 | Co-carrier, Plasticizer | 7.6 | 10.0 |
| Butylhydroxytoluene | Antioxidant, Stabilizer | 0.4 | 0.5 |
| Total, matrix | | 76.3 | 100.0 |
| Shell (coating) | | | |
| Ethylcellulose | Coat material | 79.8 | 87.0 |
| Cetostearyl alcohol | Plasticizer | 11.0 | 12.0 |
| Titanium dioxide | Colorant | 0.9 | 1.0 |
| Total, shell (coating) | | 91.7 | 100 |
| Total | | 168 | 200 |

TABLE 18

| | Formulation | | | |
|---|---|---|---|---|
| Parameter | A1 6.0 mm length 08-0188-113 | A2 7.5 mm length 08-0189-113 | A3 9.0 mm length 08-0190-113 | B1 9.0 mm length 08-0191-113 |
| Release area (mm²) | 20.8 | 16.6 | 13.8 | 7 |
| Dimensions (mm) | | | | |
| Length | 6.0 | 7.5 | 9.0 | 9.0 |
| Short diameter | 4.7 | 4.3 | 4.4 | 3.4 |
| Long diameter | 9.4 | 8.5 | 8.3 | 5.6 |

Figure 12:
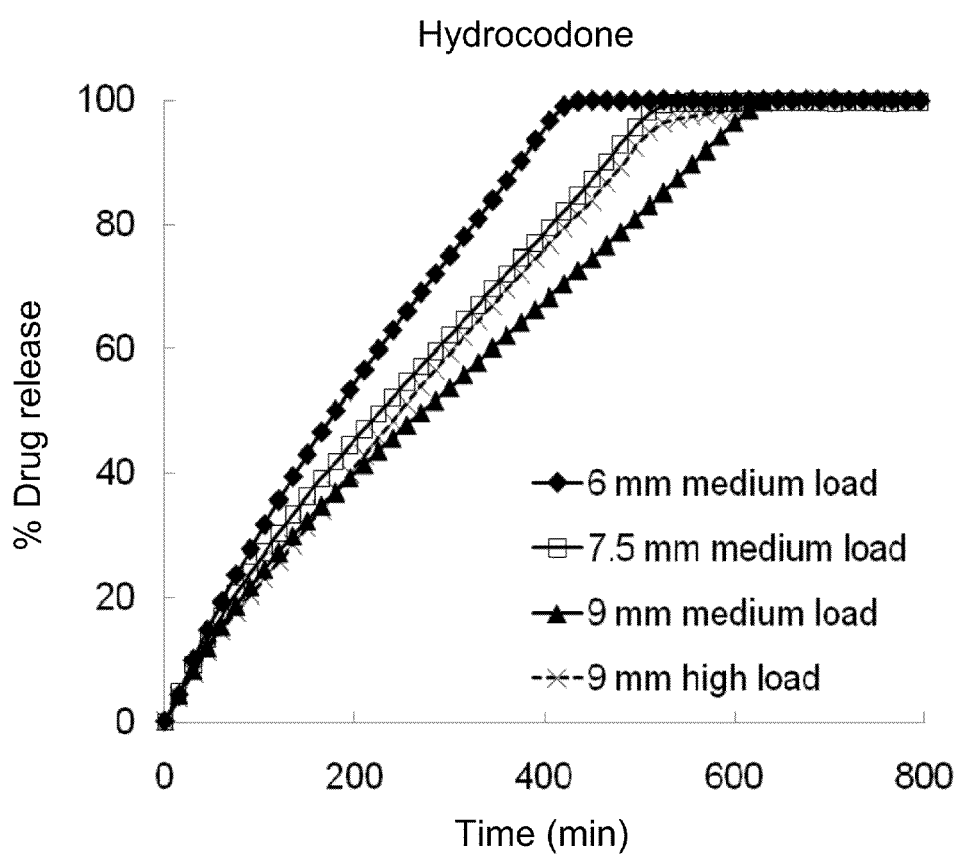
FIG. 12 shows the relationship between release times (% drug release versus time (minutes)) in vitro for a pharmaceutical composition according to the present description containing hydrocodone versus tablet length 6 mm (medium load), 7.5 mm (medium load), 9 mm (medium load) and 9 mm (high load).

FIG. 12 shows the release times for hydrocodone versus tablet length.

Example 4

A Single-period, Multiple-dose, Single-centre, Phase I Trial Evaluating the Steady-state Pharmacokinetic Profile of Egalet® Morphine 30 mg (Formulation A) Controlled Extended Release Dosage Unit in Healthy Volunteers Using Naltrexone Blockade The content of the Egalet® morphine 30 mg (Formulation A) controlled extended release dosage unit used in this study is described in detail in Example 3 herein above in Table 14 and was prepared according to the teachings of the present description. The shape was of the formulation used in this study was a round, 9.0 mm long, with a volume of 150 mm³ and a cross section area of 8,335 mm².

This study is also referred to as MP-EG-003 herein.

This was a single-centre, non-comparative, multiple-dose, phase I trial, performed under fasting conditions. Subjects were confined to the Clinical Research Facility from at least 14 hours before the first study drug administration (evening of Day −1, when the first administration of co-medication [naltrexone] was given) and were discharged from the clinic on Day 11, after the 36.0-hour post-dose blood draw. Subjects came back for all subsequent blood draws on Days 12, 13, 14, and 15. Naltrexone is an opioid receptor antagonist.

The number of subjects that enrolled, randomised and completed the study was 18 (8 females and 10 males).

TABLE 19

| | Treatment | |
|---|---|---|
| | Study Drug | Co-medication |
| Name | Egalet ® morphine Formulation A | Naltrexone hydrochloride (Revia ®) |
| Unit dose | 30 mg | 50 mg |
| Regimen | single dose of 1 × 30 mg controlled release dosage unit by oral administration for 10 consecutive days (Days 1 to 10) | single dose of 1 × 50 mg film coated tablet by oral administration on the following days: Day −1, 12 hours before the first morphine administration; Days 1 through 10: 1 hour before each morphine administration; Day 11: approximately 24 hours after the last morphine administration (immediately prior to next dose) |

The following pharmacokinetic parameters were calculated for morphine: $AUC_{0-24h}$, $T_{max}$, steady state $C_{max}$, steady state $C_{min}$, PTF, $AUC_{0-inf}$, $T_{1/2\ el}$, and $K_{el}$. The pharmacokinetic parameters listed above were also calculated for morphine-3-glucuronide and morphine-6-glucuronide. Additional pharmacokinetic parameters were MRT, HVD and $T_{75\%Cmax}$ (for morphine only). Also the protraction index was calculated for each individual with regard to the morphine concentration profile For purposes of evaluating safety, adverse events, vital signs (including pulse oxymetry and ECG measurements), and standard laboratory evaluations were conducted for each individual.

A single arm, non-comparative study, formal statistical analyses were not performed for the PK endpoints. Endpoints are summarized and represented by N, arithmetic and geometric mean, median, standard deviation, minimum and maximum.

The attainment of steady state was assessed based on log-transformed pre-dose plasma concentrations of morphine recorded on Days 4 to 10. In a repeated measures model with subject and day as factors, Day 10 concentration was compared to Days 4 to 9, respectively. The first day with a non-significant difference to Day 10 is considered steady state. Mean and individual curves of untransformed pre-dose plasma concentrations versus time (Days 4 to 11) were produced. The steady state analysis was repeated, including time since physical activity and time since last bowel movement as covariates in the model.

Results

Figure 13:
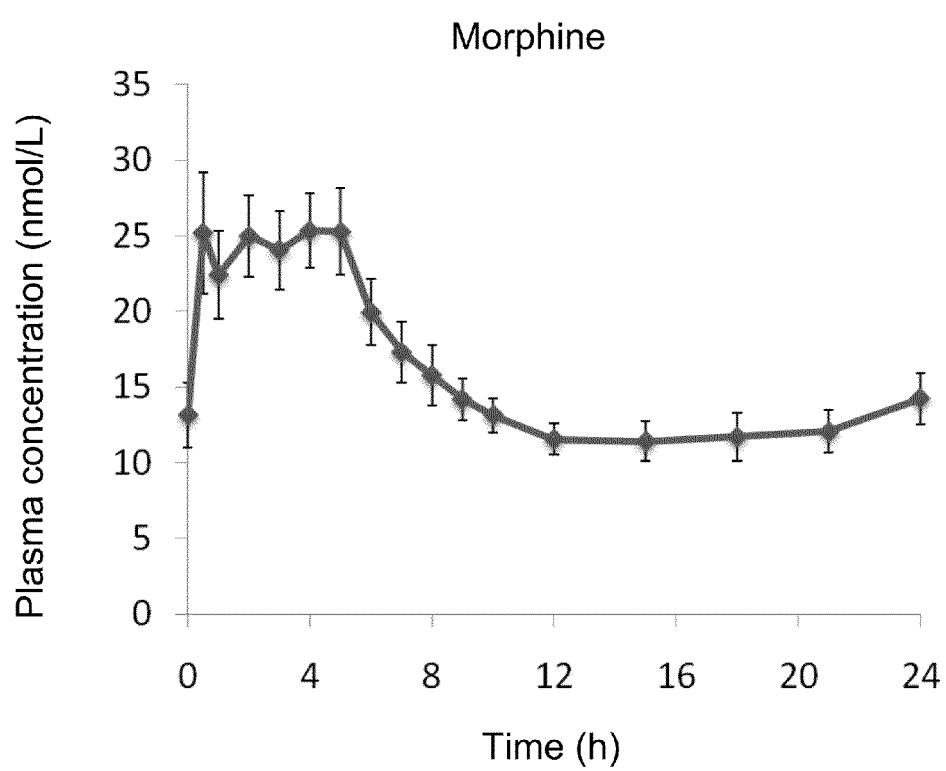
FIG. 13 shows the mean steady state morphine plasma concentration (nmol/l) versus time curve (0-24 h).

FIG. 13 shows the mean steady state morphine plasma concentration versus time curve (0-24 h).

Steady state was obtained already after 4 days of administration of the Egalet® morphine 30 mg (Formulation A) extended release dosage unit. As four (4) days was the earliest investigated time point, steady state may have been reached even earlier. Both the mean and individual concentration vs. time profiles indicate that the Egalet® morphine (Formulation A) dosage unit provided sustained release of clinically relevant amounts of morphine over a 24 hour period. The results of this study also indicated that the Egalet® morphine 30 mg ((Formulation A) extended release dosage unit was a candidate for providing either twice daily or once daily dosing of morphine. In some subjects, the morphine concentration decreased to a relatively low level at the 24 h time point. The co-administration of naltrexone may have influenced the PK-profiles and some of the PK endpoints. No severe, significant, or serious adverse events were reported during the study.

TABLE 20

| Pharmacokinetics - morphine | |
|---|---|
| Enrolled subjects | 18 |
| $AUC_{0-24\,h}$ (nmol*h/L) | |
| Geom. mean | 353 |
| Min, Max | 176-795 |
| $T_{Max}$ (h) | |
| Geom. mean | 1.54 |
| Min, Max | 0.50-5.05 |
| $C_{Max}$ (SS)(nmol/L) | |
| Geom. mean | 31.6 |
| Min, Max | 14.1-59.3 |
| $C_{Min}$ (SS)(nmol/L) | |
| Geom. mean | 6.9 |
| Min, Max | 1.6-23.4 |

TABLE 20-continued

| Pharmacokinetics - morphine | |
|---|---|
| $C_{24}$ (SS)(nmol/L) | |
| Geom. mean | 12.52 |
| Min, Max | 2.19-27.3 |

SS = steady state

Also, the Protraction index was determined, and the data below in Table 21 are derived from the steady state profiles obtained in the individuals, which participated in this study.

TABLE 21

| Protraction index | |
|---|---|
| ($AUC_{0-24\,h}$/24 h)/Cmax | |
| | 0.36 |
| | 0.34 |
| | 0.39 |
| | 0.36 |
| | 0.39 |
| | 0.34 |
| | 0.30 |
| | 0.35 |
| | 0.35 |
| | 0.36 |
| | 0.39 |
| | 0.35 |
| | 0.40 |
| | 0.29 |
| | 0.42 |
| | 0.39 |
| | 0.47 |
| Mean | 0.37 |
| Min | 0.29 |
| Max | 0.47 |

Example 5

A Single-Centre, Single-Dose, Randomised, Open-Label, 5-Way Crossover, Dose-Linearity Study of Egalet® Morphine 30, 60, 100 and 200 mg Controlled-Release Dosage Units in Healthy Volunteers Using Naltrexone Blockade Under Fasting Conditions This study is also referred to as MP-EG-005 herein.

Design

This was a single centre, open-label, single-dose, randomised, 5-way crossover, comparative bioavailability study, performed under fasting conditions to evaluate dose-linearity of the four strengths of Egalet® Morphine of Formulation B.

Treatments

In each treatment period, subjects were administered a single oral dose of either Egalet® Morphine of Formulation B (dosage unit of 30, 60, 100, or 200 mg) or Formulation A (two tablets of 30 mg) controlled-release dosage units on Day 1, in accordance with the subjects' randomization sequence. The content of the formulations are described in Table 14 herein above. The geometry of the formulations are described in Table 15 herein above, The treatment periods were separated by a washout of 7 days.

Treatment A: 1×30 mg Egalet® Morphine controlled-release dosage unit of Formulation B (length 7.5 mm) (08-0140-066).

Treatment B: 1×60 mg Egalet® Morphine controlled-release dosage unit of Formulation B (length 7.5 mm) (08-0138-066).

Treatment C: 1×100 mg Egalet® Morphine controlled-release dosage unit of Formulation B (length 7.5 mm) (08-0137-066).

Treatment D: 1×200 mg Egalet® Morphine controlled-release dosage unit of Formulation B (length 7.5 mm) (08-0139-066).

Treatment E: 2×30 mg Egalet® Morphine controlled-release dosage units of Formulation A (length 9 mm) (08-0141-066).

To alleviate or avoid opioid side effects that are expected in opioid-naïve subjects, naltrexone was administered as a 1×50 mg tablet with approximately 120 mL of water approximately 12 hours before morphine administration (Day −1), approximately 1 hour before morphine administration (Day 1), and approximately 24 hours post-morphine administration (Day 2).

Methodology

A total of 39 healthy, adult non-smokers signed the study-specific informed consent form and were confined for Period 1; of these subjects, 35 (18 males and 17 females) were enrolled and dosed in the study; 31 of these enrolled subjects completed the study. Prior to entering the trial, subjects completed all screening procedures. Upon arrival at the clinical facility for the confinement (Day −1) and once eligibility had been confirmed, subjects were sequentially allocated a two-digit subject number that corresponded to the randomisation scheme. All subjects received standardised meals throughout during their confinements, not less than 4 hours post-dose, approximately 9 hours post-dose, and an evening snack approximately 13 hours post-dose. With the exception of the volume administered at the time of the administration of morphine, fluids were not permitted from 1 hour before dosing to 1 hours post-morphine dose, but water was permitted ad libitum at all other times.

Sample Collection

Measurements of morphine plasma concentrations and secondary analysis with morphine-3-glucuronide and morphine-6-glucuronide plasma concentrations were performed at the following timepoints: pre-dose and 0.333, 0.667, 1.00, 2.00, 3.00, 4.00, 5.00, 6.00, 7.00, 8.00, 10.0, 12.0, 15.0, 18.0, 21.0, 24.0, 30.0, 36.0, and 48.0 hour post-dose.

Pharmacokinetic Parameters

The following PK parameters were calculated and summarised by standard non-compartmental methods for morphine plasma concentrations, morphine-3-glucuronide plasma concentrations, and morphine-6-glucuronide plasma concentrations. The morphine-3-glucuronide plasma concentrations and morphine-6-glucuronide plasma concentrations were included for supportive information.

1) $AUC_{0-t}$: area under the concentration-time curve from time zero to the last non-zero concentration
2) $AUC_{0-inf}$: area under the concentration-time curve from time zero to infinity (extrapolated)
3) $C_{max}$: maximum observed concentration
4) Residual area: calculated as $100*(1-AUC_{0-t}/AUC_{0-inf})$.
5) $T_{max}$: time of observed $C_{max}$
6) $T_{1/2\ el}$: elimination half-life
7) $K_{el}$: elimination rate constant
8) MRT: mean residence time
9) Proportion of AUC before $T_{max}$ Pharmacokinetic Methods The PK endpoints were calculated individually for each subject and dose based on the plasma concentrations obtained on Days 1-3 (0-48 h) within each period.

$AUC_{0-t}$

The area under the concentration-time-curve from time 0 h until the last concentration sample at time 48 h, $AUC_{0-t}$, were calculated by the linear trapezoidal method, using the actual sampling time points. If the last blood sample was taken less than 48 hours after drug administration, the 48 h values were extrapolated using the terminal elimination rate constant, $K_{el}$ as described below. If the last sample was taken after 48 hours, a 48 h value was estimated by interpolation. Intermediate missing values remained missing (equivalent to interpolating between neighbouring points when calculating AUC). Intermediate values below the limit of quantification (LOQ) were assigned a value of LOQ/2, while trailing values below LOQ were assigned a value of zero.

$AUC_{0-inf}$

The area under the concentration-time-curve from time 0 h until infinity was determined for profiles that did not return to zero within 48 hours. $AUC_{0-inf}$, was calculated as the sum of $AUC_{0-t}$ and $C_t/K_{el}$ where Ct was the last sample above LOQ.

$T_{max}$ and $C_{max}$ $T_{max}$ and $C_{max}$ were derived from the samples 0-48 h after drug administration. Actual sampling time points were used for $T_{max}$.

Residual Area:

Calculated as $100*(1-AUC_{0-t}/AUC_{0-inf})$ $T_{1/2\ el}$:

The elimination half-life $T_{1/2}$ was found by $Ln(2)/K_{el}$, (for calculation of $K_{el}$ refer to the below)

$K_{el}$:

The elimination rate constant, $K_{el}$ was the slope of the terminal part of the log-concentration-time-curve and was found using log-linear regression. The final four plasma concentrations above LOQ were included in the calculation as a minimum. However, the log-linear plots of plasma concentration were inspected and a different selection of data points could have been chosen to ensure that the time period represented the terminal elimination phase. Actual time values were used.

MRT:

The mean residence time was calculated as $MRT_{0-inf} = AUMC_{0-inf}/AUC_{0-inf}$ where $AUMC_{0-inf} = AUMC_{0-t} + t*C_t/K_{el} + C_t/(K_{el})^2$, and where $AUMC_{0-t}$ was the area under the first moment curve from time 0 until the last valid measurement at the time point t. $C_t$ was the last valid plasma concentration found at this time point, t.

% $AUC_{0-Tmax}$

Figure 14:
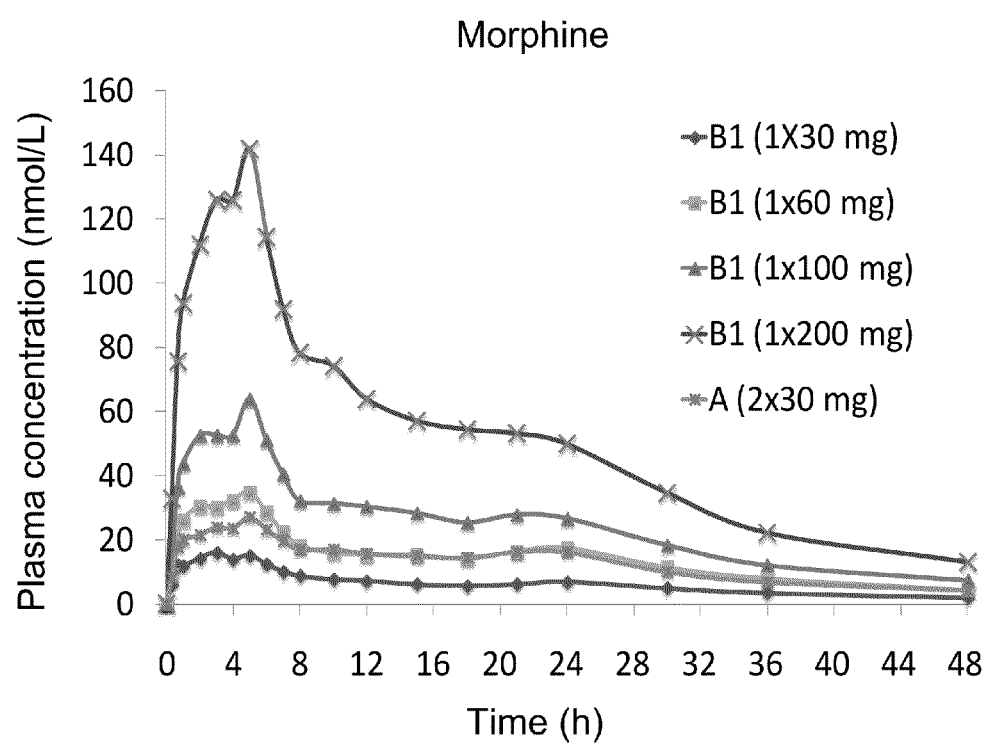
FIG. 14 shows the mean morphine plasma concentration (nmol/l) versus time curve by dose group (0-48 h).

The proportion of AUC before $T_{max}$ was found by $100*(AUC_{0-Tmax}/AUC_{0-inf})$ Pharmacokinetic Results As displayed in FIG. 14, below, there was a clear increase in the concentration of morphine with the increase in dosage. The curves of 1×60 mg Egalet® Morphine Formulation B and 2×30 mg Egalet® Morphine Formulation A were similar. During the first 8 hours, the plasma concentration of 1×60 mg Egalet® Morphine Formulation B was slightly higher than that of the 2×30 mg Egalet® Morphine Formulation A.

The metabolites morphine-3-glucuronide and morphine-6-glucuronide concentrations were proportional between strengths.

Individual plasma concentration profiles for each subject showed consistency across profiles for morphine, morphine-3-glucuronide, and morphine-6-glucuronide concentrations within each subject. For morphine, these relationships are also presented in Table 22. The results for $C_{max}$ displayed the same pattern as the results for $AUC_{0-48}$, and the results for $AUC_{0-48}$, and $C_{max}$ confirmed the patterns displayed by FIG. 14. The relationship between dosage and $AUC_{0-inf}$ was the same as for $AUC_{0-48}$.

TABLE 22

Endpoints for Morphine

| | Treatment | | | | |
|---|---|---|---|---|---|
| | 30 mg Form B | 60 mg Form B | 100 mg Form B | 200 mg Form B | 2 × 30 mg Form A |
| $AUC_{(0-48\,h)}$(nmol*h/L): | | | | | |
| Mean | 300 | 681 | 1175 | 2437 | 618 |
| Min-Max | 110-535 | 364-1127 | 756-2189 | 1371-4176 | 203-1008 |
| $C_{max}$ (nmol): | | | | | |
| Mean | 19 | 43 | 73 | 168 | 35 |
| Min-Max | 8-40 | 23-69 | 38-138 | 71-277 | 16-72 |
| $AUC_{(0-inf)}$(nmol*h/L): | | | | | |
| Mean | 381 | 823 | 1355 | 2702 | 728 |
| Min-Max | 117-1668 | 414-2582 | 784-2795 | 1483-4528 | 209-1324 |
| Residual area (Pct.): | | | | | |
| Mean | 13 | 13 | 11 | 9 | 13 |
| Min-Max | 0-74 | 1-75 | 2-44 | 0-20 | 1-43 |
| $T_{max}$ (h): | | | | | |
| Mean | 3 | 3 | 3 | 4 | 4 |
| Min-Max | 1-6 | 1-5 | 1-10 | 1-10 | 0-24 |
| $T_{(1/2)}$(h): | | | | | |
| Mean | 17 | 17 | 14 | 13 | 14 |
| Min-Max | 4-129 | 5-134 | 7-47 | 5-20 | 6-31 |
| Elimination rate (1/h): | | | | | |
| Mean | 0.06 | 0.06 | 0.06 | 0.06 | 0.06 |
| Min-Max | 0.01-0.17 | 0.01-0.13 | 0.01-0.10 | 0.03-0.14 | 0.02-0.12 |
| MRT (h): | | | | | |
| Mean | 27 | 29 | 24 | 21 | 25 |
| Min-Max | 9-178 | 14-186 | 13-61 | 12-29 | 9-49 |
| Proportion $AUC_{(0-Tmax)}$ (Pct.): | | | | | |
| Mean | 12 | 9 | 11 | 15 | 12 |
| Min-Max | 1-36 | 1-20 | 1-28 | 2-33 | 1-54 |

For morphine-3-glucuronide and morphine-6-glucuronide plasma concentrations, the relationship between dosage and $AUC_{0-48}$, $C_{max}$, and $AUC_{0-inf}$ was the same as for the morphine plasma concentrations. The pattern of the residual area and the elimination rate for morphine-3-glucuronide and morphine-6-glucuronide concentrations was also similar as to that of morphine. For both morphine-3-glucuronide and morphine-6-glucuronide concentrations, the mean $T_{max}$ was 4 hours.

Primary PK Analysis (Dose-linearity)

From the descriptive summaries of $AUC_{0-48}$ and $C_{max}$ in Table 23, it was clear that a dose response relationship was present for $AUC_{0-48}$ and $C_{max}$.

TABLE 23

Primary Analysis of Morphine (Dose-Linearity)

| | Coefficient for log-dose | Estimate | Std. Err. | 90% Confidence Interval | |
|---|---|---|---|---|---|
| | | | | Lower | Upper |
| Full PK Data Set: | | | | | |
| $AUC_{(0-48\,h)}$ (nmol*h/L) | B | 1.1171 | 0.02281 | 1.0792 | 1.1550 |
| $AUC_{(0-inf)}$ (nmol*h/L) | B | 1.0806 | 0.03317 | 1.0225 | 1.1358 |
| $C_{max}$ | B | 1.1365 | 0.02297 | 1.0983 | 1.1747 |
| Completers Only: | | | | | |
| $AUC_{(0-48\,h)}$ (nmol*h/L) | B | 1.1185 | 0.02310 | 1.0801 | 1.1569 |
| $AUC_{(0-inf)}$ (nmol*h/L) | B | 1.0826 | 0.03376 | 1.0265 | 1.1387 |
| $C_{max}$ | B | 1.1349 | 0.02310 | 1.0965 | 1.1733 |

Table 23 presents the analysis of dose-linearity for morphine concentration for $AUC_{0-48}$ and $C_{max}$.

The table showed that dose-linearity could be assumed, as the 90% confidence interval for β was fully contained within the interval 0.80-1.25 for $AUC_{0-48}$, $AUC_{0-inf}$ as well as for $C_{max}$, both for the full PK analysis set and for completers only. The estimates of coefficient for the log-dose, β, for the three parameters ranged from 1.08 to 1.14. This indicated that the bio-availability increased slightly more than proportionally with dose. However, since the confidence intervals were within the regulatory acceptance limits, this slight deviation was not considered clinically important.

The analysis of morphine-3-glucuronide and morphine-6-glucuronide concentrations confirmed the results for the morphine plasma concentration, as all 90% confidence intervals were contained within the interval 0.80-1.25 and all estimates of β were slightly larger than 1.

The co-administration of naltrexone may have influenced the PK-profiles and some of the PK endpoints.

Secondary PK Analysis of 1×60 mg Formulation B Versus 2×30 mg Formulation A

A secondary analysis comparing PK parameters provided by the 1×60 mg Formulation B and the 2×30 mg Formulation A was conducted. The results of the secondary analysis of morphine are presented in Table 24, which shows that the estimated ratios of means for $AUC_{0-48h}$ and $AUC_{0-inf}$ were 110.2 and 111.6, respectively, and the estimated ratio for $C_{max}$ was 121.7.

TABLE 24

Secondary Analysis of Morphine (Bioequivalence)

| | Means | | Form B/Form A | | |
|---|---|---|---|---|---|
| | Form. B | Form. A | | | |
| | (1 × 60 mg) | (2 × 30 mg) | Ratio | 90% CI | p-value |
| Full PK data set: | | | | | |
| $AUC_{(0-48\,h)}$ (nmol*h/L) | 642.3 | 583.0 | 110.2 | (102.7, 118.2) | 0.0235 |
| $AUC_{(0-inf)}$ (nmol*h/L) | 755.2 | 676.8 | 111.6 | (100.9, 123.5) | 0.0749 |
| $C_{max}$ (nmol/L) | 40.5 | 33.3 | 121.7 | (113.0, 131.2) | <.0001 |

TABLE 24-continued

Secondary Analysis of Morphine (Bioequivalence)

| | Means | | Form B/Form A | | |
|---|---|---|---|---|---|
| | Form. B | Form. A | | | |
| | (1 × 60 mg) | (2 × 30 mg) | Ratio | 90% CI | p-value |
| Completers only: | | | | | |
| $AUC_{(0-48\,h)}$ (nmol*h/L) | 654.7 | 591.3 | 110.7 | (103.0, 119.1) | 0.0218 |
| $AUC_{(0-inf)}$ (nmol*h/L) | 772.2 | 693.6 | 111.3 | (100.2, 123.7) | 0.0945 |
| $C_{max}$ (nmol/L) | 41.1 | 33.4 | 122.9 | (113.8, 132.8) | <.0001 |
| PK set-tail less 20%: | | | | | |
| $AUC_{(0-inf)}$ (nmol*h/L) | 714.4 | 624.9 | 114.3 | (104.6, 125.0) | 0.0141 |

Endpoints are log-transformed before analysis, and results are transformed back and presented as ratios. The model includes period and treatment as fixed effects and subject as a random effect.

Estimates and comparisons are based on the full model with all treatments included.

The mean is the geometric mean estimated from the model.

Secondary PK Analysis of 1×30 mg Formulation B Versus 1×30 mg Formulation A

A secondary analysis of PK parameters between the 1×30 mg Formulation B and a 1×30 mg Formulation A was completed, with the results of this analysis shown in Table 25. As shown in Table 24, for all endpoints based on morphine plasma concentrations, the 90% confidence for the estimated ratio of means lay within the boundaries of 0.80 to 1.25, and none of the ratios were statistically significantly different from 100.

TABLE 25

Secondary Analysis of Morphine PK Parameters - 1 × 30 mg Formulation B versus 1 × 30 mg Formulation A

| | Means | | Form B/Form A | | |
|---|---|---|---|---|---|
| | Form. B | Form. A | | | |
| | (1 × 30 mg) | (1 × 30 mg) | Ratio | 90% CI | p-value |
| Full PK data set: | | | | | |
| $AUC_{(0-48\,h)}$ (nmol*h/L) | 277.8 | 291.5 | 95.3 | (88.9, 102.2) | 0.2551 |
| $AUC_{(0-inf)}$ (nmol*h/L) | 326.5 | 338.4 | 96.5 | (87.3, 106.7) | 0.5569 |
| $C_{max}$ (nmol/L) | 18.0 | 16.6 | 108.2 | (100.5, 116.6) | 0.0811 |
| Completers only: | | | | | |
| $AUC_{(0-48\,h)}$ (nmol*h/L) | 282.2 | 295.7 | 95.5 | (88.8, 102.6) | 0.2899 |
| $AUC_{(0-inf)}$ (nmol*h/L) | 332.6 | 346.8 | 95.9 | (86.3, 106.6) | 0.5114 |
| $C_{max}$ (nmol/L) | 18.3 | 16.7 | 109.4 | (101.3, 118.2) | 0.0547 |
| PK set-tail less 20%: | | | | | |
| $AUC_{(0-inf)}$ (nmol*h/L) | 296.8 | 312.5 | 95.0 | (86.5, 104.2) | 0.3604 |

Formulation A (1*30 mg) is derived by dividing AUC and $C_{max}$ by 2—since two tablets were administered.

Endpoints are log-transformed before analysis, and results are transformed back and presented as ratios. The model includes period and treatment as fixed effects and subject as a random effect.

Estimates and comparisons are based on the full model with all treatments included.

The mean is the geometric mean estimated from the model.

Yet another explorative analysis was comparing the 24 hour plasma concentrations of morphine from formulation B to formulation A. The ratio between 60 mg Egalet® Morphine Formulation B and 2×30 mg Egalet® Morphine Formulation A at hour 24 was 116.0% (CI: 98.5%-136.7%), p=0.1351.

Safety Results

A total of 105 treatment emergent adverse experiences (TEAEs) were reported by 17 of the 24 subjects who received at least one dose of the study medication (safety population). No adverse events were severe, significant, or serious.

No safety issues were observed with respect to clinical laboratory results and vital signs results.

No relevant differences were observed among the treatment groups with respect to mean values and changes from baseline for vital signs and clinical laboratory results.

As the 90% confidence intervals for the regression coefficient of the log-dose for $AUC_{0-48h}$ and $C_{max}$ were contained within the interval 0.8-1.25 for morphine, dose-linearity was demonstrated. Since the estimated coefficient of the log-dose for $AUC_{0-48h}$ as well as $C_{max}$ were larger than 1 and the lower limit of the 90% confidence interval was larger than 1, there was some statistical evidence of over-proportionality. Combining these two observations, some deviation from dose proportionality was present, but in the light of the protocol defined limits, this deviation was concluded not clinically relevant. Evaluating the slight deviation from proportionality between the dose levels, Table 26 gives the ratios between geometric means after adjusting for dose.

TABLE 26

| | Ratio of Geometric Means | | |
|---|---|---|---|
| | 60 mg/30 mg | 100 mg/60 mg | 200 mg/100 mg |
| $AUC_{0-48}$ | 1.16 | 1.03 | 1.04 |
| $AUC_{0-inf}$ | 1.15 | 1.00 | 1.01 |
| $C_{max}$ | 1.14 | 1.01 | 1.16 |

The invention claimed is:

1. A tablet for oral delivery of oxycodone, the tablet comprising:
   a) a matrix composition having a cylindrical shape with two ends, wherein each of the two ends is optionally tapered, the length of the matrix is in the range of 7.5 to 15 mm, the matrix composition comprises (i) oxycodone and (ii) at least one polyglycol, and the matrix composition exhibits a release rate of the oxycodone from the matrix in ethanol that is equal to or lower than the release rate of the oxycodone from the matrix in water; and
   b) a coating substantially surrounding the matrix composition and having one or two openings exposing at least one surface of the matrix composition, the coating being substantially impermeable to an aqueous medium,
   wherein the tablet provides controlled release of the oxycodone over an interval of 24 hours,
   wherein the tablet provides a $C_{min}$ reached no earlier than 18 hours after last administration and wherein the tablet is resistant to isolation of the oxycodone by any of crushing of the tablet, melting of the tablet, and ethanol extraction.

2. The tablet according to claim 1, wherein the area of the cross section of the matrix is in the range of 1 to 75 mm$^2$.

3. The tablet according to claim 1, wherein the area of the cross section of the matrix is at least 20 mm$^2$.

4. The tablet according to claim 1, wherein the length of the matrix is selected from the group consisting of 8 to 15 mm, 8 to 10 mm, and 9 to 9.5 mm.

5. The tablet according to claim 1, wherein the length of the matrix is selected from the group consisting of 7.5 to 12 mm, 7.5 to 10 mm, and 7.5 to 8 mm.

6. The tablet according to claim 1, wherein the coating comprises two openings each exposing one end of the matrix.

7. The tablet according to claim 1, wherein a therapeutically effective response is achieved over the entire interval between administrations.

8. The tablet according to claim 1, wherein the tablet provides a steady state trough of oxycodone that is selected from the group consisting of at least 20%, at least 30%, at least 40%, and at least 50% of steady state $C_{max}$.

9. The tablet according to claim 1, wherein the tablet provides a steady state trough of oxycodone that is in a range selected from the group consisting of 30 to 80% of steady state $C_{max}$ and 40 to 80% of steady state $C_{max}$.

10. The tablet according to claim 1, wherein the tablet provides controlled release of oxycodone such that a $2^{nd}$ point where a plasma concentration of oxycodone of 50% of steady state $C_{max}$ is reached is at a time selected from the group consisting of no earlier than 4 hours and no earlier than 12 hours after last administration.

11. The tablet according to claim 1, wherein a $1^{st}$ point where a plasma concentration of oxycodone of 50% of steady state $C_{max}$ is reached is in the range of 0.5 to 2.5 hours after last administration.

12. The tablet according to claim 1, wherein the tablet provides controlled release of oxycodone in a manner that results in a MRT selected from the group consisting of at least 11 hours and at least 15 hours.

13. The tablet according to claim 1, wherein the tablet provides controlled release of oxycodone in a manner that results in a $T_{max}$ selected from the group consisting of 3 to 6 hours and 4 to 6 hours after last administration to a steady state individual.

14. The tablet according to claim 1, wherein the tablet provides a protraction index selected from the group consisting of at least 0.20 and at least 0.30.

15. The tablet according to claim 1, wherein the tablet delivers sufficient oxycodone in a controlled manner over a 24-hour period to achieve pain relief over a 24-hour period.

16. The tablet according to claim 1, wherein each dosage of the oxycodone is in the range of 10 to 500 mg.

17. The tablet according to claim 1, wherein the polyglycol is a water soluble crystalline or semi-crystalline polymer.

18. The tablet according to claim 1, comprising at least one polyglycol that is a homopolymer.

19. The tablet according to claim 1, comprising at least one polyglycol that is a copolymer.

20. The tablet according to claim 1, wherein the total concentration of the at least one polyglycol included in the matrix composition is selected from the group consisting of 5 to 99% w/w, 15 to 95% w/w, 30 to 90% w/w, 30 to 85% w/w, 30 to 80% w/w, 40 to 80% w/w, 45 to 75% w/w, 40 to 50% w/w, 45 to 50% w/w, 60 to 85% w/w, 60 to 80% w/w, and 70 to 75% w/w.

21. The tablet according to claim 18, wherein the at least one polyglycol is a polyethylene glycol and/or a polyethylene oxide.

22. The tablet according to claim 21, wherein the polyethylene glycol and/or polyethylene oxide has a molecular weight selected from the group consisting of 20,000 to 700,000 daltons, 20,000 to 600,000 daltons, 35,000 to 500,000 daltons, 35,000 to 400,000 daltons, 35,000 to 300,000 daltons, 50,000 to 300,000 daltons, 200,000 daltons, and 300,000 daltons.

23. The tablet according to claim 1, wherein the matrix comprises at least two different polyglycols, wherein the different polyglycols are selected from the group consisting of polyethylene oxides.

24. The tablet according to claim 23, wherein one polyethylene oxide has an average molecular weight in the range of 150,000 to 250,000 daltons and the other polyethylene oxide has an average molecular weight in the range of 250,000 to 350,000 daltons.

25. The tablet according to claim 18, wherein the concentration of homopolymer in the matrix composition is selected from the group consisting of 5 to 90% w/w, 20 to 85% w/w, 20 to 75% w/w, 20 to 70% w/w, 20 to 40% w/w, 30 to 85% w/w, 30 to 75% w/w, 30 to 50% w/w, 30 to 40% w/w, 30 to 35% w/w, 31 to 33% w/w, 50 to 85% w/w, 60 to 80% w/w, 70 to 80% w/w, 70 to 75% w/w, and 71 to 73% w/w.

26. The tablet according to claim 19, wherein the copolymer is a poloxamer that has an average molecular weight selected from the group consisting of 2,000 to 30,000 daltons, 2,000 daltons to 20,000 daltons, 4,000 daltons to 18,000 daltons, and 6,000 daltons to 10,000 daltons.

27. The tablet according to claim 19, wherein the matrix comprises one or more copolymers selected from the group consisting of poloxamers.

28. The tablet according to claim 27, wherein the matrix comprises only one poloxamer and has a length selected from the group consisting of 7.5 to 15 mm and of 7.5 to 10 mm.

29. The tablet according to claim 19, wherein the concentration of copolymer in the matrix composition is selected from the group consisting of 0 to 30% w/w, 1 to 20% w/w, 2 to 10% w/w, 2 to 5% w/w, 5 to 30% w/w, 5 to 20% w/w, and 5 to 15% w/w.

30. The tablet according to claim 1, wherein the coating is insoluble in an aqueous medium.

31. The tablet according to claim 1, wherein the coating comprises one or more polymers selected from the group consisting of starch based polymers, cellulose based polymers, synthetic polymers, and biodegradable polymers.

32. The tablet according to claim 1, wherein the coating comprises one or more polymers selected from the group consisting of ethyl cellulose grade 20, ethyl cellulose grade 100, polylactic acid (PLA), Cornpack 200, polycaprolactone, PEO 7000000, and polyhydroxybuturate.

33. The tablet according to claim 1, wherein the coating comprises an ethyl cellulose selected from an ethyl cellulose of grade 20 and an ethyl cellulose of grade 100.

34. The tablet according to claim 1, wherein the coating comprises one or more biodegradable polymers, selected from the group consisting of polylactic acid and polycaprolactone.

35. The tablet according to claim 1, wherein the coating comprises at least 85% polymers, and wherein the polymers are selected from the group consisting of biodegradable polymers and cellulose based polymers.

36. The tablet according to claim 1, wherein the coating comprises one or more plasticizers.

37. The tablet according to claim 1, wherein the tablet is formed by injection molding or extrusion.

* * * * *

(12) SUPPLEMENTAL EXAMINATION CERTIFICATE

United States Patent  (10) Number: 8,563,038 F1
Andersen et al.  (45) Certificate Issued: Feb. 2, 2016

Control No.: 96/000,130  Filing Date: Nov. 11, 2015
Primary Examiner: Carlos N. Lopez No substantial new question of patentability is raised in the request for supplemental examination. See the Reasons for Substantial New Question of Patentability Determination in the file of this proceeding.

(56) Items of Information

U.S. PATENT DOCUMENTS

| | | |
|---|---|---|
| 20040151772 | 8/2004 | Andersen et al. |
| 20070003617 | 1/2007 | Fischer et al. |

OTHER DOCUMENTS

Haahr, "Drug Resistant, Controlled Release Using Egalet Dosage Units," Poster, Proceedings of the 34th Annual Meeting Exposition of the Controlled Release Society, July 7-11 (2007).

Response to non-final Office Action filed May 14, 2012 during prosecution of the '067 application ("May 2012 Response"). This paper was responsive to the non-final Office Action issued on November 11, 2011.

Response to final Office Action filed January 10, 2013, during prosecution of the '067 application ("January 2013 Response"). This paper was responsive to the Final Office action issued on September 10, 2012.